(12) United States Patent
Yamazaki et al.

(10) Patent No.: US 12,694,530 B2
(45) Date of Patent: Jul. 28, 2026

(54) ELECTRONIC DEVICE AND DISPLAY SYSTEM RECOGNIZING EYE FATIGUE AND LOOKING AWAY

(71) Applicant: SEMICONDUCTOR ENERGY LABORATORY CO., LTD., Atsugi (JP)

(72) Inventors: Shunpei Yamazaki, Tokyo (JP); Tetsuya Kakehata, Isehara (JP)

(73) Assignee: SEMICONDUCTOR ENERGY LABORATORY CO., LTD., Kanagawa-ken (JP)

( * ) Notice: Subject to any disclaimer, the term of this patent is extended or adjusted under 35 U.S.C. 154(b) by 98 days.

(21) Appl. No.: 18/282,910

(22) PCT Filed: Mar. 17, 2022

(86) PCT No.: PCT/IB2022/052409
§ 371 (c)(1),
(2) Date: Sep. 19, 2023

(87) PCT Pub. No.: WO2022/200936
PCT Pub. Date: Sep. 29, 2022

(65) Prior Publication Data
US 2024/0169539 A1 May 23, 2024

(30) Foreign Application Priority Data
Mar. 25, 2021 (JP) ................................. 2021-052048

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0077* (2013.01); *A61B 5/1072* (2013.01); (Continued)

(58) Field of Classification Search
None
See application file for complete search history.

(56) References Cited

U.S. PATENT DOCUMENTS

| 8,899,752 B2 | 12/2014 | Kato et al. |
| 11,195,088 B2 | 12/2021 | Ikeda |

(Continued)

FOREIGN PATENT DOCUMENTS

| CN | 110770737 A | 2/2020 |
| CN | 110969981 A | 4/2020 |

(Continued)

OTHER PUBLICATIONS

International Search Report (Application No. PCT/IB2022/052409) Dated Jun. 21, 2022.

(Continued)

*Primary Examiner* — Michael J Cobb
(74) *Attorney, Agent, or Firm* — NIXON PEABODY LLP; Jeffrey L. Costellia

(57) ABSTRACT

An electronic device capable of estimating a user's situation is to be provided. The electronic device includes a camera, a processing portion, and a display portion. The camera has a function of capturing an image of a user's eye and his/her periphery repeatedly to generate a plurality of pieces image data. The processing portion has a function of detecting, from the plurality of pieces of image data, a change over time in information including at least one of a frequency of eye blinks, a time taken for one blink, a distance between an upper eyelid and a lower eyelid, a sight direction, and an area of a pupil, a function of estimating a level of user's eye fatigue on the basis of the change over time in information, and a function of generating string information in accor- (Continued)

dance with the estimated level of user's eye fatigue. The display portion has a function of displaying string information.

15 Claims, 36 Drawing Sheets

(51) Int. Cl.

| | |
|---|---|
| *A61B 5/107* | (2006.01) |
| *A61B 5/11* | (2006.01) |
| *A61B 5/16* | (2006.01) |
| *G06F 3/01* | (2006.01) |
| *G09B 5/06* | (2006.01) |
| *G09B 5/14* | (2006.01) |
| *H04R 1/10* | (2006.01) |

(52) U.S. Cl.
CPC .......... *A61B 5/1079* (2013.01); *A61B 5/1103* (2013.01); *A61B 5/163* (2017.08); *A61B 5/165* (2013.01); *A61B 5/6803* (2013.01); *A61B 5/7264* (2013.01); *A61B 5/742* (2013.01); *G06F 3/01* (2013.01); *G06F 3/013* (2013.01); *G06T 2207/20081* (2013.01); *G06T 2207/20084* (2013.01); *G06T 2207/30041* (2013.01); *G09B 5/065* (2013.01); *G09B 5/14* (2013.01); *H04R 1/1041* (2013.01)

(56) References Cited

U.S. PATENT DOCUMENTS

| | | | |
|---|---|---|---|
| 11,568,224 B2 | 1/2023 | Kurokawa et al. | |
| 2008/0146892 A1* | 6/2008 | LeBoeuf .............. | A61B 5/4812 600/300 |
| 2009/0099785 A1 | 4/2009 | Yamamoto et al. | |
| 2016/0090097 A1* | 3/2016 | Grube ................... | B60W 40/08 340/576 |
| 2017/0231490 A1* | 8/2017 | Toth ....................... | G16H 40/63 600/558 |
| 2020/0125935 A1 | 4/2020 | Kurokawa et al. | |
| 2020/0387678 A1* | 12/2020 | Hara ........................ | G06N 3/04 |
| 2021/0068742 A1* | 3/2021 | Goto .................... | A61B 5/1079 |
| 2021/0259565 A1 | 8/2021 | Ohno et al. | |
| 2021/0287561 A1 | 9/2021 | Udaka et al. | |
| 2022/0217325 A1* | 7/2022 | Lee ........................ | G06V 40/19 |
| 2022/0273211 A1 | 9/2022 | Akimoto et al. | |
| 2022/0277591 A1 | 9/2022 | Oguni et al. | |
| 2022/0292880 A1 | 9/2022 | Oguni et al. | |
| 2025/0228484 A1* | 7/2025 | Oshio ................. | A61B 5/0077 |

FOREIGN PATENT DOCUMENTS

| | | | |
|---|---|---|---|
| CN | 112188867 A | 1/2021 |
| JP | 2003-339681 A | 12/2003 |
| JP | 2009-093509 A | 4/2009 |
| JP | 2009-284996 A | 12/2009 |
| JP | 2012-050759 A | 3/2012 |
| JP | 2012-073876 A | 4/2012 |
| JP | 2018-109968 A | 7/2018 |
| JP | 2019-017876 A | 2/2019 |
| JP | 2020-099670 A | 7/2020 |
| KR | 2020-0020813 A | 2/2020 |
| WO | WO-2012/160741 | 11/2012 |
| WO | WO-2015/072202 | 5/2015 |
| WO | WO-2018/234919 | 12/2018 |
| WO | WO-2020/054855 | 3/2020 |
| WO | WO-2020/129426 | 6/2020 |

OTHER PUBLICATIONS

Written Opinion (Application No. PCT/IB2022/052409) Dated Jun. 21, 2022.

* cited by examiner

FIG. 4A
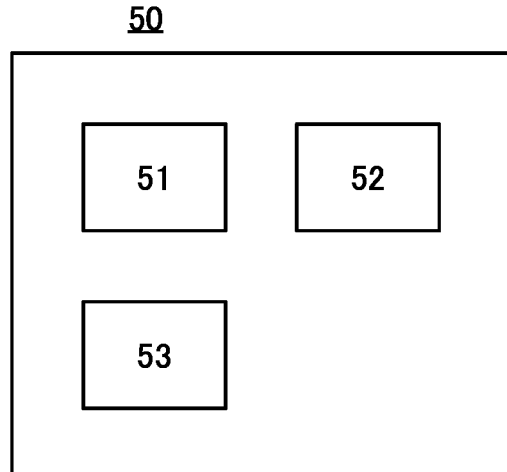
FIG. 4B
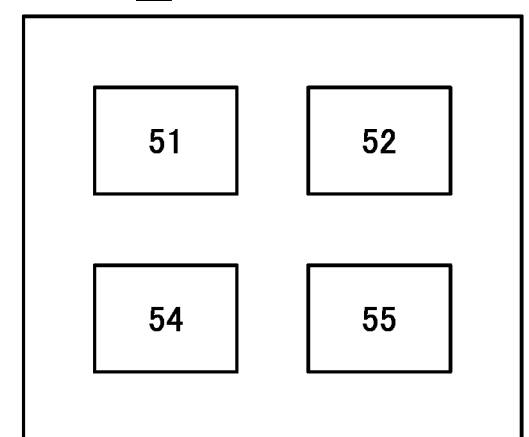
FIG. 4C
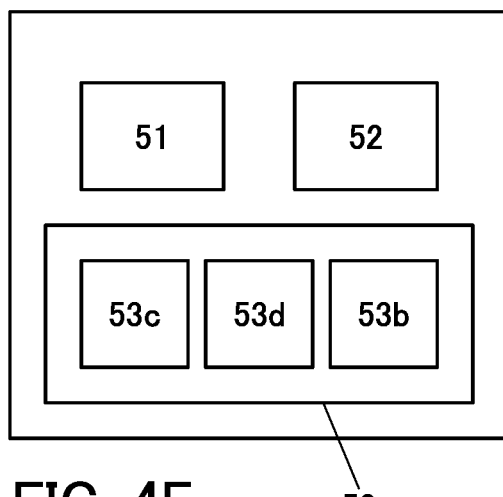
FIG. 4D
FIG. 4E
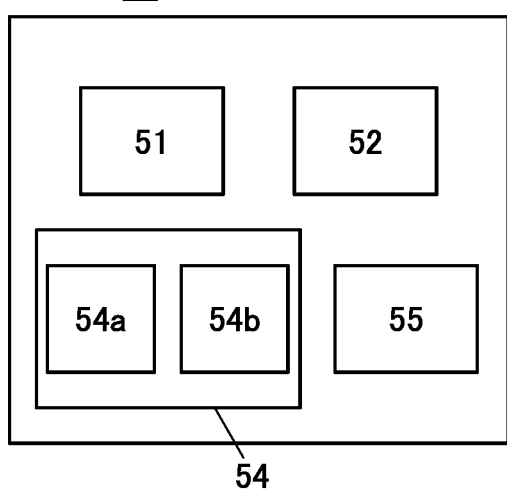

ANN

First layer (k-1)-th layer k-th layer R-th layer

FIG. 34A
8300
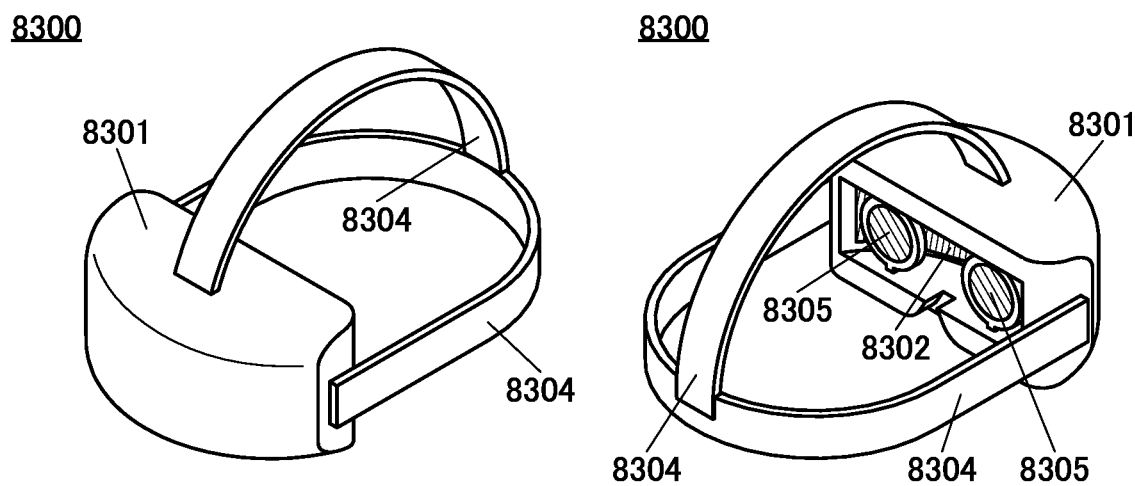
FIG. 34B
8300
FIG. 34C
8300
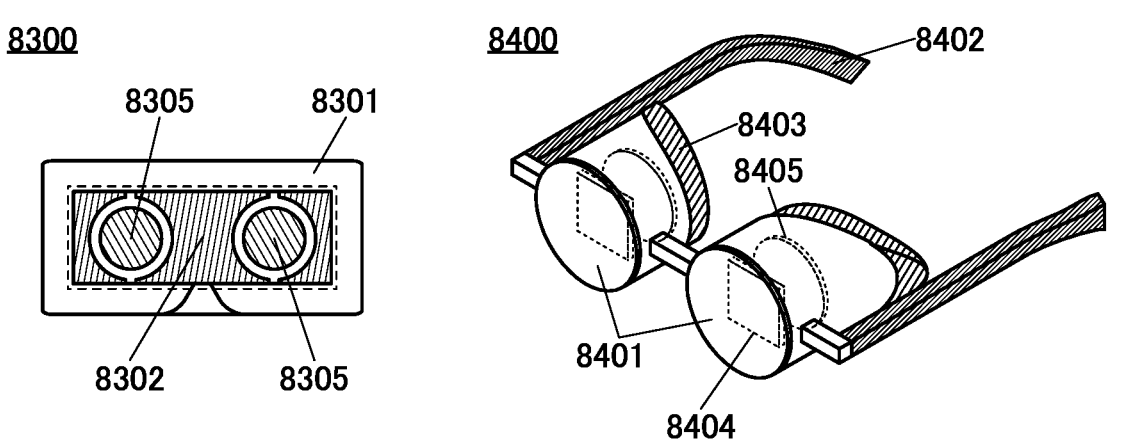
FIG. 34D
8400
FIG. 34E
8200
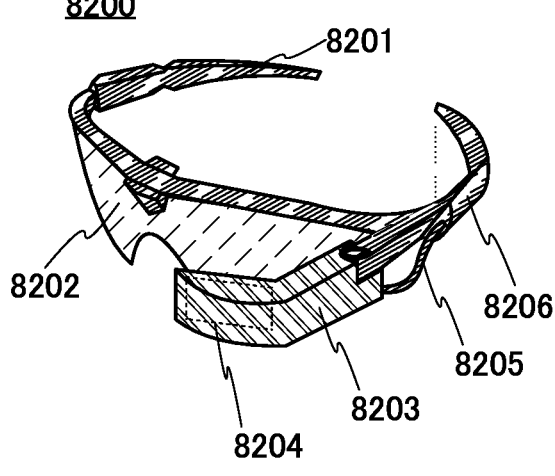

ELECTRONIC DEVICE AND DISPLAY SYSTEM RECOGNIZING EYE FATIGUE AND LOOKING AWAY

TECHNICAL FIELD

One embodiment of the present invention relates to an electronic device and a display system.

Note that one embodiment of the present invention is not limited to the above technical field. Examples of a technical field of one embodiment of the present invention disclosed in this specification and the like include a semiconductor device, a display device, a light-emitting apparatus, a power storage device, a memory device, an electronic device, a lighting device, an input device, an input/output device, a driving method thereof, and a manufacturing method thereof.

Background Art

In recent years, with the progress of shifting to remote classes, teleworks, and the like, an opportunity of using electronic devices having display functions has rapidly increased. This prolongs a time of looking straight at a display portion of the electronic device and is making an environment prone to promote eye fatigue. The accumulation of eye fatigue causes a risk of falling asleep, losing user's concentration, and the like.

A method for measuring the level of eye fatigue has recently attracted attention. Patent Document 1 discloses a visual fatigue level measuring system that evaluates the user's visual fatigue level by comparing eye movements between two or more time segments.

REFERENCE

Patent Document

[Patent Document 1] PCT International Publication No. 2012/160741

SUMMARY OF THE INVENTION

Problems to be Solved by the Invention

Examples of remote classes include synchronous interactive classes and on-demand classes. In the synchronous interactive class, especially, the class is held while the real-time interactive communication is maintained in real time. In conventional classes held at a classroom or the like, a teacher and students are in the same space, and thus the teacher can grasp situations of the students relatively easily. On the other hand, in the synchronous interactive class, the teacher has to check situations of the students only based on image data displayed on a display portion of an electronic device. It is difficult to evaluate the fatigue levels, particularly, the eye fatigue levels, of the students on the basis of the image data.

In view of the above object, an object of one embodiment of the present invention is to provide an electronic device capable of estimating a user's situation. Another object of one embodiment of the present invention is to provide an electronic device capable of outputting string information in accordance with a user's situation. Another object of one embodiment of the present invention is to provide a display system capable of estimating a situation of a participant in a remote location. Another object of one embodiment of the present invention is to provide a display system capable of outputting string information in accordance with a situation of a participant in a remote location. Another object of one embodiment of the present invention is to provide a novel electronic device.

Note that the description of these objects does not preclude the existence of other objects. Note that one embodiment of the present invention does not have to achieve all these objects. Note that objects other than these can be derived from the description of the specification, the drawings, the claims, and the like.

Means for Solving the Problems

One embodiment of the present invention is an electronic device including a camera, a processing portion, and a display portion. The camera has a function of capturing images of an eye of a user and a periphery of the eye repeatedly to generate a plurality of pieces of image data. The processing portion has a function of detecting, from the plurality of pieces of image data, a change over time in information including at least one of a frequency of eye blinks, a time taken for one blink, a distance between an upper eyelid and a lower eyelid, a sight direction, and an area of a pupil, a function of estimating a level of user's eye fatigue on the basis of the change over time in information, and a function of generating string information in accordance with the estimated level of user's eye fatigue. The display portion has a function of displaying the string information.

In the above electronic device, the level of user's eye fatigue is preferably estimated using a learned model which is generated through supervised learning performed on a neural network.

In the above electronic device, the processing portion preferably includes an arithmetic circuit which has a function of performing a product-sum operation and estimates the level of user's eye fatigue on the basis of the change over time in information.

In the above electronic device, the arithmetic circuit preferably includes a transistor including a metal oxide in a channel formation region.

Another embodiment of the present invention is an electronic device including a camera, a processing portion, a display portion, and headphones. The headphones include a sensor portion. The sensor portion has a function of obtaining a change over time in information. The processing portion has a function of estimating a user's stress situation on the basis of the change over time in information and a function of generating string information in accordance with the user's stress situation. The display portion has a function of displaying the string information. In the above electronic device, the user's stress situation is preferably estimated using a learned model which is generated through supervised learning performed on a neural network.

In the above electronic device, the processing portion preferably includes an arithmetic circuit which has a function of performing a product-sum operation and estimates the user's stress situation on the basis of the change over time in information.

In the above electronic device, the arithmetic circuit preferably includes a transistor including a metal oxide in a channel formation region.

Another embodiment of the present invention is a display system including a first electronic device and a second electronic device and being capable of obtaining eye information of a user of the first electronic device. The first electronic device includes a camera and a processing portion. The camera has a function of capturing an image of an eye of the user of the first electronic device and a periphery of the eye repeatedly to generate a plurality of pieces of image data. The processing portion has a function of detecting, from the plurality of pieces of image data, a change over time in information including at least one of a frequency of eye blinks, a time taken for one blink, a distance between an upper eyelid and a lower eyelid, a sight direction, and an area of a pupil, a function of estimating a level of user's eye fatigue on the basis of the change over time in information, and a function of generating string information in accordance with the estimated level of user's eye fatigue. The second electronic device includes a display portion. The display portion has a function of displaying the string information accepted from the first electronic device.

In the above display system, the level of user's eye fatigue is preferably estimated using a learned model which is generated through supervised learning performed on a neural network.

In the above display system, the processing portion preferably includes an arithmetic circuit which has a function of performing a product-sum operation and estimates the level of user's eye fatigue on the basis of the change over time in information.

Another embodiment of the present invention is a display system including a first electronic device and a second electronic device and being capable of obtaining eye information of a user of the first electronic device. The first electronic device includes a camera, a processing portion, and headphones. The headphones include a sensor portion, and the sensor portion has a function of obtaining a change over time in information. The processing portion has a function of estimating a user's stress situation on the basis of the change over time in information and a function of generating string information in accordance with the user's stress situation. The second electronic device includes a display portion. The display portion has a function of displaying the string information accepted from the first electronic device.

In the above display system, the user's stress situation is preferably estimated using a learned model which is generated through supervised learning performed on a neural network.

In the above display system, the processing portion preferably includes an arithmetic circuit which has a function of performing a product-sum operation and estimates the user's stress situation on the basis of the change over time in information.

Effect of the Invention

According to one embodiment of the present invention, an electronic device capable of estimating a situation of a user can be provided. According to another embodiment of the present invention, an electronic device capable of outputting string information in accordance with a situation of a user can be provided. According to another embodiment of the present invention, a display system capable of estimating a situation of a participant in a remote location can be provided. According to another embodiment of the present invention, a display system capable of outputting string information in accordance with a situation of a participant in a remote location can be provided. According to another embodiment of the present invention, a novel electronic device can be provided.

Note that the description of these effects does not preclude the existence of other effects. One embodiment of the present invention does not need to have all of these effects. Note that effects other than these can be derived from the description of the specification, the drawings, the claims, and the like.

BRIEF DESCRIPTION OF THE DRAWINGS

FIG. 4A to FIG. 4E are block diagrams each illustrating a structure example of an electronic device.

FIG. 6A and FIG. 6B are block diagrams each illustrating a structure example of a display system.

FIG. 18 is a cross-sectional view illustrating an example of a display device.

FIG. 34A to FIG. 34E are diagrams illustrating examples of electronic devices.

MODE FOR CARRYING OUT THE INVENTION

Figure 1:
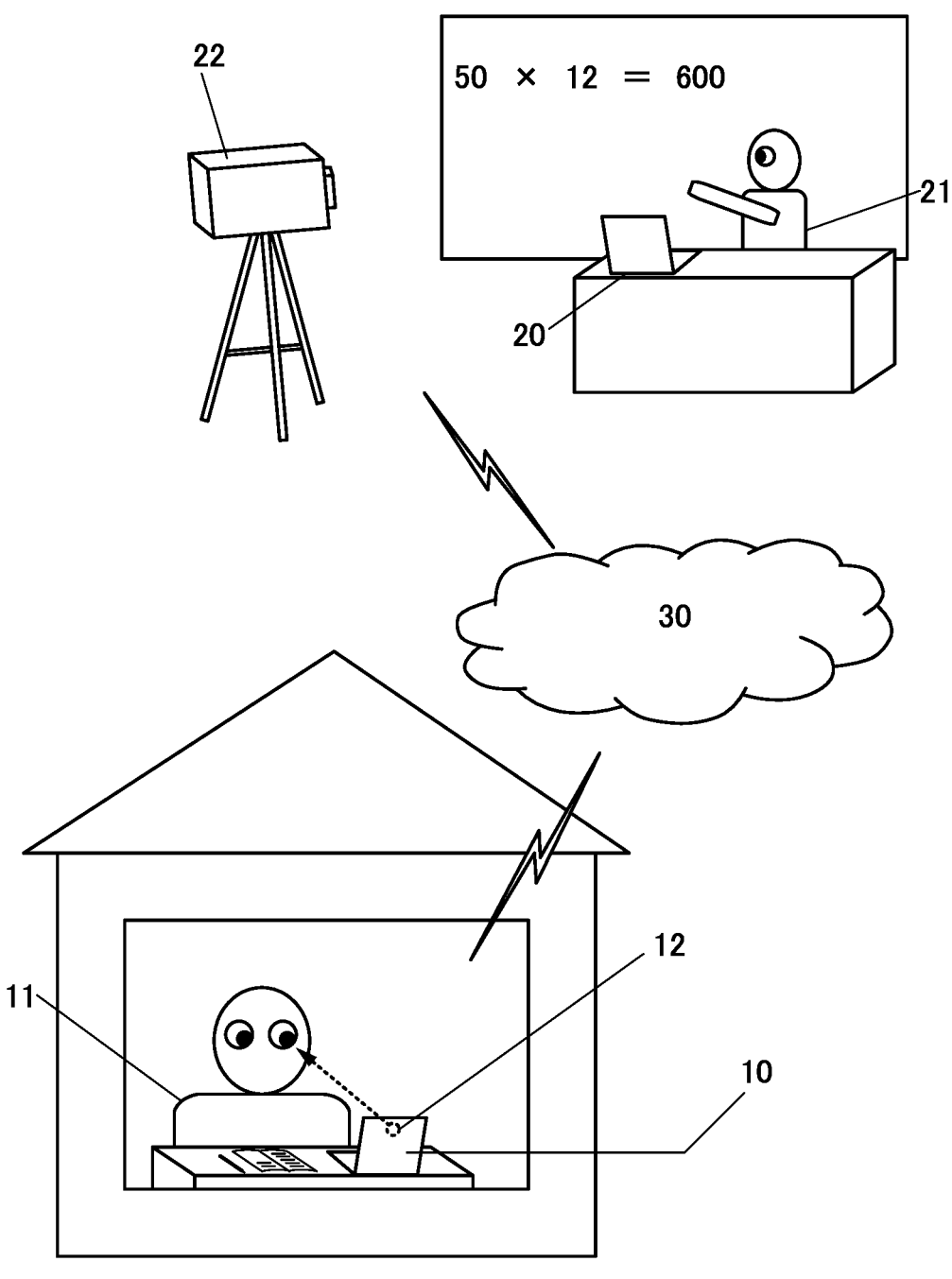
FIG. 1 is a diagram illustrating a usage example of an electronic device.

Embodiments are described in detail with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Note that in structures of the invention described below, the same portions or portions having similar functions are denoted by the same reference numerals in different drawings, and the description thereof is not repeated. Furthermore, the same hatch pattern is used for the portions having similar functions, and the portions are not especially denoted by reference numerals in some cases.

The position, size, range, or the like of each component illustrated in drawings does not represent the actual position, size, range, or the like in some cases for easy understanding. Therefore, the disclosed invention is not necessarily limited to the position, size, range, or the like disclosed in the drawings.

The term "film" and the term "layer" can be interchanged with each other depending on the case or circumstances. For example, the term "conductive layer" can be replaced with the term "conductive film". As another example, the term "insulating film" can be replaced with the term "insulating layer".

Embodiment 1

In this embodiment, an electronic device and a display system of one embodiment of the present invention will be described with reference to drawings. Note that the display system of one embodiment of the present invention includes at least one electronic device of one embodiment of the present invention.

The electronic device or the display system of one embodiment of the present invention includes a camera, a processing portion, and a display portion. With this structure, one embodiment of the present invention enables estimation of a user's situation. Specifically, an image of a user's eye and a periphery thereof captured with the camera is analyzed, whereby the user's situation can be estimated, and information on the estimated user's situation can be displayed on the display portion. In addition, the information on the estimated user's situation is transmitted to another electronic device different from the above electronic device and accepted by the another electronic device different from the above electronic device, whereby information on the user's situation can be displayed on a display portion of the another electronic device different from the above electronic device. Note that in this specification and the like, the sentence "an electronic device accepts information or data" can be replaced with "an electronic device receives data or information", "an electronic device obtains information or data", or the like.

With one embodiment of the present invention, a user of the electronic device can recognize his/her own situation. Furthermore, with one embodiment of the present invention, a user of an electronic device can recognize a situation of another user of an electronic device different from the above electronic device. Thus, one embodiment of the present invention, with a plurality of electronic devices, can be favorably used in a meeting where sounds, images, and materials are shared through a network. Examples of the meeting include a remote class, a teleconference, an online interview, and an online medical examination. Hereinafter, the remote class, the teleconference, the online interview, the online medical examination, or the like is referred to as a remote meeting in some cases.

An example of using an electronic device of one embodiment of the present invention is described with reference to FIG. 1. FIG. 1 illustrates a situation where a remote class is held with use of an electronic device 10 and an electronic device 20.

A situation illustrated in FIG. 1 is that a teacher 21 gives a lesson in a classroom or the like. Giving a lesson is recorded with a camera 22, whereby image data is generated. The image data is transmitted to the electronic device 10 of a student 11 through a network 30.

FIG. 1 also illustrates a situation where the student 11 is taking a class at his/her home. The electronic device 10 accepts the image data through the network 30. The student 11 watches the image data displayed on a display portion of the electronic device 10, thereby capable of taking a class.

The electronic device 10 includes a camera 12. The camera 12 captures an image of the student 11 and his/her periphery to generate image data. The image data preferably includes an eye (eyes) of the student 11. The image data is transmitted to the electronic device 20 of the teacher 21 through the network 30.

The electronic device 20 accepts the image data transmitted from the electronic device and displays the image data on a display portion included in the electronic device 20. The teacher 21 watches the image data displayed on the display portion included in the electronic device 20, thereby being capable of checking a situation of the student 11.

Although the camera 22 is used for recording the lesson in FIG. 1, a camera included in the electronic device 20 may be used for the recording.

As described above, data transmission and reception between the electronic device 10 and the electronic device 20 enables the remote class to be held. Although the participants of the remote class illustrated in FIG. 1 are the teacher 21 and the student 11, a plurality of students may participate in the remote class. In this case, each student uses the electronic device 10; that is, two or more electronic devices 10 are used in the remote class.

<Display Example of Display Portion in Electronic Device>

Figure 2A:
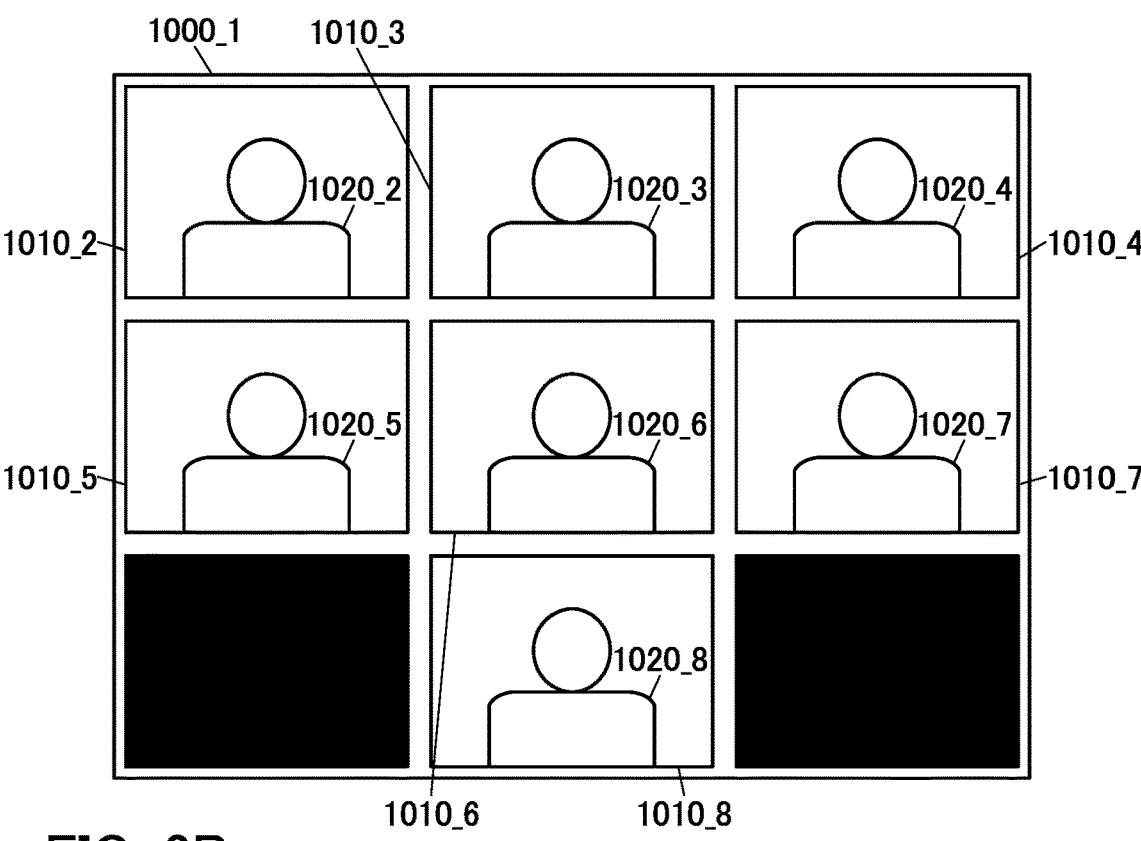
FIG. 2A and FIG. 2B are diagrams illustrating display examples of a display portion of an electronic device.
Figure 2B:
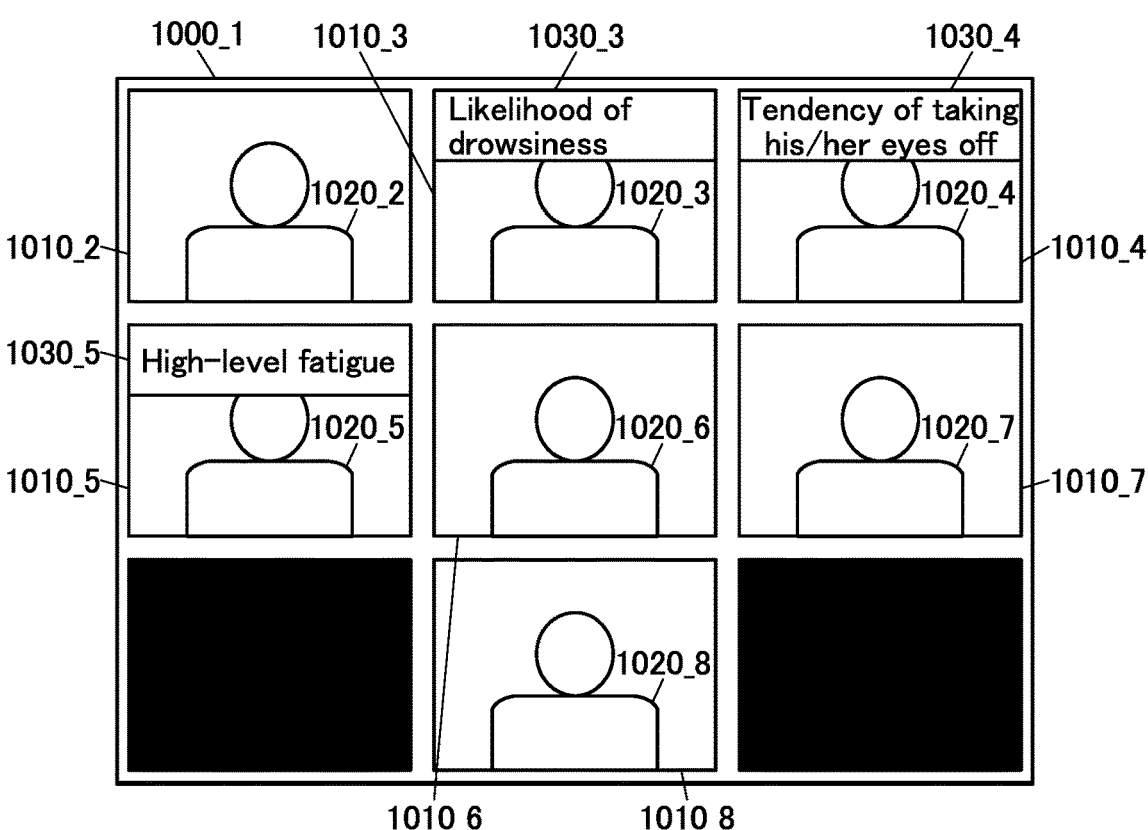

FIG. 2A and FIG. 2B illustrate display examples of a display portion of an electronic device of one embodiment of the present invention. Note that the display examples in FIG. 2A and FIG. 2B show a remote meeting held with use of first to eighth electronic devices. Note that the number of electronic devices used in the remote meeting is not limited to eight, the number of the electronic devices may be more than or equal to two and less than or equal to seven, or more than nine.

In the following description, a remote class is assumed as the remote meeting. An assumed user of the first electronic device is a teacher. The first electronic device corresponds to the above-described electronic device 20, and the teacher corresponds to the above-described teacher 21. Assumed users of the second to eighth electronic devices are students. One of the second to eighth electronic devices corresponds to the above-described electronic device 10, and one of the students corresponds to the above-described student 11.

The first electronic device includes a display portion 1000_1. In addition, the first electronic device is used by a user 1020_1.

FIG. 2A illustrates a display example of the display portion 1000_1 immediately after the beginning of the remote meeting. FIG. 2B illustrates a display example of the display portion 1000_1 after a while since the beginning of the remote meeting.

In FIG. 2A and FIG. 2B, an image 1010_2 to an image 1010_8 are displayed on the display portion 1000_1. The image 1010_2 to the image 1010_8 are images captured with cameras included in the second to eighth electronic devices. The second to the eighth electronic devices are used by a user 1020_2 to a user 1020_8. In this case, the image 1010_2 to the image 1010_8 include the user 1020_2 to the user 1020_8 and peripheries thereof, respectively. Note that the image 1010_2 to the image 1010_8 preferably includes eyes of the user 1020_2 to the user 1020_8.

Immediately after the beginning of the remote meeting, no change in situations of the user 1020_2 to the user 1020_8 is observed. Thus, as illustrated in FIG. 2A, the displayed image 1010_2 to the image 1010_8 are images captured with the cameras included in the second to the eighth electronic devices, respectively. In other words, the image 1010_2 to the image 1010_8 include the user 1020_2 to the user 1020_8 and peripheries thereof, respectively.

After a while since the beginning of the remote meeting, some of users may have a high level of eye fatigue. In this case, an image including string information is displayed to be superimposed on at least part of the image including the user whose eye fatigue level is high and the periphery thereof. For example, in the case where the user 1020_3 suffers from high-level eye fatigue, an image 1030_3 is displayed to be superimposed on the image 1010_3 as illustrated in FIG. 2B. The image 1030_3 includes string information ("likelihood of drowsiness" in FIG. 2B).

Furthermore, after a while since the beginning of the remote meeting, some of the users may take his/her eyes off. In this case, an image including string information is displayed to be superimposed on at least part of the image including the user taking his/her eyes are off and the periphery thereof. For example, in the case where the user 1020_4 takes his/her eyes off, an image 1030_4 is displayed to be superimposed on the image 1010_4 as illustrated in FIG. 2B. The image 1030_4 includes string information ("tendency of taking his/her eyes off" in FIG. 2B).

Furthermore, after a while since the beginning of the remote meeting, some of the users may have a high level of fatigue. In this case, an image including string information is displayed to be superimposed on at least part of the image including the user suffering from high-level fatigue and the periphery thereof. For example, in the case where the user

1020_5 suffers from high-level fatigue, an image 1030_5 is displayed to be superimposed on the image 1010_5 as illustrated in FIG. 2B. The image 1030_5 includes string information ("high-level fatigue" in FIG. 2B).

As described above, with use of one embodiment of the present invention, the user of the first electronic device can recognize the situations of the other users as string information. For example, the user 1020_1 can easily recognize a user with high-level eye fatigue, a user taking his/her eyes off, or the like in the user 1020_2 to the user 1020_8 and can communicate closely with such a user. In particular, in the case of a remote meeting with a large number of participants, each of images displayed on the display portion 1000_1 is reduced in size, which makes it difficult to grasp situations of the users displayed on the display portion 1000_1. Thus, one embodiment of the present invention can be suitably used for a remote meeting with a large number of participants.

Figure 3A:
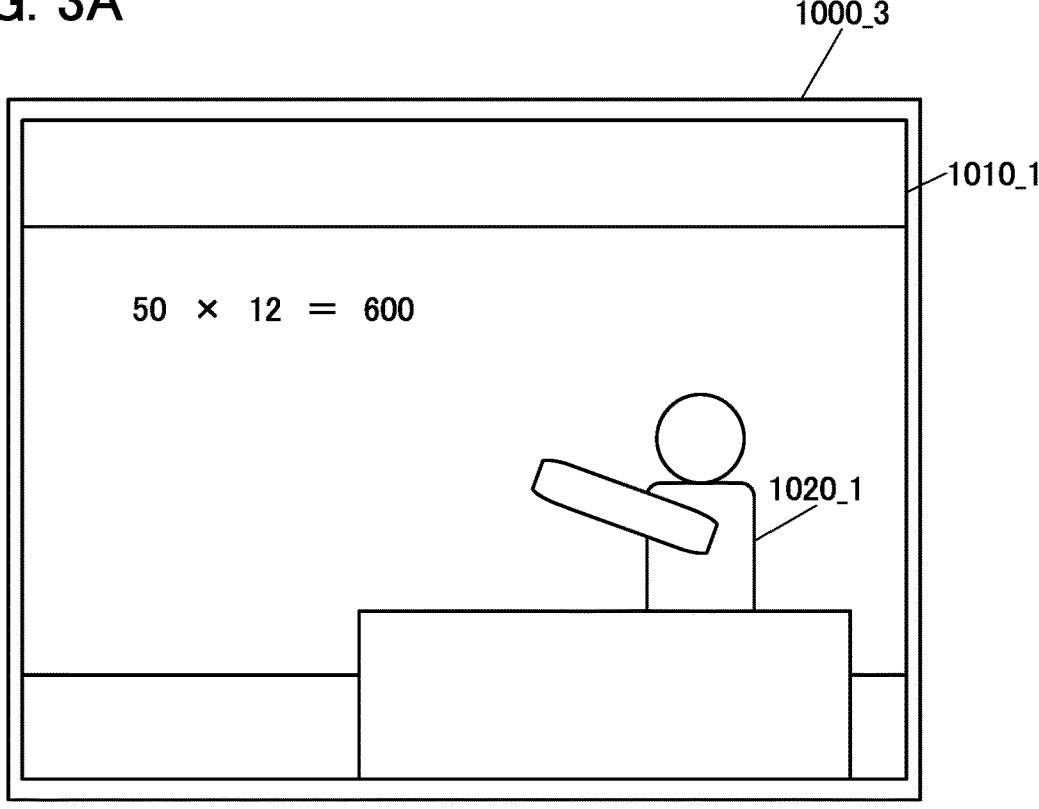
FIG. 3A and FIG. 3B are diagrams illustrating display examples of a display portion of an electronic device.
Figure 3B:
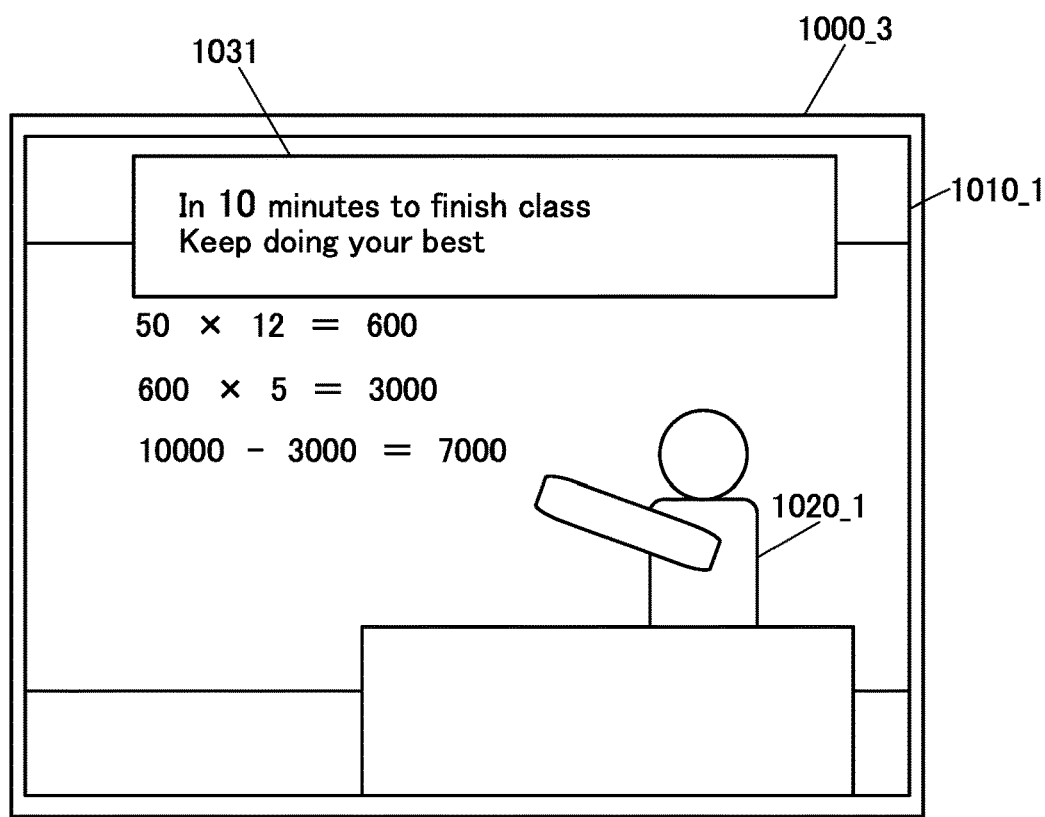

The information string reflecting the situations of the user 1020_2 to the user 1020_8 may be displayed on the display portions in the second to eighth electronic devices. FIG. 3A and FIG. 3B illustrate display examples of the display portion included in the third electronic device.

The third electronic device includes a display portion 1000_3.

The display example of FIG. 3A illustrates that on the display portion 1000_3 immediately after the beginning of the remote meeting. The display example of FIG. 3B illustrates that of the display portion 1000_3 after a while since the beginning of the remote meeting.

In FIG. 3A and FIG. 3B, the display portion 1000_3 displays an image 1010_1. The image 1010_1 includes an image taken with the camera included in the first electronic device. For example, the image 1010_1 includes the user 1020_1 and his/her periphery. The image 1010_1 in FIG. 3A and FIG. 3B includes a blackboard, a white board, or an electronic blackboard as the periphery of the user 1020_1.

Immediately after the beginning of the remote meeting, no change in the situation of the user 1020_3 is observed. Thus, the display portion 1000_3 displays the image captured with the camera in the electronic device, as illustrated in FIG. 3A.

After a while since the beginning of the remote meeting, the user 1020_3 gets into a situation where the user 1020_3 has high-level eye fatigue as described above. At this time, the image 1031 is displayed to be superimposed on the image 1010_1. The image 1031 includes string information ("In 10 minutes to finish the class. Keeping doing your best" in FIG. 3B).

As described above, with use of one embodiment of the present invention, the users of the electronic devices other than the first electronic device can recognize their own situations as string information. For example, the user 1020_3 can easily recognize his/her own situation even when the user 1020_3 is not aware of any symptoms, and accordingly can rally his/her concentration on the remote meeting.

Note that the function of the electronic device of one embodiment of the present invention is not restricted to displaying string information. For example, the electronic device may have a function of outputting string information as sounds or a function of outputting an alarm sound such as a beep. With this function, a sound or an alarm sound is output, which can trigger the user to rally his/her concentration on the remote meeting even when the user does not look at the display portion of the electronic device in such a situation that the user takes his/her eyes off or falls into a sleep.

The remote meeting is not limited to the remote class given in the above and can be a teleconference, an online interview, an online medical examination, and the like. In this case, examples of the user of the first electronic device include a manager in the teleconference, an interviewer in the online interview, and a doctor in the online medical examination. Examples of the user of the electronic device other than the first electronic device include a team member in the teleconference, an applicant or candidate in the online interview, and a consulter in the online medical examination.

<Structure Example of Electronic Device and Display System>

Structure examples of an electronic device and a display system of one embodiment of the present invention are described with reference to block diagrams in FIG. 4A to FIG. 6B.

FIG. 4A to FIG. 4E are block diagrams illustrating an electronic device of one embodiment of the present invention.

An electronic device 50 illustrated in FIG. 4A includes a camera 51, a display portion 52, and a processing portion 53. The camera 51, the display portion 52, and the processing portion 53 transmit and receive various kinds of signals to and from one another through a bus wiring (not illustrated in FIG. 4A) or the like.

The camera 51 has a function of capturing an image of a user of the electronic device 50 to generate image data. The image capturing is preferably repeated at a regular interval. Repeating the image capturing can generate a planarity of pieces of image data. The image data preferably includes the user and his/her periphery, further preferably includes the user's eye. A plurality of pieces of image data including the user's eye are generated, which enables information on eye blinks or the like to be detected with high accuracy.

The processing portion 53 accepts the plurality of pieces of image data through the bus wiring or the like.

The processing portion 53 has a function of analyzing the image. The plurality of pieces of image data are analyzed, whereby string information can be generated. The user's situation included in the plurality of pieces of image data is reflected in the string information.

For the above image analysis, a neural network, an arithmetic circuit having a function of performing a product-sum operation, or the like can be used. In other words, the processing portion 53 includes at least one of a processing device capable of running a program including a neural network, an arithmetic circuit having a function of performing a product-sum operation, and the like.

It is particularly preferable that an arithmetic circuit having a function of performing a product-sum operation be used for the above image analysis. Note that an arithmetic circuit having a function of performing a product-sum operation can be rephrased as an arithmetic circuit capable of arithmetic processing based on a neural network. The use of the arithmetic circuit enables the image analysis to be performed with low power. Accordingly, power consumption of an electronic device of one embodiment of the present invention or a display system including the electronic device can be reduced. Note that details of the arithmetic circuit having a function of performing a product-sum operation will be described in Embodiment 2.

For the above image analysis, a neural network may be used. For the neural network, deep learning is preferably used. For the deep learning, a convolutional neural network (CNN), a recurrent neural network (RNN), an autoencoder (AE), a variational autoencoder (VAE), random forest, a support vector machine, gradient boosting, a generative adversarial network (GAN), or the like is preferably used, for example.

The processing portion 53 has a function of determining whether a situation of a user is higher than or equal to a threshold value. On the basis of the above determination result, it is preferable to determine whether or not the string information is displayed. For example, the electronic device 50 is configured to output string information only when the user's situation is higher than or equal to the threshold value, whereby the user of the electronic device 50 can easily recognize the string information output by the electronic device 50. Note that the threshold value is preferably set in advance.

When the processing portion 53 estimates a situation of a user, the situation of a user is preferably quantified. The quantified situation of a user facilitates the determination. Note that in this specification and the like, a numerical value representing a situation of a user or a quantified situation of a user is simply referred to as a situation of a user in some cases.

Furthermore, the processing portion 53 may have a function of estimating a situation of a user from the plurality of pieces of image data and a function of generating string information based on the user's situation. Examples of the user's situation includes the fatigue level of the user, the sight direction of the user, and the degree of stress of the user. Note that the description of a fatigue level of a user in this specification and the like includes a level of user's eye fatigue. The eye fatigue level can also be referred to as eyestrain or the degree of eyestrain. In particular, when the plurality of pieces of image data include the user's eye and a periphery thereof, the level of user's eye fatigue or the user's sight direction can be estimated with high accuracy.

In the above structure, the processing portion 53 may include a processing portion 53a having a function of estimating a situation of the user from a plurality of pieces of image data and a processing portion 53b having a function of generating string information based on the user's situation. The electronic device 50 illustrated in FIG. 4B includes the processing portion 53 including the processing portion 53a and the processing portion 53b. At least one of the processing portion 53a and the processing portion 53b has a function of determining whether the user's situation is higher than or equal to a threshold value. Although FIG. 4B illustrates a structure in which the electronic device 50 includes the processing portion 53a and the processing portion 53b; however the structure is not limited thereto. The processing portion 53a and the processing portion 53b are separately provided in two electronic devices.

Alternatively, the processing portion 53 may have a function of detecting a change over time in information on the eye from the plurality of pieces of image data, a function of estimating a situation of the user on the basis of the change over time in information on the eye, and a function of generating string information based on the user's situation. The information on the eye includes at least one of the frequency of eye blinks, the time taken for one blink, the distance between an upper eyelid and a lower eyelid, the sight direction, and the area of a pupil. In particular, when the plurality of pieces of image data include the user's eye and a periphery thereof, the information on the eye can be detected with high accuracy.

In the above structure, the processing portion 53 may include a processing portion 53c having a function of detecting a change over time in information on the eye from the plurality of pieces of image data, a processing portion 53$d$ having a function of estimating a situation of the user on the basis of the change over time in information on the eye, and the processing portion 53$b$ generating string information in accordance with the user's situation. The electronic device 50 illustrated in FIG. 4C includes the processing portion 53 including the processing portion 53$b$ to the processing portion 53$d$. At least one of the processing portion 53$d$ and the processing portion 53$b$ has a function of determining whether the user's situation is higher than or equal to a threshold value. Although FIG. 4C illustrates a structure in which the electronic device 50 includes the processing portion 53$b$ to the processing portion 53$d$; however the structure is not limited thereto. Some of the processing portion 53$b$ to the processing portion 53$d$ may be provided in one electronic device, and some of the other processing portion 53$b$ to the processing portion 53$d$ may be provided in another electronic device. Alternatively, the processing portion 53$b$ to the processing portion 53$d$ may be provided separately in three electronic devices.

The display portion 52 has a function of outputting the string information generated by the processing portion 53. The string information is displayed on the display portion 52 as image data. Alternatively, the string information is displayed as image data on the display portion 52 so as to be superimposed on another image data. Thus, the string information described in this specification and the like can also be referred to as image data including string where the user's situation is reflected, in some cases.

Although the electronic device 50 illustrated in FIG. 4A and the like include one display portion 52, two or more display portions 52 may be provided in the electronic device.

An electronic device of one embodiment of the present invention may include a sensor portion in addition to the camera, the display portion, and the processing portion. The electronic device 50 illustrated in FIG. 4D includes the camera 51, the display portion 52, a processing portion 54, and a sensor portion 55. The camera 51, the display portion 52, the processing portion 54, and the sensor portion 55 transmit and receive various kinds of signals to and from one another through a bus wiring (not illustrated in FIG. 4D) or the like.

The sensor portion 55 has a function of detecting (obtaining) information. For example, the sensor portion 55 has a function of detecting (obtaining) information including at least one of the pulse, the blood pressure, and the body temperature of a user. The detection of the information is performed at a regular interval during a remote meeting. In this case, the sensor portion 55 can be regarded as having a function of obtaining a change over time in information. For example, the sensor portion 55 can be regarded as having a function of obtaining a change over time in information including at least one of the pulse, the blood pressure, and the body temperature of a user.

As the sensor portion 55, a light-receiving device (also referred to as sensor device) or the like may be used. Specifically, a light-receiving device that detects visible light, a light-receiving device that detects infrared light, and the like can be used. In this case, the sensor portion 55 enables capturing an image of a user and his/her periphery.

The sensor portion 55 is provided in headphones, for example. The headphones described in this specification and the like include earphones used in close to user's ears, headphones in combination of one or two earphone(s) and a headband or a chinband, headphones into which a micro-phone is incorporated (also referred to as headset), and earphones into which a microphone is incorporated.

The headphones can be connected directly or connected with wire to a housing of the electronic device 50. Moreover, the headphones and the electronic device 50 may be provided with a magnet. Such a structure is preferable because the headphones can be fixed to the housing of the electronic device 50 with the magnet, which makes housing the headphones easy.

The headphones including the sensor portion 55 is not necessarily included in the electronic device 50. For example, the headphones may include a communication portion and has a wireless communication function. The sensor portion 55 included in the headphones can transmit the information detected by the wireless communication to the processing portion 54. The information transmission to the processing portion 54 is repeated at a regular interval during the remote meeting.

When the above headphones have a wireless communication function, the processing portion 54 receives the above information from the sensor portion 55 through the communication portion included in the electronic device 50 with the wireless communication function. Alternatively, when the above headphones are connected directly or connected with wire to a housing of the electronic device 50, the processing portion 54 accepts the above information from the sensor portion 55 through the bus wiring. The information acceptance is repeated at a regular interval during the remote meeting. Thus, the processing portion 54 can accept a change over time in the above information.

The processing portion 54 has a function of analyzing the change over time in information. Analysis of the change over time in information enables generation of string information. Note that the situation of the user of the headphones including the sensor portion 55 is reflected in the string information.

For the above analysis of the change over time in information, a neural network, an arithmetic circuit having a function of performing a product-sum operation, or the like can be used. In other words, the processing portion 54 includes at least one of a processing device capable of running a program including a neural network, an arithmetic circuit having a function of performing a product-sum operation, and the like. As the neural network or the arithmetic circuit, the above-described neural network or arithmetic circuit applicable to the above-described image analysis can be used.

Note that the processing portion 54 may have a function of estimating a situation of the user on the basis of the change over time in information and a function of generating string information based on the user's situation. Examples of the user's situation include the fatigue level of the user and the degree of stress of the user.

In the above structure, the processing portion 54 may include a processing portion 54$a$ that estimates a situation of the user on the basis of a change over time in information and a processing portion 54$b$ that generates string information based on the user's situation. The electronic device 50 illustrated in FIG. 4E includes the processing portion 54 including the processing portion 54$a$ and the processing portion 54$b$. At least one of the processing portion 54$a$ and the processing portion 54$b$ has a function of determining whether the user's situation is higher than or equal to a threshold value. Although FIG. 4E illustrates an example of a structure in which the electronic device 50 includes the processing portion 54$a$ and the processing portion 54$b$, the structure is not limited thereto. The processing portion 54*a* and the processing portion 54*b* may be provided separately in two electronic devices.

Thus, the electronic device of one embodiment of the present invention can display string information where a situation of a user of the electronic device is reflected. For example, when the electronic device is used by a student in a remote class, a team member in a teleconference, an applicant or candidate in an online interview, a consulter in an online medical examination, or the like, the user can easily recognize his/her own situation even if the user is not aware of any symptoms, and accordingly can rally his/her concentration on the remote meeting.

Note that the electronic device of one embodiment of the present invention can include any one or more of a frame memory, an audio, a control portion, a communication portion, a battery, and the like in addition to the camera, the display portion, and the processing portion.

Figure 5A:
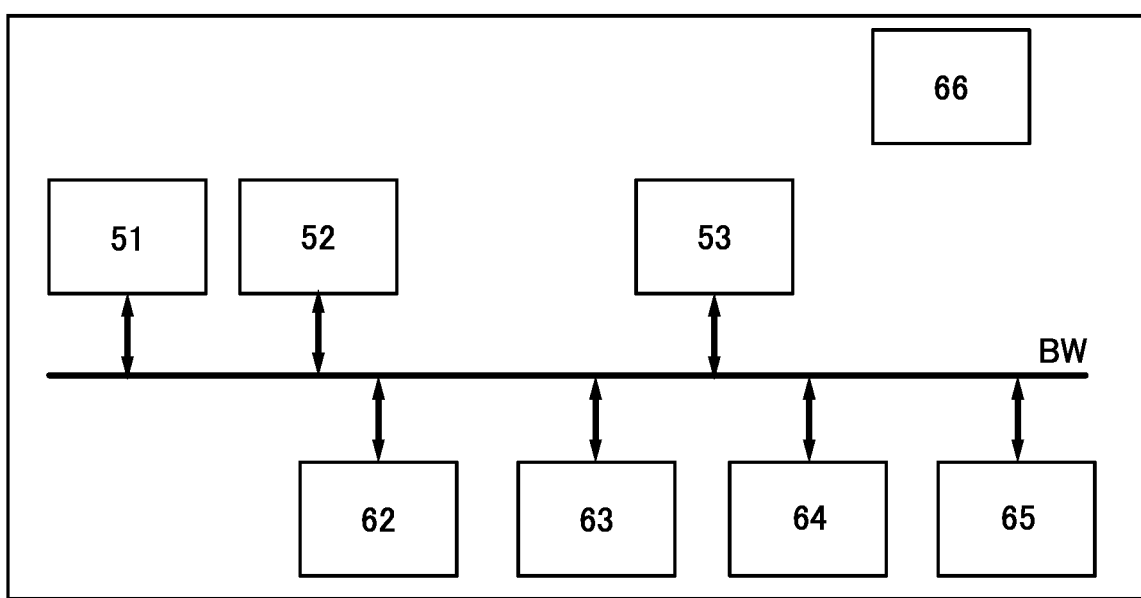
FIG. 5A and FIG. 5B are block diagrams each illustrating a structure example of an electronic device.

The electronic device 50 illustrated in FIG. 5A is different from the electronic device 50 illustrated in FIG. 4A in including a frame memory 62, an audio 63, a control portion 64, a communication portion 65, and a battery 66 in addition to the camera 51, the display portion 52, and the processing portion 53. The camera 51, the display portion 52, the processing portion 53, the frame memory 62, the audio 63, the control portion 64, and the communication portion 65 transmit and receive various kinds of signals to and from one another through a bus wiring BW.

The display portion 52 includes a driver circuit portion. The driver circuit portion includes a gate driver circuit and a source driver circuit. Each of the number of gate driver circuits provided and the number of source driver circuits provided may be one or two or more.

The audio 63 includes, for example, one or more of a microphone and a speaker. The control portion 64 includes a CPU, a GPU, and a memory. The communication portion 65 can transmit and receive data to and from another terminal or a server on a network through wireless communication.

Image data generated in the control portion 64 is stored in the frame memory 62 through the bus wiring BW. The image data stored in the frame memory 62 is displayed on the display portion 52 through the source driver included in the above driver circuit portion. When the display portion 52 outputs string information generated by the processing portion 53 as well as the image data, the display portion 52 displays the image data and the string information. At this time, the string information is preferably displayed to be superimposed on the image data.

Data (analog data) obtained by the camera or the sensor device is converted into digital data by the processing portion 53 and transmitted to the control portion 64. For example, the sensor device obtains information on a user, and the processing portion 53 estimates a situation of the user from the detected information. The control portion 64 receives information on the user's situation from the processing portion 53 and reflect it in image data the user sees.

The electronic device may include one or both of an optical system and a motion detection portion in addition to any one or more of the camera, the display portion, the processing portion, the frame memory, the audio, the control portion, the communication portion, the battery, and the like. Examples of such an electronic device include information terminals (wearable devices) that can be worn on the head such as a head-mounted display, a glasses-type terminal, and a goggle-type terminal.

Figure 5B:
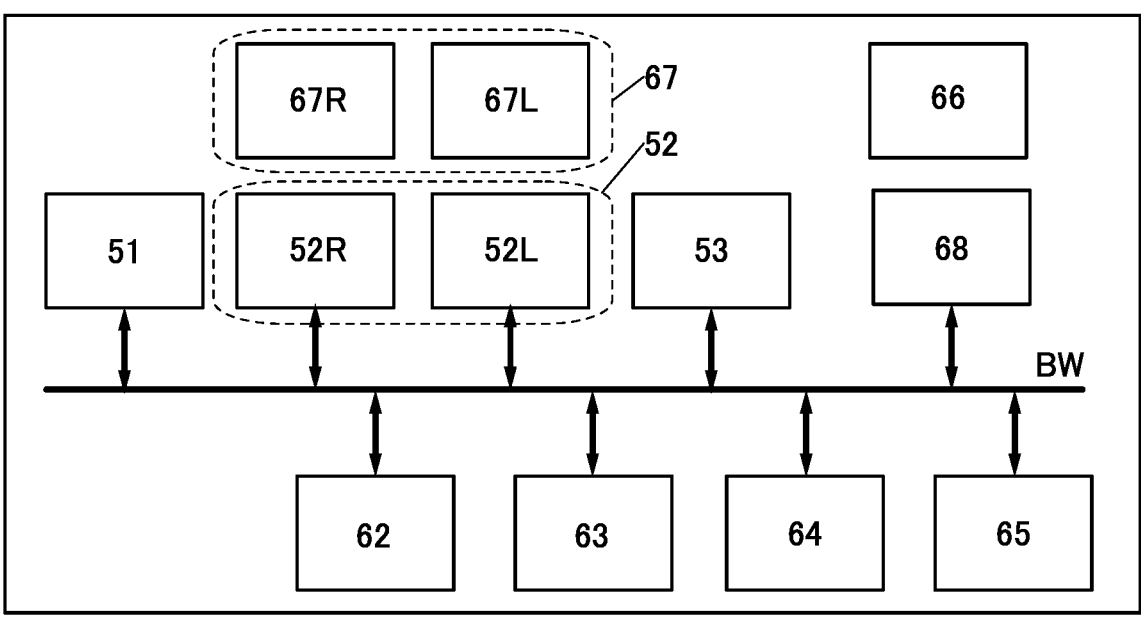

The electronic device 50 illustrated in FIG. 5B is different from the electronic device 50 illustrated in FIG. 5A in including an optical system 67 and a motion detection portion 68 in addition to the camera 51, the display portion 52, the processing portion 53, the frame memory 62, the audio 63, the control portion 64, the communication portion 65, and the battery 66. Note that in the electronic device 50 illustrated in FIG. 5B, the display portion 52 includes a display portion 52R and a display portion 52L, and the optical system 67 includes an optical system 67R and an optical system 67L.

The camera 51, the display portion 52, the processing portion 53, the frame memory 62, the audio 63, the control portion 64, the communication portion 65, and the motion detection portion 68 transmit and receive various kinds of signals to and from one another through the bus wiring BW.

The motion detection portion 68 includes an inertial sensor having a function of sensing a body motion of a user. Note that the inertial sensor here refers to a sensor for sensing the acceleration and angular velocity of an object.

The optical system 67 includes a lens, for example. In addition, the optical system 67 may include a reflective plate, a half mirror, a waveguide, or the like as necessary. Although in the example illustrated in FIG. 5B, two optical systems 67 for the right eye and the left eye are provided, the number of the optical systems 67 provided may be one or three or more.

Note that one embodiment of the present invention is not limited to the electronic devices having the structures illustrated in FIG. 4A to FIG. 5B. For example, one embodiment of the present invention may be a display system including two electronic devices as illustrated in FIG. 6A.

Figures 6A, 6B:
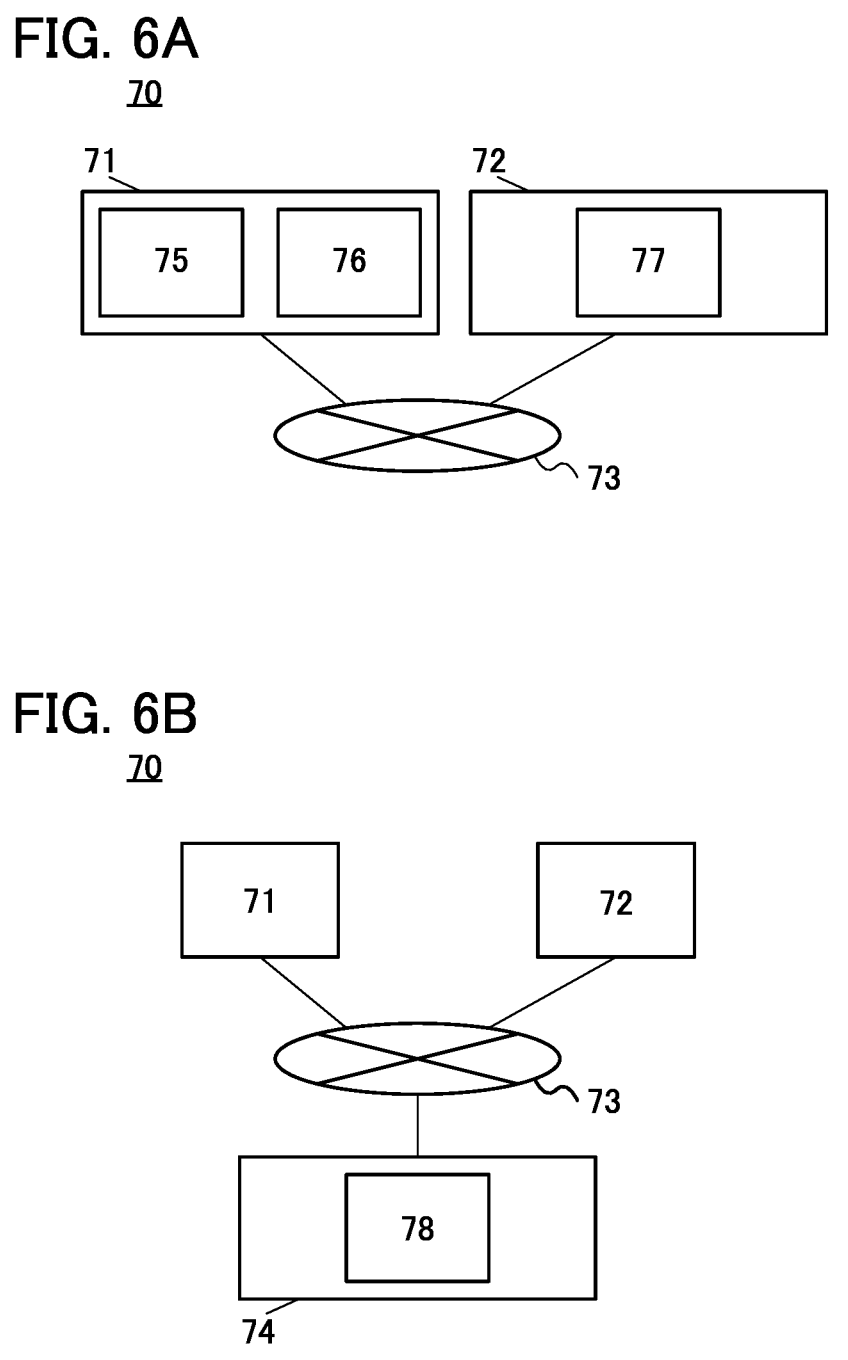

FIG. 6A is a block diagram illustrating a structure example of a display system of one embodiment of the present invention. As illustrated in FIG. 6A, a display system 70 includes an electronic device 71 and an electronic device 72. Note that the electronic device 71 corresponds to the above-described electronic device 50. Therefore, the description of the electronic device 50 can be referred to for the description of the electronic device 71 other than the contents in the following description. The electronic device 72 may include some or all of functions of the above-described electronic device 50. For example, the electronic device 72 preferably has a function of the display portion 52 of the electronic device 50.

The electronic device 71 and the electronic device 72 are connected through a network 73.

The network 73 is a computer network such as the Internet, which is an infrastructure of the World Wide Web (WWW), an intranet, an extranet, a PAN (Personal Area Network), a LAN (Local Area Network), a CAN (Campus Area Network), a MAN (Metropolitan Area Network), a WAN (Wide Area Network), or a GAN (Global Area Network). Note that the network 73 includes wired or wireless communication.

The electronic device 71 includes a camera 75 and a processing portion 76. The electronic device 71 captures an image of a user and his/her periphery with use of the camera 75. The captured image preferably includes an eye (eyes) of the user. The electronic device 71 generates string information with use of the processing portion 76.

The camera 75 corresponds to the above-described camera 51. The processing portion 76 corresponds to the above-described processing portion 53.

The electronic device 71 may include a sensor portion. In this case, the electronic device 71 detects (obtains) information with use of the sensor portion. For example, the electronic device 71 detects (obtains) information including at least one of the pulse, the blood pressure, and the body temperature of a user, with use of the sensor portion. Furthermore, the electronic device 71 obtains a change over time in information with use of the sensor portion. For example, the electronic device 71 obtains a change over time in the information including at least one of the pulse, the blood pressure, and the body temperature of a user, with use of the sensor portion. Moreover, the electronic device 71 generates string information with use of the processing portion 76.

The above sensor portion corresponds to the above-described sensor portion 55. The processing portion 76 corresponds to the above-described processing portion 54.

The electronic device 72 includes a processing portion 77. The electronic device 72 accepts the string information from the electronic device 71 through the network 73 and displays the string information on the display portion included in the electronic device 72. In other words, the display portion in the electronic device 72 has a function of displaying the string information accepted from the electronic device 71.

With this structure, the electronic device 72 can output string information in accordance with a situation of a user of the electronic device 71. When the electronic device 71 is used at a location far away from the electronic device 72, the electronic device 72 can output string information in accordance with a situation of a user of the electronic device 71 who participates in a remote meeting at the remote location. In other words, the display system 70 can estimate a situation of the user at the remote location. Furthermore, the display system 70 can output string information in accordance with the situation of the user at the remote location.

Accordingly, a user of the electronic device 72 can recognize a situation of a user of the electronic device 71 as string information. In other words, the user of the electronic device 72 can recognize a situation of the user of the electronic device 71, on the basis of information other than an image captured with the camera 75 provided for the electronic device 71, a sound obtained with a microphone provided for the electronic device 71, or the like. Thus, the user of the electronic device 72 can communicate closely with the user of the electronic device 71. For example, it is preferable that the electronic device 71 be used by a client (guest) and the electronic device 72 be used by a host. Specifically, the electronic device 71 may be used by a student in a remote class, a team member in a teleconference, an applicant or candidate in an online interview, a consulter in an online medical examination, or the like, and the electronic device 72 may be used by a teacher in the remote class, a manager in the teleconference, an interviewer in the online interview, a doctor in the online medical examination, or the like.

Note that data communicated between the electronic device 71 and the electronic device 72 is not limited to string information. For example, the data communicated between the electronic device 71 and the electronic device 72 can be data of a captured image of a user of the electronic device 71 and a periphery of the user. In this case, the electronic device 72 may generate string information based on the image data accepted with use of the processing portion 77, and display the string information on the display portion included in the electronic device 72. In this structure, the processing portion 77 corresponds to the above-described processing portion 53.

For the data communicating between the electronic device 71 and the electronic device 72 can be data including at least one of the pulse, the blood pressure, and the body temperature of a user. In this case, the electronic device 72 may generate string information with use of the processing portion 77, and display the string information on the display portion included in the electronic device 72. In this structure, the processing portion 77 corresponds to the above-described processing portion 54.

For generation of string information, features (a character, a gesture, and the like) of the user of the electronic device 71 may be used as well as image data obtained by capturing an image of the user of the electronic device 71 and a periphery of the user and/or information including at least one of the pulse, the blood pressure, and the body temperature of the user of the electronic device 71. Accordingly, string information suitable for the user of the electronic device 71 can be generated. In other words, string information taking account for an individual difference can be generated.

Alternatively, the processing portion 76 may have a function of the above-described processing portion 53*a* or processing portion 54*a*, and the processing portion 77 may have a function of the above-described processing portion 53*b* or processing portion 54*b*. In this case, data communicated between the electronic device 71 and the electronic device 72 corresponds to information on the user's situation estimated by the processing portion 76. The data communication volume between the electronic device 71 and the electronic device 72 can be reduced because the information on the user's situation has a smaller volume of data than the image data obtained by capturing an image of a user and his/her periphery and/or the information including at least one of the pulse, the blood pressure, and the body temperature of the user.

Alternatively, the processing portion 76 may have functions of the above-described processing portion 53*c* and processing portion 53*d*, and the processing portion 77 may have a function of the above-described processing portion 53*b*. In this case, data communicating between the electronic device 71 and the electronic device 72 corresponds to information on the user's situation estimated by the processing portion 76. The data communication traffic between the electronic device 71 and the electronic device 72 can be reduced because the information on the user's situation has a smaller amount of data volume than the image data obtained by capturing an image of a user and his/her periphery.

Alternatively, the processing portion 76 may have a function of the above-described processing portion 53*c*, and the processing portion 77 may have functions of the above-described processing portion 53*b* and processing portion 53*d*. In this case, data communicating between the electronic device 71 and the electronic device 72 corresponds to a change over time in information on the user's eye detected by the processing portion 76. The data communication traffic between the electronic device 71 and the electronic device 72 can be reduced because the change over time in information on the user's eye has a smaller amount of data volume than the image data obtained by capturing an image of a user and his/her periphery.

FIG. 6A illustrates a structure in which the display system 70 includes the electronic device 71 and the electronic device 72; however, the present invention is not limited to the structure. For example, the display system may include m (m is an integer greater than or equal to 3) electronic devices. Note that the m electronic devices are connected to each other through the network 73. Some or all of the m electronic devices each correspond to the above-described electronic device 50. Furthermore, some of the m electronic devices may have some or all of the functions of the above-described electronic device 50. Accordingly, at least m participants can join a remote meeting.

As another example, a display system of one embodiment of the present invention may include two electronic devices and one server as illustrated in FIG. 6B.

FIG. 6B is a block diagram illustrating a structure example of a display system of one embodiment of the present invention. As illustrated in FIG. 6B, the display system 70 includes the electronic device 71, the electronic device 72, and a server 74. The electronic device 71 corresponds to the above-described electronic device 50. Thus, the description of the above electronic device 50 can be referred to for the description of the electronic device 71 other than the contents in the following description. The electronic device 72 has a function of the above-described electronic device 71.

The electronic device 71, the electronic device 72, and the server 74 are connected to each other through the network 73.

The server 74 includes a processing portion 78.

The server 74 accepts data from the electronic device 71 through the network 73. The data includes at least one of the following: image data obtained by capturing an image of a user of the electronic device 71 and a periphery of the user; information including at least one of the pulse, the blood pressure, and the body temperature of the user of the electronic device 71; information on a user's situation estimated by the processing portion in the electronic device 71; and a change over time in information on an eye (eyes) of the user of the electronic device 71.

The server 74 generates string information from the above data with use of the processing portion 78. When the string information is generated from the above data, an extremely large amount of arithmetic processing is performed. With this structure, the amount of arithmetic processing performed in the electronic device 71 and the electronic device 72 can be reduced, and a delay of the operation speeds of the electronic device 71 and the electronic device 72 can be inhibited.

The server 74 transmits the generated string information to the electronic device 72 through the network 73.

The electronic device 72 accepts the string information from the server 74 through the network 73 and displays the string information on the display portion in the electronic device 72.

Through the above steps, the user of the electronic device 72 can recognize a situation of the user of the electronic device 71 as string information. In other words, the user of the electronic device 72 can recognize a situation of the user of the electronic device 71, on the basis of information other than an image captured with the camera 75 provided for the electronic device 71, a sound obtained with a microphone provided for the electronic device 71, or the like. Thus, the user of the electronic device 72 can communicate closely with the user of the electronic device 71.

The above is the description of the structure examples of the electronic device and the display system.

Next, operation examples of the electronic device and the display system of one embodiment of the present invention will be described with reference to flow charts shown in FIG. 7 to FIG. 10.

Operation Example 1

Figure 7:
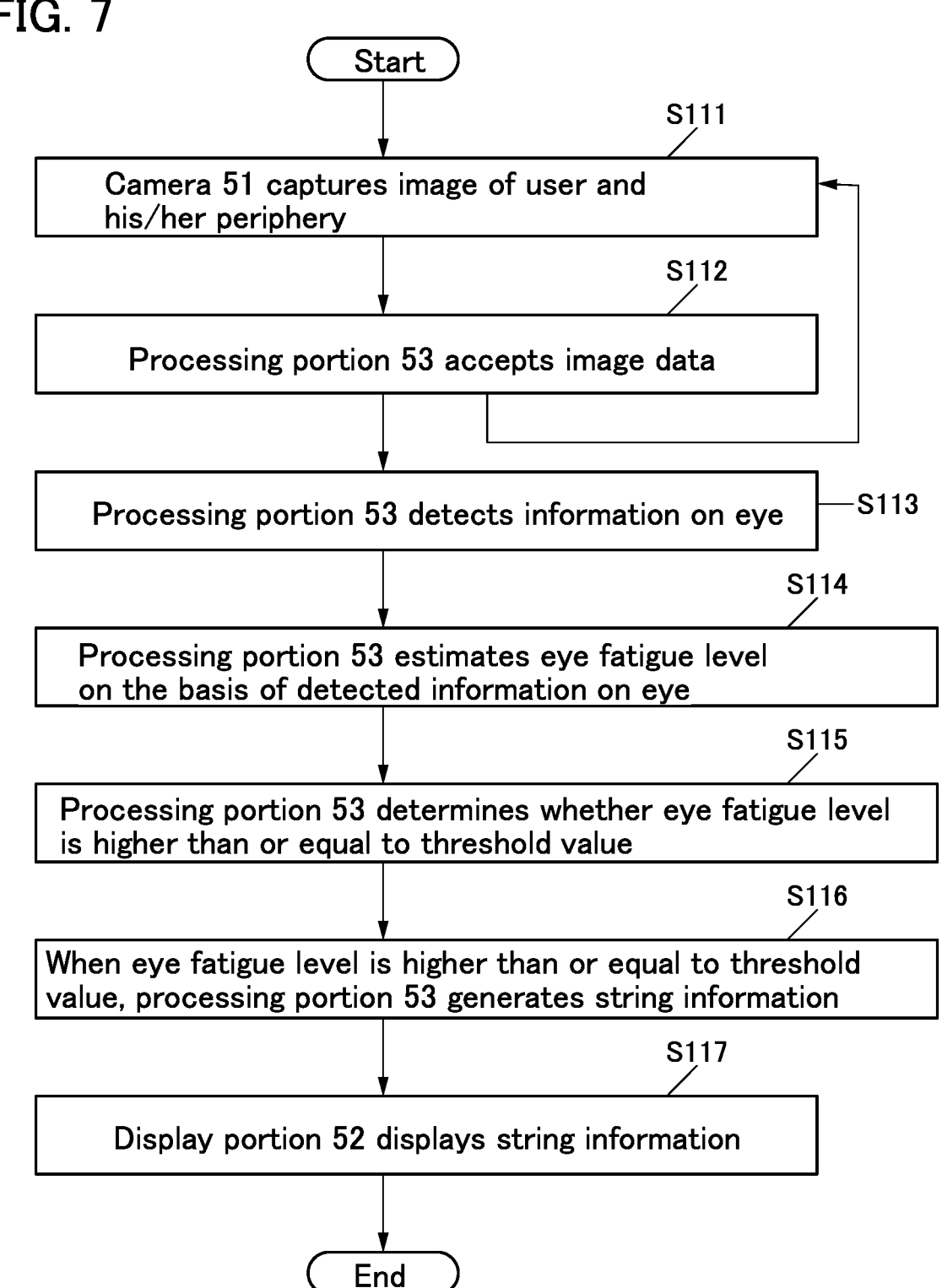
FIG. 7 is a flow chart illustrating an operation example of an electronic device.

First, an operation example in the case where a situation of a user is estimated with use of one electronic device, which is one embodiment of the present invention, is described below with reference to the flow chart shown in FIG. 7. The flow chart shown in FIG. 7 includes Step S111 to Step S117.

Note that this operation example is described with use of the electronic device 50 illustrated in FIG. 4A. The user's situation estimated by the electronic device is regarded as the level of user's eye fatigue.

First, in Step S111, the camera 51 captures an image of a user and his/her periphery, whereby image data is generated. The image data preferably includes an eye (eyes) of the user. Next, in Step S112, the processing portion 53 accepts the image data generated in the camera 51. Note that Step S111 and Step S112 are repeated. Through the repetition of Step S111 and Step S112, a plurality of pieces of image data including the user and his/her periphery are generated. Thus, the processing portion 53 accepts the plurality of pieces of image data.

In Step S113, the processing portion 53 detects information on the eye from the plurality of pieces of image data accepted in Step S112. The information on the eye includes at least one of the frequency of eye blinks, a time taken for one blink, the distance between an upper eyelid and a lower eyelid, the sight direction, and the area of a pupil. Next, in Step S114, the processing portion 53 estimates the level of eye fatigue on the basis of the detected information on the eyes. In Step S115, the processing portion 53 determines whether the level of eye fatigue is higher than or equal to a threshold value. When the level of the eye fatigue is determined to be higher than or equal to the threshold value, the processing portion 53 generates string information in Step S116. Then, in Step S117, the display portion 52 displays the generated string information. Note that in addition to displaying the string information on the display portion 52, the string information may be read aloud or an alarm may be sounded in Step S117.

Accordingly, the user can recognize his/her own information on the eye fatigue level or the like as the string information. Moreover, the user can rally his/her concentration on the remote meeting after being alerted.

Operation Example 2

Figure 8:
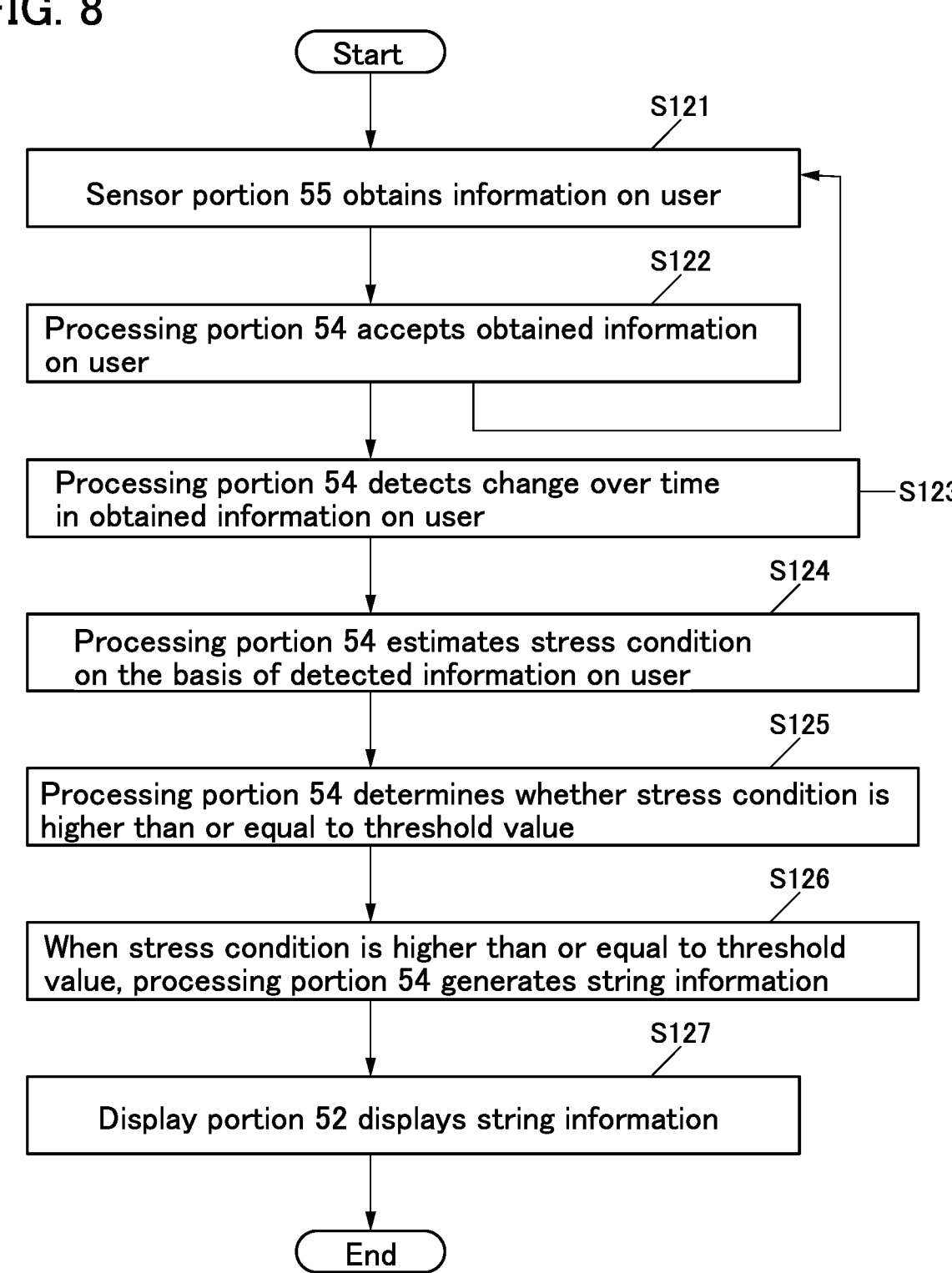
FIG. 8 is a flow chart illustrating an operation example of an electronic device.

An operation example in the case where a situation of a user is estimated with use of one electronic device, which is another embodiment of the present invention, is described below with reference to the flow chart shown in FIG. 8. The flow chart shown in FIG. 8 includes Step S121 to Step S127.

Note that this operation example is described with use of the electronic device 50 illustrated in FIG. 4D. The user's situation estimated by the electronic device is regarded as a stress situation.

In Step S121, the sensor portion 55 obtains user's information. Next, in Step S122, the processing portion 54 accepts the user's information obtained by the sensor portion 55. Note that Step S121 and Step S122 are repeated. Through the repetition of Step S121 and Step S122, the processing portion 54 accepts a plurality of pieces of user's information.

In Step S123, the processing portion 54 detects a change over time in obtained user's information. Next, in Step S124, the processing portion 54 estimates the stress situation on the basis of the detected change over time in user's information. Next, in Step S125, the processing portion 54 determines whether the stress situation is higher than or equal to a threshold value. When the stress situation is determined to be higher than or equal to a threshold value, the processing portion 54 generates string information in Step S126. Then, in Step S127, the display portion 52 displays the generated string information. Note that in addition to displaying the string information on the display portion 52, the string information may be read aloud or an alarm may be sounded in Step S127.

Accordingly, the user can recognize his/her own stress situation or the like as the string information. Moreover, the user can consider whether taking a break is needed after being alerted.

Operation Example 3

Figure 9:
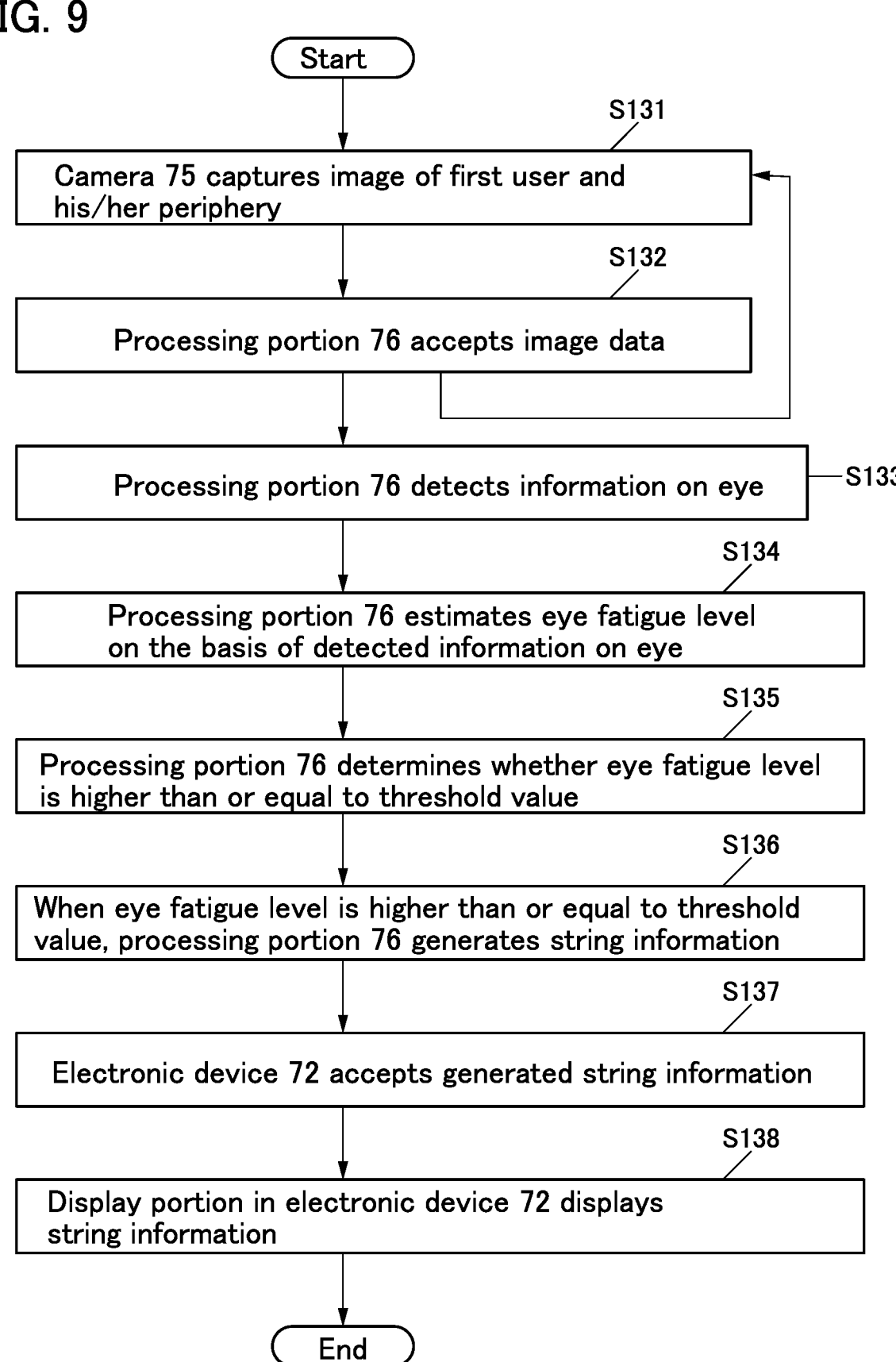
FIG. 9 is a flow chart illustrating an operation example of an electronic device.

An operation example in the case where a situation of a user is estimated with use of two electronic devices, which is another embodiment of the present invention, is described below with reference to the flow chart shown in FIG. 9. The flow chart shown in FIG. 9 includes Step S131 to Step S138.

Note that this operation example is described with use of the electronic device 71 and the electronic device 72 included in the display system 70 illustrated in FIG. 6A. A user of the electronic device 71 is referred to as a first user, and a user of the electronic device 72 is referred to as a second user. The user's situation estimated by the electronic device is regarded as the level of user's eye fatigue.

First, in Step S131, the camera 75 in the electronic device 71 captures an image of the first user and his/her periphery, whereby image data is generated. The image data preferably includes a eye of the first user. Next, in Step S132, the processing portion 76 in the electronic device 71 accepts the image data generated in the camera 75. Note that Step S131 and Step S132 are repeated. Through the repetition of Step S131 and Step S132, a plurality of pieces of image data including the first user and his/her periphery are generated. Thus, the processing portion in the electronic device 71 accepts a plurality of pieces of image data.

In Step S133, the processing portion 76 detects information on the eye from the plurality of pieces of image data accepted in Step S132. The information on the eye includes at least one of the frequency of eye blinks, the time taken for one blink, the distance between an upper eyelid and a lower eyelid, the sight direction, and the area of a pupil. Next, in Step S134, the processing portion 76 estimates the level of eye fatigue of the first user on the basis of the detected information on the eye. In Step S135, the processing portion 76 determines whether the level of eye fatigue of the first user is higher than or equal to a threshold value. When the level of the eye fatigue of the first user is determined to be higher than or equal to the threshold value, the processing portion 76 generates string information in Step S136. In Step S137, the electronic device 72 accepts the generated string information. Then, in Step S138, the display portion in the electronic device 72 displays the accepted string information. Note that in addition to displaying the string information on the display portion of the electronic device 72, the string information may be read aloud or an alarm may be sounded in Step S138.

Accordingly, the second user can recognize the level of eye fatigue of the first user as the string information. Note that when the user subjected to estimation is suffering from stress, the second user can give an advice in accordance with the stress situation of the first user.

Operation Example 4

Figure 10:
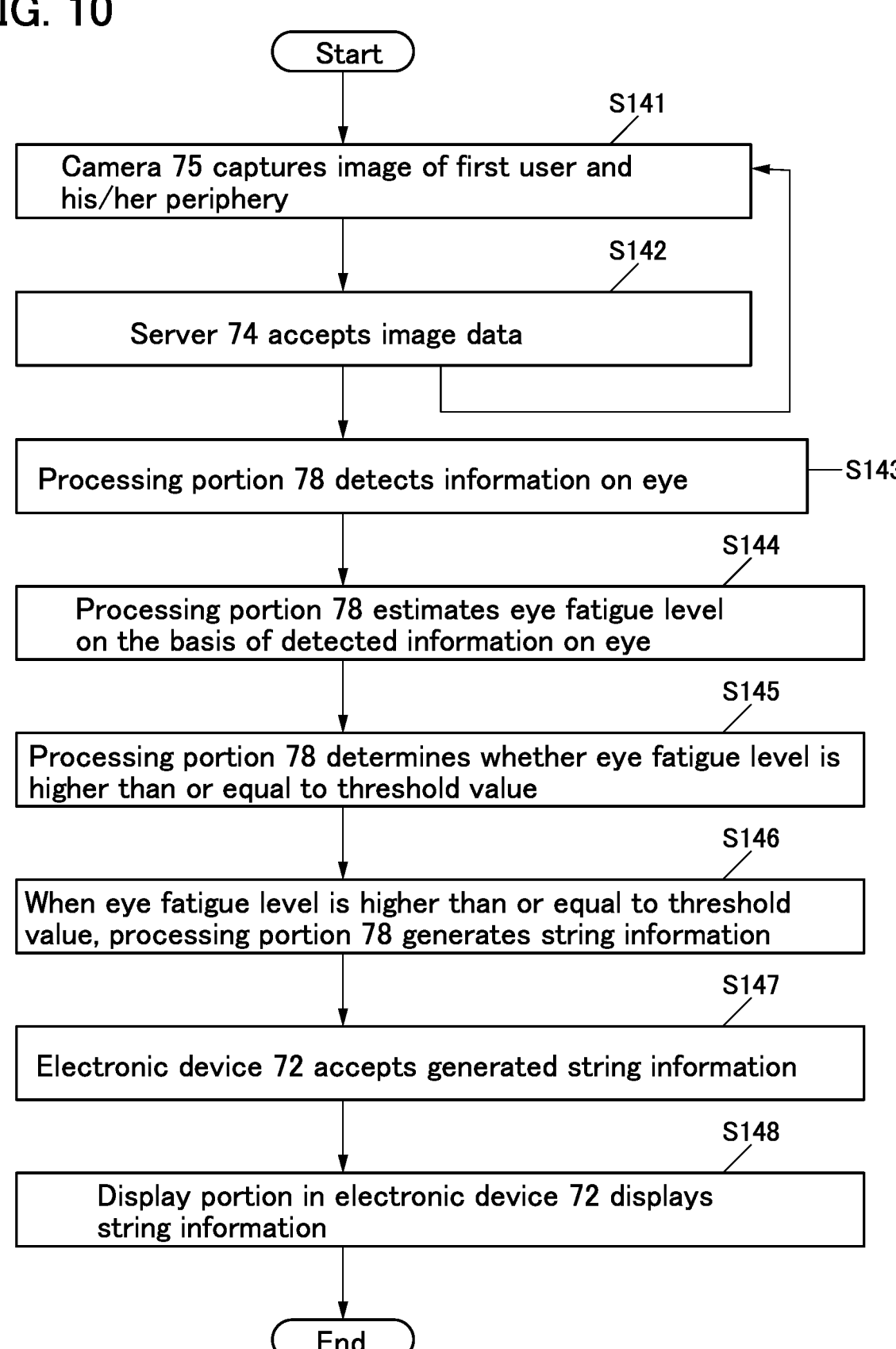
FIG. 10 is a flow chart illustrating an operation example of an electronic device.

An operation example in the case where a situation of a user is estimated with use of two electronic devices and a server, which is another embodiment of the present invention, is described below with reference to the flow chart shown in FIG. 10. The flow chart shown in FIG. 10 includes Step S141 to Step S148.

Note that this operation example is described with use of the electronic device 71, the electronic device 72, and the server 74 included in the display system 70 illustrated in FIG. 6B. A user of the electronic device 71 is referred to as a first user, and a user of the electronic device 72 is referred to as a second user. The user's situation estimated by the electronic device is regarded as the level of user's eye fatigue.

First, in Step S141, the camera 75 in the electronic device 71 captures an image of the first user and his/her periphery, whereby image data is generated. The image data preferably includes the eye of the first user. Next, in Step S142, the server 74 accepts the image data generated in the camera. Note that Step S141 and Step S142 are repeated. Through the repetition of Step S141 and Step S142, a plurality of pieces of image data including an image of the first user and his/her periphery are generated. Thus, the server 74 accepts the plurality of pieces of image data.

In Step S143, the processing portion 78 included in the server 74 detects information on the eye from the plurality of pieces of image data accepted in Step 142. The information on the eye includes at least one of the frequency of eye blinks, the time taken for one blink, the distance between an upper eyelid and a lower eyelid, the sight direction, and the area of a pupil. Next, in Step S144, the processing portion 78 estimates the level of eye fatigue of the first user on the basis of the detected information on the eye. In Step S145, the processing portion 78 determines whether the level of eye fatigue of the first user is higher than or equal to a threshold value. When the level of the eye fatigue of the first user is determined to be higher than or equal to the threshold value, the processing portion 78 generates string information in Step S146. In Step S147, the electronic device 72 accepts the generated string information. Then, in Step S148, the display portion in the electronic device 72 displays the accepted string information. Note that in addition to displaying the string information on the display portion of the electronic device 72, the string information may be read aloud or an alarm may be sounded in Step S148.

Accordingly, the second user can recognize the level of eye fatigue of the first user as the string information. Note that when the user subjected to estimation is suffering from stress, the second user can give an advice in accordance with the stress situation of the first user.

The above is the description of the operation examples of the electronic device and the display system of one embodiment of the present invention.

In the case where the string information where the user's situation is reflected is constantly displayed, Step S115, Step S125, Step S135, and Step S145 can be skipped.

<Method for Estimating User's Situation>

Next, a method for estimating a situation of a user is described with reference to FIG. 11A to FIG. 11C.

When the user looks at a display for a long time, the frequency of eye blinks may be decreased. When the user feels tired, the time taken for one blink might be prolonged or the distance between an upper eyelid and a lower eyelid might be decreased.

In addition, it is said that chronic fatigue leads to disorders of autonomic nerves. As the autonomic nerves, there are sympathetic nerves that become active at the time of body activity, during the daytime, and at the time of being nervous and parasympathetic nerves that become active at rest, at night, and at the time of being relaxed. When the sympathetic nerves become dominant, pupil dilation, heartbeat promotion, an increase in blood pressure, or the like occurs. In contrast, when the parasympathetic nerves become dominant, pupil contraction, heartbeat suppression, a decrease in blood pressure, or the like occurs.

When the balance of the autonomic nerves gets worse, hypothermia, a decrease in the number of blinks or the amount of tears, or the like is caused. In addition, maintaining slouching or a hunchbacked posture for a long time sometimes leads to disorders of autonomic nerves.

Accordingly, when the disorders or balance of autonomic nerves can be evaluated, the level of fatigue or stress can be evaluated objectively. In other words, a change over time in the frequency of eye blinks, the time taken for one blink, the distance between an upper eyelid and a lower eyelid, the sight direction, the pupil the pupil diameter or the area of a pupil), the heart beats or pulse, the blood pressure, the body temperature, the blinking, the posture, or the like is evaluated, whereby the level of fatigue or stress can be evaluated objectively.

In the display device and the display system of one embodiment of the present invention, the level of eye fatigue of a user, the fatigue level of the user, the stress situation, or the like can be estimated from information on the user. Note that the information on the user includes at least one of the frequency of eye blinks, the time taken for one blink, the distance between an upper eyelid and a lower eyelid, the sight direction, the area of a pupil, the pulse, the blood pressure, and the body temperature. The frequency of eye blinks, the time taken for one blink, the distance between an upper eyelid and a lower eyelid, the sight direction, the area of a pupil, or the like can be detected from the image data including the eye and a periphery thereof; thus, the user's eye and a periphery thereof are preferably included in image data in the display device and the display system of one embodiment of the present invention. Hence, the level of eye fatigue of the user, the fatigue level of the user, the stress situation, or the like can be estimated.

The image data including a user and his/her periphery can be captured with a camera provided for an electronic device and a display device of one embodiment of the present invention. A processing portion in the electronic device and the display system preferably has a function of processing of the image data. For example, by the processing, a region outside the eye is preferably removed from the image data. In other words, by the processing, preferably, a region including the eyes is clipped, and the image data is replaced with the clipped region including the eye. By the processing, the region (area) occupied by the eye with respect to the whole region (area) of the image data can be increased, which enables highly accurate estimation of the level of user's eye fatigue or user's sight direction. For this processing, a system using AI (Artificial Intelligence) can be employed.

For the estimation of a situation of a user, a learned model or an arithmetic circuit capable of arithmetic processing based on a neural network can be used. As the learned model, a neural network is preferably used, and a convolutional neural network is further preferably used. As the arithmetic circuit, an arithmetic circuit having a function of performing a product-sum operation described in Embodiment 2 is preferably used.

An example of a method for estimating a situation of user with use of a neural network is described with reference to FIG. 11A.

Figure 11A:
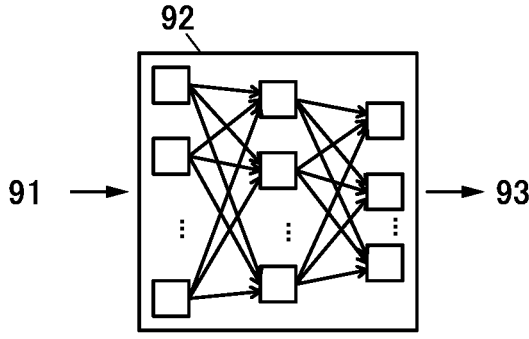
FIG. 11A and FIG. 11B each illustrate a method for estimating a user's situation.

As illustrated in FIG. 11A, input data 91 is input to a neural network 92. Output data 93 is output from the neural network 92. That is, the output data 93 includes a result of operation performed in the neural network 92.

Examples of the neural network 92 includes a learned model and an arithmetic circuit capable of arithmetic processing based on a neural network. The learned model is preferably generated by performing supervised learning on the neural network. The learning of the neural network is not limited to supervised learning and may be semi-supervised learning.

As the input data 91, image data including an examinee and his/her periphery is prepared. The image data preferably includes an eye (eyes) of the examinee. The number of examinees is preferably more than one. Note that a user whose situation is to be estimated may be included in the examinees. Then, the neural network 92 is made to learn so that the output data 93 becomes information on the situation of the examinee.

The above can be also described as follows: the input data is image data including an examinee and his/her periphery, and teacher data (also referred to label) makes the neural network 92 learn with use of a learning data set including information on a situation of the examinee. In other words, supervised learning is performed on the neural network 92, whereby a learned model can be generated.

When the above arithmetic circuit is used as the neural network 92, learning of the neural network 92 corresponds to optimization of weight data held in a cell in the arithmetic circuit.

Owing to the above learning, the image data including a user and his/her periphery is input as the input data 91 to the neural network 92, information on the situation of a user can be output as the output data 93 from the neural network 92.

Alternatively, as the input data 91, image data including an examinee and his/her periphery and features (a character, a gesture, and the like) of the examinee are prepared. The image data preferably includes an eye (eyes) of the examinee. The number of examinees is preferably more than one. Note that a user whose situation is to be estimated may be included in the examinees. Then, the neural network 92 is made to learn so that the output data 93 becomes information on the situation of the examinee.

Owing to the above learning, when the image data including a user and his/her periphery is input as the input data 91 to the neural network 92, information on a situation of the user that takes accounts for an individual difference can be output as the output data 93 from the neural network 92.

Alternatively, as the input data 91, information on an examinee is prepared. The information on an examinee includes at least one of the frequency of eye blinks, the time taken for one blink, the distance between an upper eyelid and a lower eyelid, the sight direction, the area of a pupil, the pulse, the blood pressure, and the body temperature. The number of examinees is preferably more than one. Note that a user whose situation is to be estimated may be included in the examinees. Then, the neural network 92 is made to learn so that the output data 93 becomes information on the situation of the examinee.

Owing to the above learning, when the information on a user is input as the input data 91 to the neural network 92, information on a situation of the user can be output as the output data 93 from the neural network 92.

Alternatively, as the input data 91, information on an examinee and features (a character, a gesture, and the like) of the examinee are prepared. The number of examinees is preferably more than one. Note that a user whose situation is to be estimated may be included in the examinees. Then, the neural network 92 is made to learn so that the output data 93 becomes information on the situation of the examinee.

With the above learning, when the information on an examinee is input as the input data 91 to the neural network 92, information on a situation of the user that takes accounts for an individual difference can be output as the output data 93 from the neural network 92.

A method for estimating a situation of a user with use of a neural network is not limited to the above. Another example of a method for estimating a situation of a user with use of a neural network is described with reference to FIG. 11B.

Figure 11B:
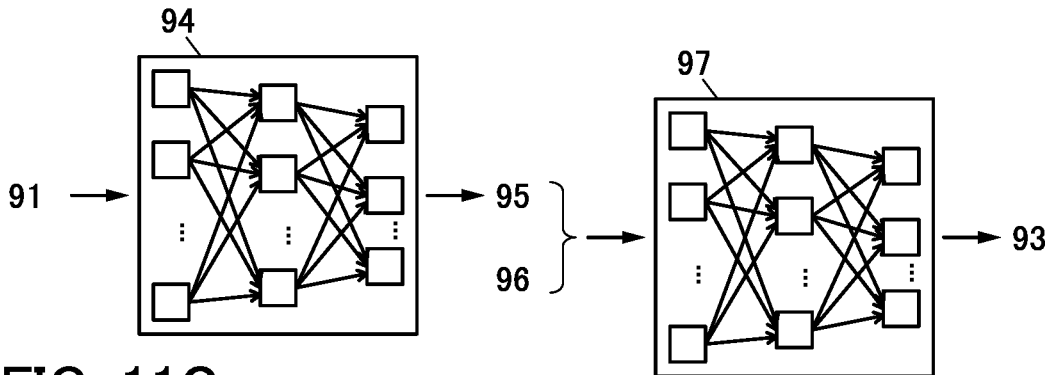

As illustrated in FIG. 11B, the input data 91 is input to a neural network 94. Intermediate data 95 is output from the neural network 94. That is, the intermediate data 95 includes a result of operation performed in the neural network 94.

Furthermore, the intermediate data 95 and input data 96 are input to a neural network 97. The output data 93 is output from the neural network 97. That is, the output data 93 includes a result of operation performed in the neural network 97.

Examples of each of the neural network 94 and the neural network 97 include a learned model and an arithmetic circuit capable of arithmetic processing based on a neural network. The learned model is preferably generated by performing supervised learning on the neural network. The learning of the neural network is not limited to supervised learning and may be semi-supervised learning.

As the input data 91, image data including an examinee and his/her periphery is prepared. The image data preferably includes an eye (eyes) of the examinee. The number of examinees is preferably more than one. Note that a user whose situation is to be estimated may be included in the examinees. Then, the neural network 94 is made to learn so that the intermediate data 95 becomes information on the situation of the examinee. The information on an examinee includes at least one of the frequency of eye blinks, the time taken for one blink, the distance between an upper eyelid and a lower eyelid, the sight direction, and the area of a pupil. Furthermore, the information on an examinee may include one or more of the pulse, the blood pressure, and the body temperature.

The above can be also described as follows: the input data is image data including an examinee and his/her periphery, and teacher data makes the neural network 94 learn with use of a learning data set including information on an examinee. In other words, supervised learning is performed on the neural network 94, whereby a learned model can be generated.

When the above arithmetic circuit is used as the neural network 94, learning of the neural network 94 corresponds to optimization of weight data held in a cell in the arithmetic circuit.

Owing to the above learning, when the image data including a user and his/her periphery is input as the input data 91 to the neural network 94, information on the user can be output as the intermediate data 95 from the neural network 94.

Alternatively, as the input data 96, features (a character, a gesture, and the like) of the examinee are prepared. Note that the examinee may be a user whose situation is to be estimated or a user other than the user whose situation is to be estimated. The number of examinees is preferably more than one. Note that a user whose situation is to be estimated may be included in the examinees. Then, the neural network

97 is made to learn so that the output data 93 becomes information on the situation of the examinee.

The above can be also described as follows: the input data is information on an examinee and features of the examinee, and teacher data makes the neural network 97 learn with use of a learning data set including information on a situation of the examinee. In other words, supervised learning is performed on the neural network 97, whereby a learned model can be generated.

When the above arithmetic circuit is used as the neural network 97, learning of the neural network 97 corresponds to optimization of weight data held in a cell in the arithmetic circuit.

Owing to the above learning, when the intermediate data 95 and the input data 96 are input to the neural network 97, the information on a situation of the examinee that takes accounts for an individual difference can be output as the output data 93 from the neural network 97.

With the structure illustrated in FIG. 11B, the information on a situation of a user that takes account for an individual difference can be output from image data including a user and his/her periphery and features (a character, a gesture, and the like) of the user.

The above is the description of the method for estimating a situation of a user with use of a neural network. The output data 93 is not limited to the information on a situation of the user. For example, string information may be used. In the string information, the information on a situation of the user is preferably reflected. In this case, the neural network 92 illustrated in FIG. 11A and the neural network 97 illustrated in FIG. 11B are preferably made to learn so that the output data 93 becomes the string information.

When the level of user's eye fatigue or user's sight direction is estimated as the situation of the user, a neural network is not necessarily used in some cases. For example, when the level of user's eye fatigue is estimated, fast Fourier transform may be performed to estimate a change over time in information on an eye (eyes) of the user. In this case, the level of user's eye fatigue can be estimated on the basis of the periodic change over time in the information; thus, the estimation can be performed with higher accuracy than the case where the level of user's eye fatigue is estimated on the basis of a threshold value.

Examples of estimation method of the level of user's eye fatigue or user's sight direction include a method using blinks and/or eyelid motion, a method using motion tracking of irises, and a scleral reflection method.

Figure 11C:
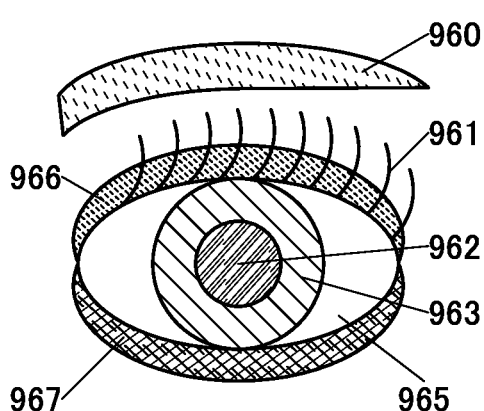
FIG. 11C is a schematic diagram illustrating a user's eye and a periphery thereof.

First, with reference to FIG. 11C, a method for detecting user's blinks and/or eyelid motion are/is described.

The electronic device is made to emit near-infrared light. The near-infrared light is incident on the user's eye or a periphery of the user's eye. The reflected near-infrared light enters the electronic device. Accordingly, the situation of an object can be detected.

Note that FIG. 11C is a schematic view illustrating a user's eye and the periphery of the user's eye. FIG. 11C illustrates a user's eyebrow 960, user's eyelids (an upper eyelid 966 and a lower eyelid 967), user's eyelashes 961, a user's pupil 962, a user's cornea 963, and a user's sclera 965. The electronic device has a function of detecting one or more selected from the user's eyebrow 960, the user's eyelids (the upper eyelid 966 and the lower eyelid 967), the user's eyelashes 961, the user's pupil 962, the user's cornea 963, and the user's sclera 965 that are illustrated in FIG. 11C.

For example, an electronic device of one embodiment of the present invention can sense the situation of the user's eye or the periphery of the user's eye illustrated in FIG. 11C. For example, when the user closes the eyelids (the upper eyelid 966 and the lower eyelid 967), the surface of the eyelids, i.e., the skin is irradiated with the near-infrared light. In addition, when the user open the eyelids, the surface of the user's eyeball is irradiated with the near-infrared light. Since the skin and the surface of an eyeball have different reflectances, the intensities of reflected near-infrared light are different. The intensity of reflected near-infrared light is monitored sequentially, whereby the electronic device can detect one or both of the number of blinks and the time taken for one blink.

When the user looks at a display for a long time, the number of blinks might be decreased. Furthermore, when the user feels fatigue, blink intervals might become longer and the time required for one blink might become longer.

The electronic device of one embodiment of the present invention can estimate the fatigue level of the user from one or both of the number of user's blinks and the time required for one blink. For example, when the number of use's blinks user per unit time is lower than or equal to a threshold value, the threshold value is preferably set such that the fatigue level of the user is determined to be high. Alternatively, for example, when the number of use's blinks per unit time is higher than or equal to a threshold value, the threshold value is preferably set such that the fatigue level of the user is determined to be high.

Next, a method using motion tracking of irises is described. When a boundary region between a cornea (e.g., the cornea 963 illustrated in FIG. 11C) and a sclera (e.g., the sclera 965 illustrated in FIG. 11C) is irradiated with an infrared circular spot, the ratio of a region covering the cornea to a region covering the sclera in an infrared spot irradiation range changes in accordance with the eyeball movement. Reflectance from the region covering the sclera is much higher than that from the region covering the cornea, and thus the amount of reflected light changes in accordance with the eyeball movement. By measuring this change, a direction in which the user sees can be detected.

Next, a scleral reflection method is described. The electronic device is made to emit near-infrared light. The user's eye is irradiated with the near-infrared light through an optical system. The reflected light is incident on the electronic device again through the optical system. Accordingly, a situation of a user can be detected. The user shifts his/her line of sight when watching a fast-moving object in a displayed video. When the line of sight is shifted, the eyeball moves. When the eyeball moves, the ratio of the region covering the cornea to the region covering the sclera that are irradiated with infrared light changes. Thus, by monitoring a reflected light component, the eyeball movement can be detected. That is, the electronic device of one embodiment of the present invention has an eye tracking function. A region the user watches carefully can be estimated by detecting the user's line of sight by eye tracking.

When a neural network is not used in estimating a situation of the user as described above, the electronic device preferably includes a light-emitting device emitting infrared light (including near-infrared light).

At least part of the structure examples, the drawings corresponding thereto, and the like described in this embodiment as examples can be combined with the other structure examples, the other drawings, and the like as appropriate.

At least part of this embodiment can be implemented in combination with the other embodiments described in this specification as appropriate.

Embodiment 2

An arithmetic circuit according to one embodiment of the present invention will be described. The arithmetic circuit can be used as an arithmetic circuit having a function of performing a product-sum operation, for example. The arithmetic circuit can be used for arithmetic processing of a neural network. Note that an arithmetic circuit having a function of performing a product-sum operation can be rephrased as an arithmetic circuit of a neural network. As the artificial neural network, a hierarchical neural network can be used, for example.

<Hierarchical Neural Network>

Figure 12A:
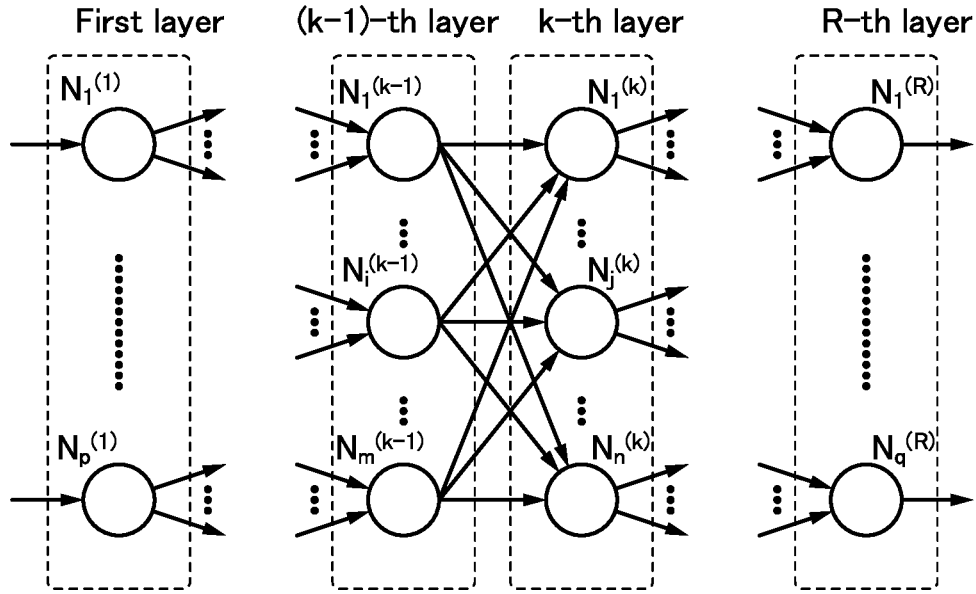
FIG. 12A and FIG. 12B are diagrams illustrating a structure example of a neural network.

A hierarchical neural network includes one input layer, one or a plurality of intermediate layers (hidden layers), and one output layer, for example, and is configured with a total of at least three layers. A hierarchical neural network ANN illustrated in FIG. 12A is one example, and the neural network ANN includes a first layer to an R-th layer (here, R can be an integer greater than or equal to 4). Specifically, the first layer corresponds to the input layer, the R-th layer corresponds to the output layer, and the other layers correspond to the intermediate layers. Note that FIG. 12A illustrates the (k−1)-th layer and the k-th layer (here, k is an integer greater than or equal to 3 and less than or equal to R−1) as the intermediate layers, and does not illustrate the other intermediate layers.

Each of the layers of the neural network ANN includes one or a plurality of neurons. In FIG. 12A, the first layer includes a neuron $N_1^{(1)}$ to a neuron $N_p^{(1)}$ (here, p is an integer greater than or equal to 1); the (k−1)-th layer includes a neuron $N_1^{(k-1)}$ to a neuron $N_m^{(k-1)}$ (here, m is an integer greater than or equal to 1); the k-th layer includes a neuron $N_1^{(k)}$ to a neuron $N_n^{(k)}$ (here, n is an integer greater than or equal to 1); and the R-th layer includes a neuron $N_1^{(R)}$ to a neuron $N_q^{(R)}$ (here, q is an integer greater than or equal to 1).

FIG. 12A illustrates a neuron $N_i^{(k-1)}$ (here, i is an integer greater than or equal to 1 and less than or equal to m) in the (k−1)-th layer and a neuron $N_j^{(k)}$ (here, j is an integer greater than or equal to 1 and less than or equal to n) in the k-th layer, in addition to the neuron $N_1^{(1)}$ the neuron $N_p^{(1)}$, the neuron $N_1^{(k-1)}$, the neuron $N_m^{(k-1)}$, the neuron $N_1^{(k)}$, the neuron $N_n^{(k)}$, the neuron $N_1^{(R)}$, and the neuron $N_q^{(R)}$ the other neurons are not illustrated.

Next, signal transmission from a neuron in one layer to a neuron in the subsequent layer and signals input to and output from the neurons are described. Note that description here is made focusing on the neuron $N_j^{(k)}$ in the k-th layer.

Figure 12B:
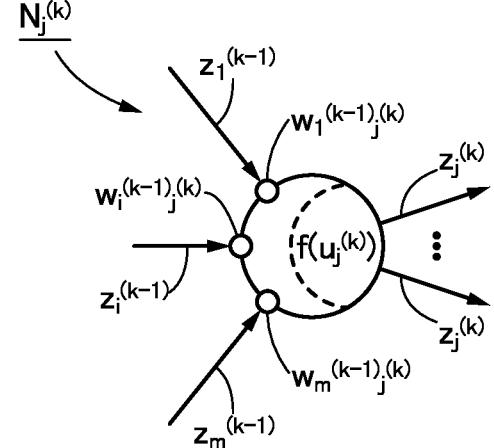

FIG. 12B illustrates the neuron $N_j^{(k)}$ in the k-th layer, signals input to the neuron $N_j^{(k)}$, and a signal output from the neuron $N_j^{(k)}$. FIG. 12B also illustrates weight data $w_1^{(k-1)\,(k)}_j$, $w_i^{(k-1)\,(k)}_j$, and $w_m^{(k-1)\,(k)}_j$ between the (k−1)th layer and the k-th layer, and an activation function $f(u_j^{(k)})$.

Specifically, $z_1^{(k-1)}$ to $z_m^{(k-1)}$ that are output signals from the neuron $N_1^{(k-1)}$ to the neuron $N_m^{(k-1)}$ in the (k−1)-th layer are output to the neuron $N_j^{(k)}$. Then, the neuron $N_j^{(k)}$ generates $z_j^{(k)}$ in accordance with $z_1^{(k-1)}$ to $z_m^{(k-1)}$, and outputs $z_j^{(k)}$ as the output signal to the neurons in the (k−1)-th layer (not illustrated).

<Structure Example 1 of Arithmetic Circuit>

Next, a structure example of an arithmetic circuit of one embodiment of the present invention will be described. The arithmetic circuit can be used for the processing portion 53 or the processing portion 54 described in the above embodiment.

Figure 13:
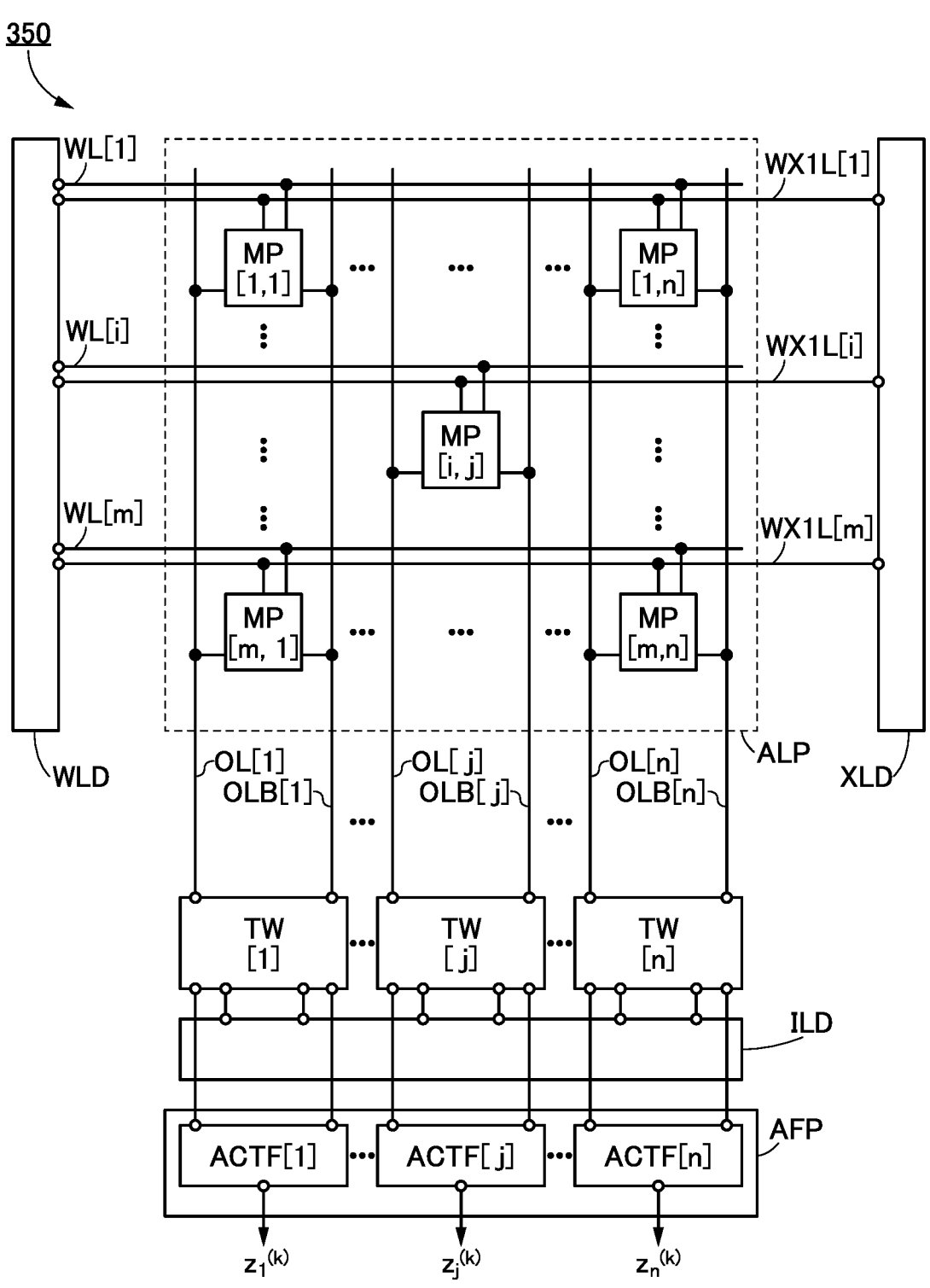
FIG. 13 is a diagram illustrating a structure example of an arithmetic circuit of a neural network structure.

An arithmetic circuit 350 in FIG. 13 includes an array portion ALP, a circuit ILD, a circuit WLD, a circuit XLD, a circuit AFP, and a circuit TW[1] to a circuit TW[n] (n is an integer greater than or equal to 1), for example.

The circuit ILD and the circuit AFP are electrically connected to a wiring OL[1] to a wiring OL[n] and a wiring OLB[1] to a wiring OLB[n] through the circuit TW[1] to the circuit TW[n].

The circuit TW[1] to the circuit TW[n] function as switching circuits. In the circuit TW[1] to the circuit TW[n], switching between inputting output signals of the wiring OL[1] to the wiring OL[n] and the wiring OLB [1] to the wiring OLB[n] to the circuit AFP and inputting output signals of the circuit ILD to the wiring OL[1] to the wiring OL[n] and the wiring OLB [1] to the wiring OLB[n] can be performed.

The circuit WLD is electrically connected to a wiring WL[1] to a wiring WL[m] and a wiring WX1L[1] to a wiring WX1L[m] (m is an integer greater than or equal to 1). The circuit XLD is electrically connected to the wiring WX1L[1] to the wiring WX1L[m].

The arithmetic circuit 350 illustrated in FIG. 13 includes the array portion ALP in which circuits MP are arranged in a matrix of m×n. Note that in FIG. 13, the circuit MP positioned in the i-th row and the j-th column (here, i is an integer greater than or equal to 1 and less than or equal to m, and j is an integer greater than or equal to 1 and less than or equal to n) is denoted by a circuit MP[i,j]. Note that FIG. 13 illustrates only the circuit MP[1,1], the circuit MP[1,*n*], the circuit MP[i,j], the circuit MP[m,1], and the circuit MP[m,n] and does not illustrate the other circuits MP.

The circuit MP[i,j] is electrically connected to a wiring WL[j], a wiring WX1L[i], a wiring OL[j], and a wiring OLB[j], for example.

The circuit MP[i,j] has a function of retaining a weight coefficient (also referred to as first data), for example. The weight coefficient is also referred to as a weighted value. Specifically, the circuit MP[i,j] holds information corresponding to a weight coefficient input from the wiring OL[j] and the wiring OLB[j].

The circuit ILD has a function of outputting information corresponding to the first data, which is a weight coefficient, to the wiring OL[1] to the wiring OL[n] and the wiring OLB[1] to the wiring OLB[n].

As the data corresponding to a weight coefficient, a potential, a resistance, a current value, or the like can be used, for example. In the case where a current value is used as information corresponding to a weight coefficient, a current to be input can be generated using a current output digital-to-analog converter (IDAC).

The circuit MP[i,j] has a function of outputting the product of an input value input from the wiring WX1L[i] (also referred to as second data) and the weight coefficient (first data). As a specific example, when the second data is input from the wiring WX1L[i], the circuit MP[i,j] outputs, to the wiring OL[j] and the wiring OLB[j], a current corresponding to the product of the first data and the second data. Note that although an example of the case where the wiring OL[j] and the wiring OLB[j] are provided is illustrated in FIG. 13, one embodiment of the present invention is not limited thereto. Only one of the wiring OL[j] and the wiring OLB[j] may be provided.

The circuit XLD has a function of supplying the second data, which is an input value, to the wiring WX1L[1] to the wiring WX1L[m].

Data corresponding to the input value can be, for example, a potential, a current value, or the like. In the case where a current value is used as information corresponding to an input value, a current to be input can be generated using a current output digital-to-analog converter.

Currents corresponding to the products of the first data and the second data output from the circuit MP[1,*j*] to the circuit MP[m,j] are added and the sum of the currents is output to the wiring OL[j] and the wiring OLB[j]. In this manner, the arithmetic circuit can perform a product-sum operation with the weight coefficients and the input values.

The circuit XLD and the circuit WLD each have a function of selecting the circuit MP to which information corresponding to the first data input from the circuit ILD is to be written. In the case where information is written to the circuit MP[i,1] to the circuit MP[i,n] positioned in the i-th row of the array portion ALP, for example, the circuit XLD supplies, to the wiring WX1L[i], a signal for turning on or off a first writing switching element included in each of the circuit MP[i,1] to the circuit MP[i,n], and supplies, to the other wiring WX1L, a potential for turning off the first writing switching element included in each of the circuits MP in rows other than the i-th row, for example. In addition, the circuit WLD supplies, to the wiring WL[i], a potential for turning on or off a second writing switching elements included in each of the circuits MP[i,1] to MP[i,n], and supplies, to the wirings WL, a potential for turning off the second writing switching element included in each of the circuits MP in rows other than the i-th row, for example.

The circuit AFP includes a circuit ACTF[1] to a circuit ACTF[n], for example. The circuit ACTF[j] is electrically connected to the wiring OL[j] and the wiring OLB[j] through the circuit TW[j] having a switching function, for example. The circuit ACTF[j] can generate a signal corresponding to information (e.g., a potential or a current value) according to the results of product-sum operations that are input from the wiring OL[j] and the wiring OLB[j] and output the signal as $z_j^{(k)}$. The circuit AFP can compare information (e.g., a potential or a current value) corresponding to the results of product-sum operations that are input from the wiring OL[1] to the wiring OL[n] and the wiring OLB[1] to the wiring OLB[n], generate signals corresponding to the comparison results, and output the signals as $z_1^{(k)}$ to $z_n^{(k)}$.

<Circuit MP>

Figure 14:
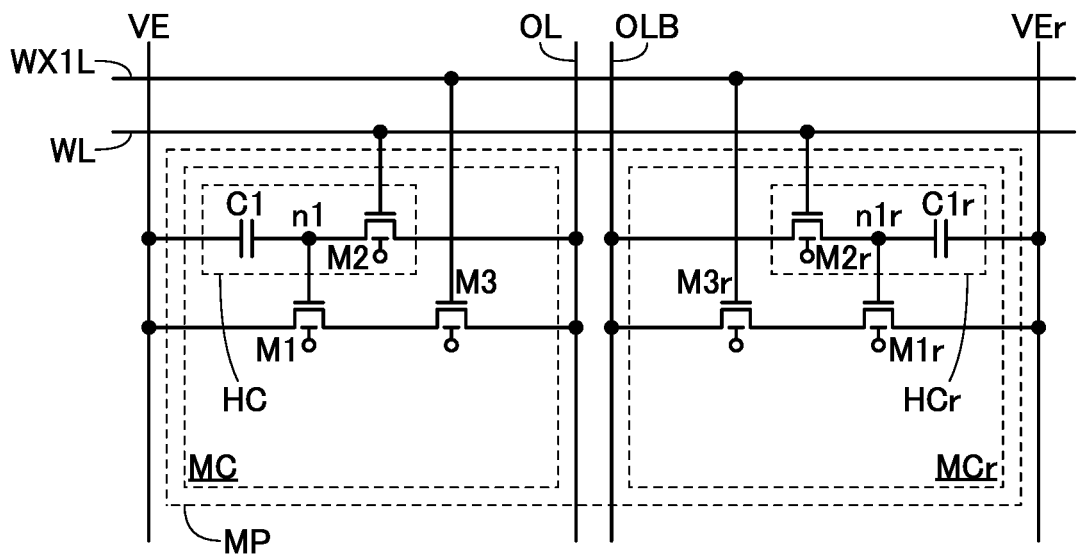
FIG. 14 is a diagram illustrating a structure example of an arithmetic circuit of a neural network structure.

Next, the circuit MP is described. FIG. 14 illustrates a circuit structure example that can be used for the circuit MP[i,j]. The circuit MP includes a circuit MC and a circuit MCr. The circuit MC includes a transistor M1 to a transistor M3 and a capacitor C1. Note that, for example, a holding portion HC includes the transistor M2 and the capacitor C1.

In the circuit MP in FIG. 14, the circuit MCr has substantially the same circuit configuration as the circuit MC. Thus, "r" is added to the reference numerals of the circuit elements and the like included in the circuit MCr to differentiate them from the circuit elements and the like included in the circuit MC.

The transistor M1 to the transistor M3 illustrated in FIG. 14 are each an n-channel transistor having a multi-gate structure including gates over and under a channel, and the transistor M1 to the transistor M3 each include a first gate and a second gate.

The arithmetic circuit 350 described in this embodiment does not depend on the connection structure of the back gate of a transistor. In the transistor M1 to the transistor M3 illustrated in FIG. 14, the back gate is illustrated and the connection structure of the back gate is not illustrated; however, a target to which the back gate is electrically connected can be determined at the design stage. For example, in a transistor including a back gate, a gate and the back gate may be electrically connected to each other to increase the on-state current of the transistor. In other words, the gate and the back gate of a transistor M2 may be electrically connected to each other, for example. Alternatively, for example, in a transistor including a back gate, a wiring electrically connected to an external circuit or the like may be provided and a potential may be supplied to the back gate of the transistor by the external circuit or the like to change the threshold voltage of the transistor or to reduce the off-state current of the transistor. Note that the same applies to a transistor described in other parts of the specification and a transistor illustrated in other drawings, not only to the transistors in FIG. 14.

Furthermore, unless otherwise specified, off-state current in this specification and the like refers to drain current of a transistor in an off state (also referred to as a non-conduction state or a cutoff state). Unless otherwise specified, an off state refers to, in an n-channel transistor, a state where voltage $V_{gs}$ between its gate and source is lower than the threshold voltage $V_{th}$ (in a p-channel transistor, higher than $V_{th}$).

The semiconductor device of one embodiment of the present invention does not depend on the structure of a transistor included in the semiconductor device. That is, transistors with a single gate structure may be used. It is also possible that some transistors have a structure including a back gate and the other transistors have a structure not including a back gate. Note that the same applies to a transistor described in other parts of the specification and a transistor illustrated in other drawings, not only to that in the circuit diagram illustrated in FIG. 14.

In this specification and the like, transistors with a variety of structures can be used as a transistor. Thus, there is no limitation on the type of transistors used. Examples of the transistor include a transistor including single crystal silicon and a transistor including a non-single-crystal semiconductor film typified by amorphous silicon, polycrystalline silicon, microcrystalline (also referred to as microcrystal, nanocrystal, or semi-amorphous) silicon, or the like. Alternatively, a thin film transistor (TFT) including a thin film of any of these semiconductors can be used, for example. The use of the TFT has various advantages. For example, since the TFT can be manufactured at a lower temperature than the case of using single crystal silicon, manufacturing costs can be reduced or a larger manufacturing apparatus can be used.

Note that as an example of a transistor, a transistor including a compound semiconductor (e.g., SiGe or GaAs), an oxide semiconductor, or the like can be used. A transistor including an oxide semiconductor in a channel formation region is sometimes referred to as an OS transistor. Alternatively, a thin film transistor including a thin film of such a compound semiconductor or oxide semiconductor can be used, for example. Note that such a compound semiconductor or oxide semiconductor can be used not only for a channel portion of the transistor but also for other applications. For example, such a compound semiconductor or oxide semiconductor can be used for a wiring, a resistor, a pixel electrode, or a light-transmitting electrode. Since such components can be deposited or formed at the same time as the transistor, the cost can be reduced.

As the oxide semiconductor, an oxide containing at least one of indium, an element M (as the element M, for example, one kind or a plurality of kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like can be given), and zinc may be used.

As another example, a transistor formed by an inkjet method or a printing method, or the like, can be used. The transistor can be manufactured at room temperature, manufactured at a low vacuum degree, or manufactured over a large substrate. Accordingly, the transistor can be manufactured without using a mask (reticle), so that the layout of the transistor can be easily changed. Alternatively, since the transistor can be manufactured without using a resist, the material cost is reduced, and the number of steps can be reduced. Alternatively, since a film can be formed only where needed, a material is not wasted as compared with a manufacturing method by which etching is performed after the film is formed over the entire surface; thus, the cost can be reduced.

As another example, a transistor containing an organic semiconductor or a carbon nanotube can be used. Thus, a transistor can be formed over a bendable substrate. A device using a transistor containing an organic semiconductor or a carbon nanotube can be highly resistant to impact.

In the circuit MP in FIG. 14, a first terminal of the transistor M1 is electrically connected to a wiring VE. A second terminal of the transistor M1 is electrically connected to a first terminal of the transistor M3. A gate of the transistor M1 is electrically connected to a first terminal of the capacitor C1 and a first terminal of the transistor M2. A second terminal of the capacitor C1 is electrically connected to the wiring VE. A second terminal of the transistor M2 is electrically connected to the wiring OL. A gate of the transistor M2 is electrically connected to the wiring WL. A second terminal of the transistor M3 is electrically connected to the wiring OL, and a gate of the transistor M3 is electrically connected to the wiring WX1L.

The connection configuration of the circuit MCr different from that of the circuit MC is described. A second terminal of a transistor M3r is electrically connected to not the wiring OL but the wiring OLB. A first terminal of a transistor M1r and a second terminal of a capacitor C1r are electrically connected to a wiring VEr.

Note that in the holding portion HC illustrated in FIG. 14, an electrical connection point of the gate of the transistor M1, the first terminal of the capacitor C1, and the first terminal of the transistor M2 is a node n1.

The holding portion HC has a function of holding a potential corresponding to a weight coefficient (first data). The potential is held in the holding portion HC included in the circuit MC in FIG. 14 in the following manner: when the transistor M2 and the transistor M3 are brought into an on state, a predetermined current value is input from the wiring OL to be written a potential corresponding to the current value to the capacitor C1, and then the transistor M2 is brought into an off state. Thus, the potential of the node n1 can be held as the potential corresponding to the weight coefficient (first data). At this time, current is input from the wiring OL and a potential having a level corresponding to the amount of current can be retained in the capacitor C1. Therefore, the input of the first data is less likely to be adversely affected by variations in current characteristics (e.g., threshold voltage) of the transistor M1.

The current input to the wiring OL can be input and generated using a current output digital-to-analog converter.

As the transistor M2, a transistor with a low off-state current is preferably used for a long-term retention of the potential of the node n1. As the transistor with a low off-state current, an OS transistor can be used, for example. Since an OS transistor includes an oxide semiconductor with a wide band gap in a channel formation region, the OS transistor can have a reduced off-state current.

Alternatively, a transistor including a back gate may be used as the transistor M2, and an off-state current may be reduced by applying a low-level potential to the back gate to shift the threshold voltage to the positive side.

Thus, an arithmetic circuit with high arithmetic operation accuracy is provided. Alternatively, an arithmetic circuit with high reliability is provided.

<Structure Example 2 of Arithmetic Circuit>

An arithmetic circuit MAC1 that performs a product-sum operation is described as another example. The arithmetic circuit MAC1 can be used for the processing portion 53 or the processing portion 54 described in the above embodiment.

Figure 15:
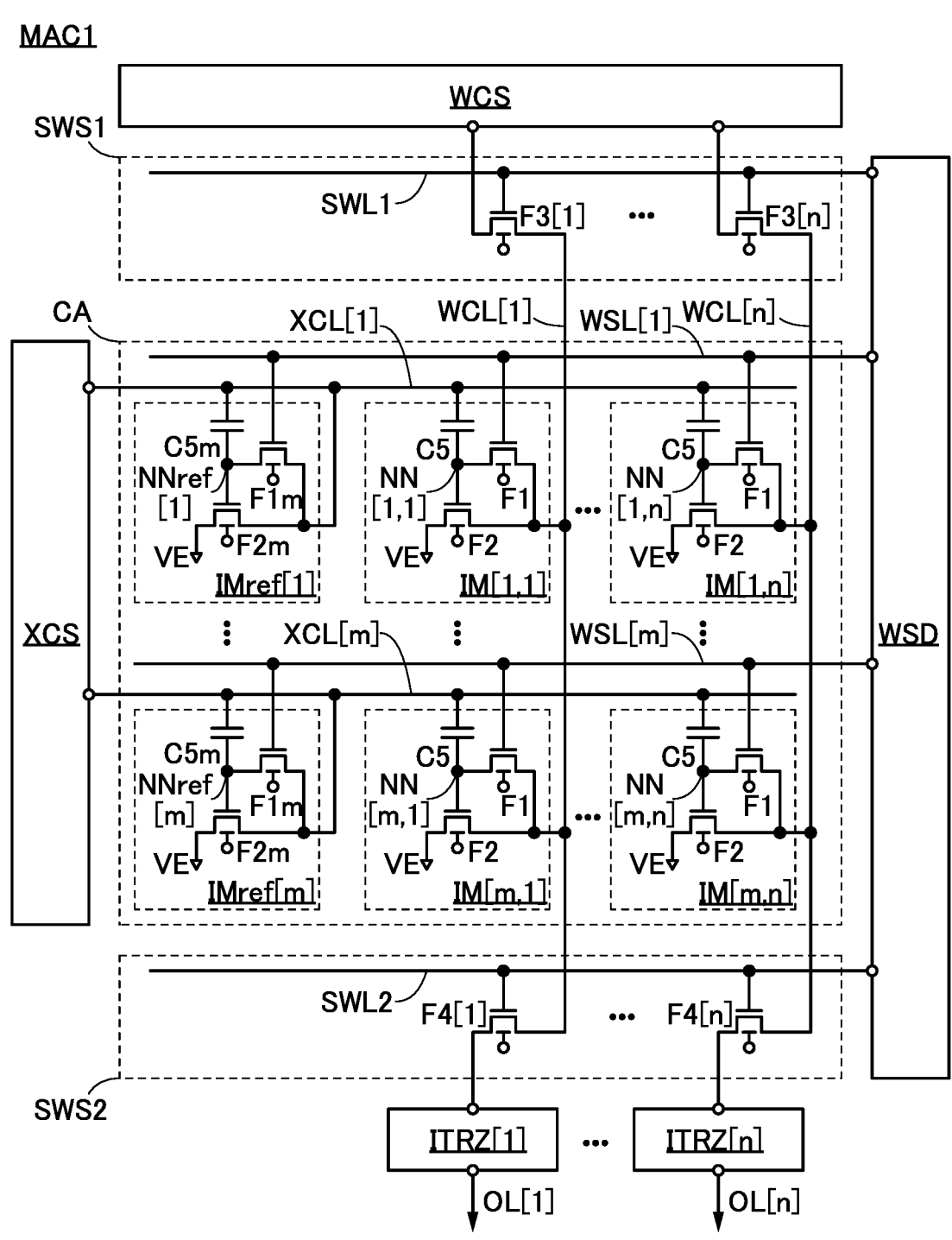
FIG. 15 is a diagram illustrating a structure example of an arithmetic circuit of a neural network structure.

FIG. 15 illustrates a structure example of an arithmetic circuit that performs product-sum operation of positive or "0" first data and positive or "0" second data. The arithmetic circuit MAC1 illustrated in FIG. 15 is a circuit that performs product-sum operation of the first data corresponding to a potential retained in each cell and the input second data, and performs arithmetic operation of an activation function with use of the product-sum operation result. Note that the first data and the second data can be analog data or multilevel data (discrete data), for example.

This arithmetic circuit, which also functions as a memory for retaining the first data, can be referred to as a memory. In particular, in the case where analog data is used as the first data, the arithmetic circuit can be referred to as an analog memory.

The arithmetic circuit MAC1 includes a circuit WCS, a circuit XCS, a circuit WSD, a circuit SWS1, a circuit SWS2, a cell array CA, and a converter circuit ITRZ[1] to a converter circuit ITRZ[n].

The cell array CA includes a cell IM[1,1] to a cell IM[m,n] (here, m is an integer greater than or equal to 1 and n is an integer greater than or equal to 1) and a cell IMref[1] to a cell IMref[m]. The cell IM[1,1] to the cell IM[m,n] have a function of retaining a potential corresponding to a current amount corresponding to the first data, and the cell IMref[1] to the cell IMref[m] have a function of supplying a potential corresponding to the second data necessary for performing a product-sum operation with the retained potential to the wiring XCL[1] to the wiring XCL[m].

In the cell array CA in FIG. 15, cells are arranged in a matrix of n+1 rows and m columns; however, the cell array CA may have a structure in which cells are arranged in a matrix of two or more rows and one or more columns.

The cell IM[1,1] to the cell IM[m,n] each include a transistor F1, a transistor F2, and a capacitor C5, and the cell IMref[1] to the cell IMref[m] each include a transistor F1$m$, a transistor F2$m$, and a capacitor CSm, for example.

It is particularly preferable that the sizes of the transistors F1 (e.g., the channel lengths, the channel widths, and the transistor structures) included in the cell IM[1,1] to the cell IM[m,n] be equal to each other, and the sizes of the transistors F2 included in the cell IM[1,1] to the cell IM[m,n] be equal to each other. It is preferable that the sizes of the transistors F1$m$ included in the cell IMref[1] to the cell IMref[m] be equal to each other, and the sizes of the transistors F2$m$ included in the cell IMref[1] to the cell IMref[m] be equal to each other. It is also preferable that the sizes of the transistor F1 and the transistor F1$m$ be equal to each other, and the sizes of the transistor F2 and the transistor F2$m$ be equal to each other.

Unless otherwise specified, the transistor F1 and the transistor F1$m$ in an on state may operate in a linear region in the end. In other words, the gate voltage, the source voltage, and the drain voltage of each of the above transistors may be appropriately biased to voltages in the range where the transistor operates in the linear region. However, one embodiment of the present invention is not limited thereto. For example, the transistor F1 and the transistor F1$m$ in an on state may operate in a saturation region or may operate both in a linear region and in a saturation region.

Unless otherwise specified, the transistor F2 and the transistor F2$m$ may operate in a subthreshold region (i.e., the gate-source voltage may be lower than the threshold voltage in the transistor F2 or the transistor F2$m$, further preferably, the drain current increases exponentially with respect to the gate-source voltage). In other words, the gate voltage, the source voltage, and the drain voltage of each of the above transistors may be appropriately biased to voltages in the range where the transistor operates in the subthreshold region. Thus, the transistor F2 and the transistor F2$m$ may operate such that the off-state current flows between the source and the drain.

The transistor F1 and/or the transistor F1$m$ are/is preferably an OS transistor described above, for example. In addition, it is further preferable that channel formation regions of the transistor F1 and/or the transistor F1$m$ be an oxide containing at least one of indium, the element M (as the element M, one or more kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like can be given for example), and zinc.

With the use of an OS transistor as the transistor F1 and/or the transistor F1$m$, the leakage current of the transistor F1 and/or the transistor F1$m$ can be suppressed, so that the power consumption of the arithmetic circuit can be reduced. Specifically, in the case where the transistor F1 and/or the transistor F1$m$ are/is in the non-conduction state, the amount of leakage current from a retention node to a write word line can be extremely small and thus the frequency of refresh operation for the potential of the retention node can be reduced. Accordingly, the power consumption of the arithmetic circuit can be reduced. An extremely low leakage current from the retention node to the write word line allows cells to retain the potential of the retention node for a long time, increasing the arithmetic operation accuracy of the arithmetic circuit.

The use of an OS transistor also as the transistor F2 and/or the transistor F2$m$ enables operation with a wide range of current in the subthreshold region, leading to a reduction in the current consumption. With use of an OS transistor also as the transistor F2 and/or the transistor F2$m$, the transistor F2 and/or the transistor F2$m$ can be manufactured concurrently with the transistor F1 and the transistor F1$m$; thus, the manufacturing process of the arithmetic circuit can sometimes be shortened. The transistor F2 and/or the transistor F2$m$ can be, other than an OS transistor, a transistor containing silicon in its channel formation region (hereinafter, referred to as a Si transistor). As the silicon, amorphous silicon (referred to as hydrogenated amorphous silicon in some cases), microcrystalline silicon, polycrystalline silicon, single crystal silicon, or the like can be used, for example.

When an arithmetic circuit or the like is highly integrated into a chip or the like, heat may be generated in the chip by circuit operation. This heat makes the temperature of a transistor rise to change the characteristics of the transistor, and the field-effect mobility thereof might change or the operation frequency thereof might decrease, for example. Since an OS transistor has a higher heat resistance than a Si transistor, a change in field-effect mobility and a decrease in operating frequency due to a temperature change do not easily occur. Even when having a high temperature, an OS transistor is likely to keep a property of the drain current increasing exponentially with respect to the gate-source voltage. With use of an OS transistor, a product-sum operation described below can thus be easily performed even in a high temperature environment. To form an arithmetic circuit highly resistant to heat due to operation, an OS transistor is preferably used as its transistor.

In each of the cell IM[1,1] to the cell IM[m,n], a first terminal of the transistor F1 is electrically connected to the gate of the transistor F2. A first terminal of the transistor F2 is electrically connected to the wiring VE. A first terminal of the capacitor C5 is electrically connected to the gate of the transistor F2.

In each of the cell IMref[1] to the cell IMref[m], a first terminal of the transistor F1$m$ is electrically connected to the gate of the transistor F2$m$. A first terminal of the transistor F2$m$ is electrically connected to the wiring VE. A first terminal of the capacitor C5$m$ is electrically connected to the gate of the transistor F2$m$.

The arithmetic circuit described in this embodiment does not depend on the polarity of transistors included in the arithmetic circuit. For example, the transistor F1 and the transistor F2 illustrated in FIG. 15 are n-channel transistors; however, some transistors or all transistors may be p-channel transistors.

The above-described examples of changes in the structure and polarity of the transistor are not limited to the transistor F1 and the transistor F2. For example, the same applies to the transistor F1$m$, the transistor F2$m$, a transistor F3[1] to a transistor F3[$n$] and a transistor F4[1] to a transistor F4[$n$], which are described later, a transistor described in other parts of the specification, and a transistor illustrated in other drawings.

The wiring VE functions as a wiring for flowing a current between the first terminal and a second terminal of the transistor F2 of each of the cell IM[1,1], the cell IM[m,1], the cell IM[1,$n$], and the cell IM[m,n] and a wiring for flowing a current between the first terminal and the second terminal of the transistor F2 of each of the cell IMref[1] and the cell IMref[m]. The wiring VE functions as a wiring for supplying a constant voltage, for example. The constant voltage can be, for example, a low-level potential, a ground potential, or the like.

In the cell IM[1,1], a second terminal of the transistor F1 is electrically connected to the wiring WCL[1], and the gate of the transistor F1 is electrically connected to the wiring WSL[1]. The second terminal of the transistor F2 is electrically connected to the wiring WCL[1], and a second terminal of the capacitor C5 is electrically connected to the wiring XCL[1]. In FIG. 15, in the cell IM[1,1], a connection portion of the first terminal of the transistor F1, the gate of the transistor F2, and the first terminal of the capacitor C5 is a node NN[1,1].

In the cell IM[m,1], the second terminal of the transistor F1 is electrically connected to the wiring WCL[1], and the gate of the transistor F1 is electrically connected to the wiring WSL[m]. The second terminal of the transistor F2 is electrically connected to the wiring WCL[1], and the second terminal of the capacitor C5 is electrically connected to the wiring XCL[m]. In FIG. 15, in the cell IM[m,1], a connection portion of the first terminal of the transistor F1, the gate of the transistor F2, and the first terminal of the capacitor C5 is a node NN[m,1].

In the cell IM[1,$n$], the second terminal of the transistor F1 is electrically connected to the wiring WCL[n], and the gate of the transistor F1 is electrically connected to the wiring WSL [ ]. The second terminal of the transistor F2 is electrically connected to the wiring WCL[n], and the second terminal of the capacitor C5 is electrically connected to the wiring XCL [ ]. In FIG. 15, in the cell IM[1,$n$], a connection portion of the first terminal of the transistor F1, the gate of the transistor F2, and the first terminal of the capacitor C5 is a node NN[1,$n$].

In the cell IM[m,n], the second terminal of the transistor F1 is electrically connected to the wiring WCL[n], and the gate of the transistor F1 is electrically connected to the wiring WSL[m]. The second terminal of the transistor F2 is electrically connected to the wiring WCL[n], and the second terminal of the capacitor C5 is electrically connected to the wiring XCL[m]. In FIG. 15, in the cell IM[m,n], a connection portion of the first terminal of the transistor F1, the gate of the transistor F2, and the first terminal of the capacitor C5 is a node NN[m,n].

In the cell IMref[1], a second terminal of the transistor F1$m$ is electrically connected to the wiring XCL[ ], and the gate of the transistor F1$m$ is electrically connected to the wiring WSL[ ]. The second terminal of the transistor F2$m$ is electrically connected to the wiring XCL[ ], and the second terminal of the capacitor C5 is electrically connected to the wiring XCL[ ]. In FIG. 15, in the cell IMref[1], a connection portion of a first terminal of the transistor F1$m$, a gate of the transistor F2$m$, and the first terminal of the capacitor C5 is a node NNref[1].

In the cell IMref[m], the second terminal of the transistor F1$m$ is electrically connected to the wiring XCL[m], and the gate of the transistor F1$m$ is electrically connected to the wiring WSL[m]. The second terminal of the transistor F2$m$ is electrically connected to the wiring XCL[m], and the second terminal of the capacitor C5 is electrically connected to the wiring XCL[m]. In FIG. 15, in the cell IMref[m], a connection portion of the first terminal of the transistor F1$m$, the gate of the transistor F2$m$, and the first terminal of the capacitor C5 is a node NNref[m].

The node NN[1,1], the node NN[m,1], the node NN[1,$n$], the node NN[m,n], the node NNref[1], and the node NNref [m] described above function as a retention node of the respective cells.

In the case where the transistor F1 is turned on in each of the cell IM[1,1] to the cell IM[m,n], for example, the transistor F2 is a diode-connected transistor. When a constant voltage supplied from the wiring VE is a ground potential (GND), the transistor F1 is turned on, and a current with a current amount/flows from the wiring WCL to the second terminal of the transistor F2, a potential of the gate of the transistor F2 (the node NN) is determined in accordance with the current amount I. Since the transistor F1 is in the on state, a potential of the second terminal of the transistor F2 is ideally equal to that of the gate of the transistor F2 (the node NN). Here, by turning off the transistor F1, the potential of the gate of the transistor F2 (the node NN) is retained. Accordingly, the transistor F2 can make the current with the current amount I corresponding to a ground potential of the first terminal of the transistor F2 and the potential of the gate of the transistor F2 (the node NN) flow between the source and the drain of the transistor F2. In this specification and the like, such an operation is expressed as "the transistor F2 is set (programmed) such that the amount of current flowing between the source and the drain of the transistor F2 is I".

The circuit SWS1 includes the transistor F3[1] to the transistor F3[n], for example. A first terminal of the transistor F3[1] is electrically connected to the wiring WCL[1], a second terminal of the transistor F3[1] is electrically connected to the circuit WCS, and a gate of the transistor F3[1] is electrically connected to a wiring SWL1. A first terminal of the transistor F3[n] is electrically connected to the wiring WCL[n], a second terminal of the transistor F3[n] is electrically connected to the circuit WCS, and a gate of the transistor F3[n] is electrically connected to the wiring SWL1.

As each of the transistor F3[1] to the transistor F3[n], for example, an OS transistor that can be used for the transistor F1 and/or the transistor F2 is preferable.

The circuit SWS1 functions as a circuit that establishes or breaks electrical continuity between the circuit WCS and each of the wiring WCL[1] to the wiring WCL[n].

The circuit SWS2 includes the transistor F4[1] to the transistor F4[n], for example. A first terminal of the transistor F4[1] is electrically connected to the wiring WCL[1], a second terminal of the transistor F4[1] is electrically connected to an input terminal of the converter circuit ITRZ[1], and a gate of the transistor F4[1] is electrically connected to a wiring SWL2. A first terminal of the transistor F4[n] is electrically connected to the wiring WCL[n], a second terminal of the transistor F4[n] is electrically connected to an input terminal of the converter circuit ITRZ[n], and a gate of the transistor F4[n] is electrically connected to the wiring SWL2.

As each of the transistor F4[1] to the transistor F4[n], for example, an OS transistor that can be used for the transistor F1 and/or the transistor F2 is preferable.

The circuit SWS2 functions as a circuit that establishes or breaks electrical continuity between the wiring WCL[1] and the converter circuit ITRZ[1] and between the wiring WCL[n] and the converter circuit ITRZ[n].

The circuit WCS has a function of supplying data that is to be retained in each cell of the cell array CA.

The circuit XCS is electrically connected to the wiring XCL[1] to the wiring XCL[m]. The circuit XCS has a function of flowing a current corresponding to reference data or a current corresponding to the second data to each of the cell IMref[1] to the cell IMref[m] included in the cell array CA.

The circuit WSD is electrically connected to the wiring WSL[1] to the wiring WSL[m]. The circuit WSD has a function of selecting a row of the cell array CA to which the first data is written, by supplying a predetermined signal to the wiring WSL[1] to the wiring WSL[m] at the time of writing the first data to the cell IM[1,1] to the cell IM[m,n].

The circuit WSD is electrically connected to the wiring SWL1 and the wiring SWL2, for example. The circuit WSD has a function of establishing electrical continuity and discontinuity between the circuit WCS and the cell array CA by supplying a predetermined signal to the wiring SWL1, and a function of establishing electrical continuity and discontinuity between the converter circuit ITRZ[1] to the converter circuit ITRZ[n] and the cell array CA by supplying a predetermined signal to the wiring SWL2.

The converter circuit ITRZ[1] to the converter circuit ITRZ[n] each include an input terminal and an output terminal, for example. An output terminal of the converter circuit ITRZ[1] is electrically connected to the wiring OL[1], and an output terminal of the converter circuit ITRZ[n] is electrically connected to the wiring OL[n], for example.

The converter circuit ITRZ[1] to the converter circuit ITRZ[n] each have a function of converting a current input to the input terminal into a voltage corresponding to the amount of the current and outputting the voltage from the output terminal. The voltage can be, for example, an analog voltage, a digital voltage, and the like. The converter circuit ITRZ[1] to the converter circuit ITRZ[n] may each include an arithmetic circuit of a function system. In that case, for example, the arithmetic circuit may perform arithmetic operation of a function with use of the converted voltage and may output the arithmetic operation results to the wiring OL[1] to the wiring OL[n].

In particular, in the case of performing arithmetic calculation of the hierarchical neural network, a sigmoid function, a tanh function, a softmax function, a ReLU function, a threshold function, or the like can be used as the above-described function.

As the circuit WCS illustrated in FIG. 15, a current output digital-to-analog converter can be used. As the XCS illustrated in FIG. 15, a current output digital-to-analog converter can be used.

At least part of the structure examples, the drawings corresponding thereto, and the like described in this embodiment as examples can be combined with the other structure examples, the other drawings, and the like as appropriate.

At least part of this embodiment can be implemented in combination with the other embodiments described in this specification as appropriate.

Embodiment 3

In this embodiment, a display device of one embodiment of the present invention will be described with reference to FIG. 16 to FIG. 25.

The display device in this embodiment can be a high-definition display device or a large-sized display device. Accordingly, the display device of this embodiment can be used for display portions of a digital camera, a digital video camera, a digital photo frame, a mobile phone, a portable game console, a portable information terminal, and an audio reproducing device, in addition to display portions of electronic devices with a relatively large screen, such as a television device, a desktop or laptop personal computer, a monitor of a computer or the like, digital signage, and a large game machine such as a pachinko machine.

[Display Device 100A]

Figure 16:
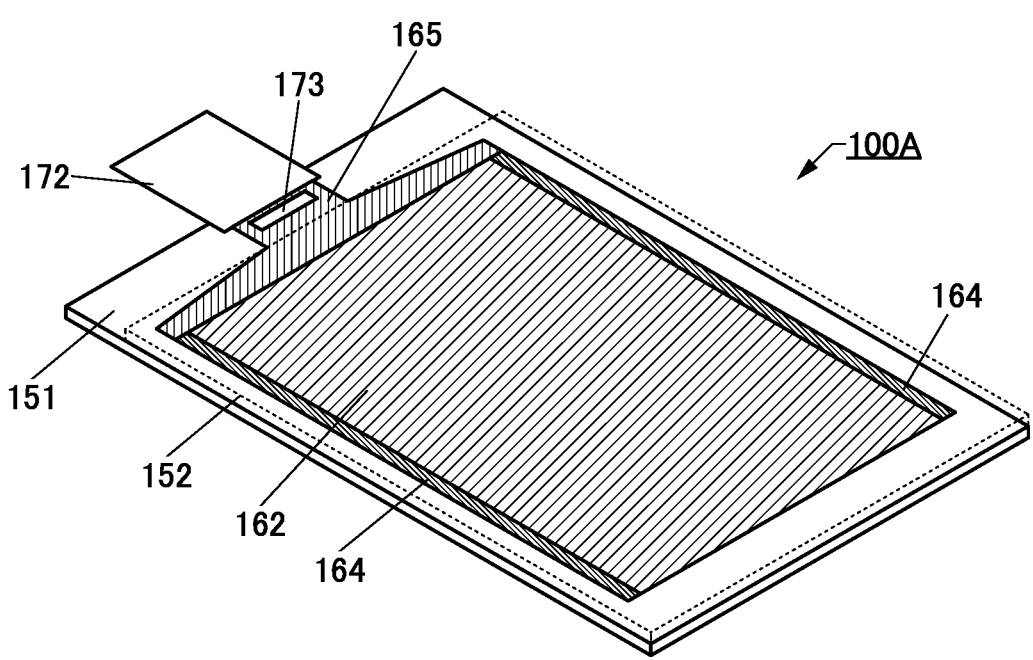
FIG. 16 is a perspective view illustrating an example of a display device.
Figures 17A, 17B, 17C:
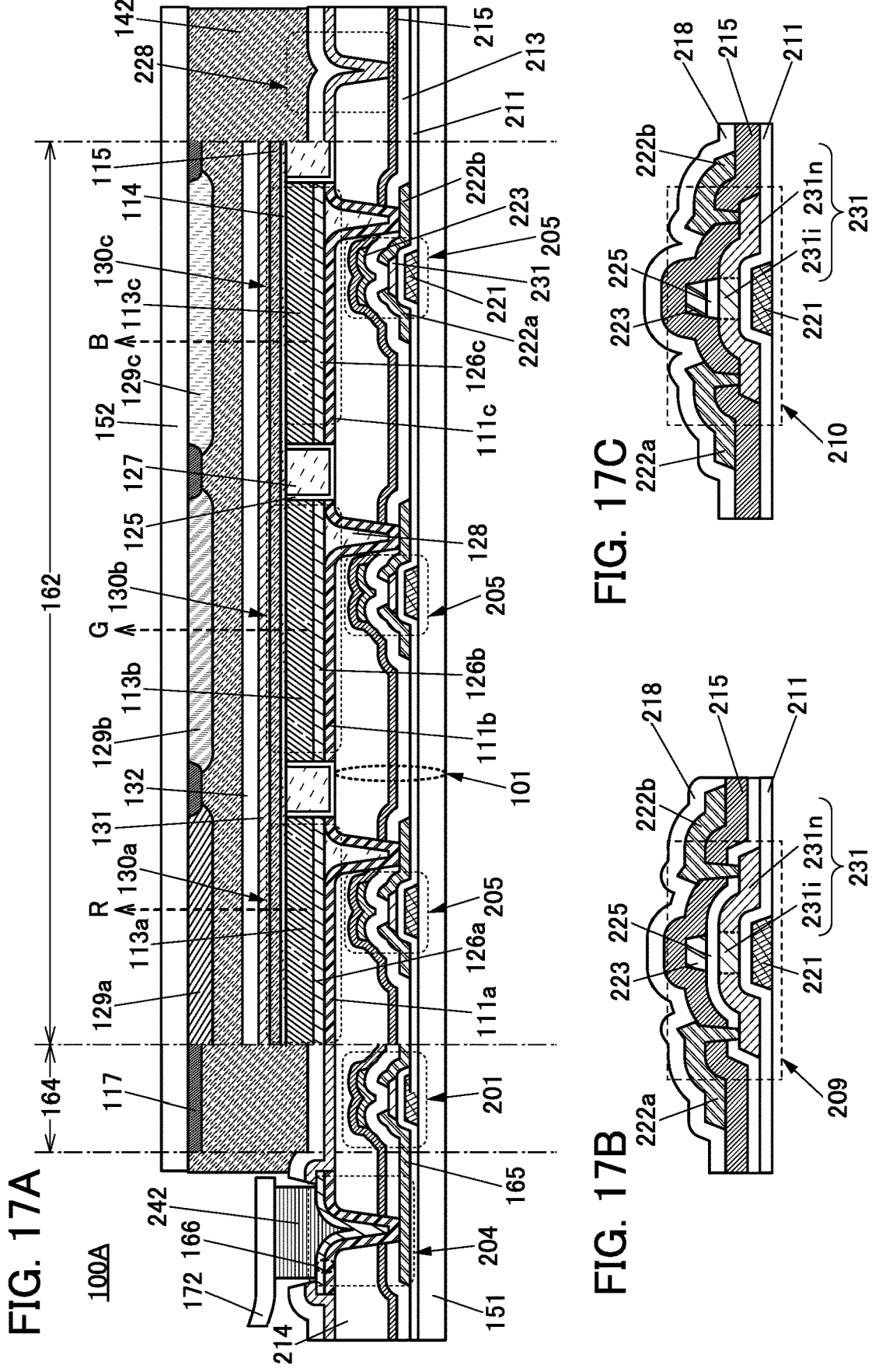
FIG. 17A is a cross-sectional view illustrating an example of a display device.
FIG. 17B and FIG. 17C are cross-sectional views each illustrating an example of a transistor.

FIG. 16 is a perspective view of a display device 100A, and FIG. 17A is a cross-sectional view of the display device 100A.

The display device 100A has a structure where a substrate 152 and a substrate 151 are bonded to each other. In FIG. 16, the substrate 152 is denoted by a dashed line.

The display device 100A includes a display portion 162, a circuit 164, a wiring 165, and the like. FIG. 16 illustrates an example in which an IC 173 and an FPC 172 are mounted on the display device 100A. Thus, the structure illustrated in FIG. 16 can be regarded as a display module including the display device 100A, the IC (integrated circuit), and the FPC.

As the circuit 164, a scan line driver circuit can be used, for example.

The wiring 165 has a function of supplying a signal and power to the display portion 162 and the circuit 164. The signal and power are input to the wiring 165 from the outside through the FPC 172 or from the IC 173.

FIG. 16 illustrates an example in which the IC 173 is provided over the substrate 151 by a COG (Chip On Glass) method, a COF (Chip On Film) method, or the like. An IC including a scan line driver circuit, a signal line driver circuit, or the like can be used as the IC 173, for example. Note that the display device 100A and the display module are not necessarily provided with an IC. The IC may be mounted on the FPC by a COF method or the like.

FIG. 17A illustrates an example of cross sections of part of a region including the FPC 172, part of the circuit 164, part of the display portion 162, and part of a region including an end portion of the display device 100A.

The display device 100A illustrated in FIG. 17A includes a transistor 201, a transistor 205, a light-emitting device 130a, a light-emitting device 130b, a light-emitting device 130c, a coloring layer 129a, a coloring layer 129b, a coloring layer 129c, and the like between the substrate 151 and the substrate 152. The light-emitting device 130a, the light-emitting device 130b, and the light-emitting device 130c emit white light. The coloring layer 129a, the coloring layer 129b, and the coloring layer 129c have functions of transmitting light of different colors from one another.

In the case where a pixel of the display device includes three kinds of subpixels including coloring layers transmitting different colors from each other, the three subpixels can be of three colors of red (R), green (G), and blue (B) or of three colors of yellow (Y), cyan (C), and magenta (M). In the case where four subpixels are included, the four subpixels can be of four colors of R, G, B, and white (W) or of four colors of R, G, B, and Y.

The display device of one embodiment of the present invention can have any of the following structures: a top-emission structure in which light is emitted in a direction opposite to the substrate where the light-emitting device is formed, a bottom-emission structure in which light is emitted toward the substrate where the light-emitting device is formed, and a dual-emission structure in which light is emitted toward both surfaces.

As each of the light-emitting device 130a, the light-emitting device 130b, and the light-emitting device 130c, an EL device such as an OLED (Organic Light Emitting Diode) or a QLED (Quantum-dot Light Emitting Diode) is preferably used. Examples of a light-emitting substance contained in the EL device include a substance exhibiting fluorescence (a fluorescent material), a substance exhibiting phosphorescence (a phosphorescent material), a substance exhibiting thermally activated delayed fluorescence (a thermally activated delayed fluorescence (TADF) material), and an inorganic compound (such as a quantum dot material). Note that as a TADF material, a material in which a singlet excited state and a triplet excited state are in a thermal equilibrium state may be used. Such a TADF material has a short emission lifetime (excitation lifetime), which allows inhibition of a decrease in efficiency in a high-luminance region of a light-emitting device.

The light-emitting device includes an EL layer between a pair of electrodes. In this specification and the like, in some cases, one of the pair of electrodes is referred to as a pixel electrode and the other of the pair of electrodes is referred to as a common electrode.

One of the pair of electrodes of the light-emitting device functions as an anode, and the other electrode functions as a cathode. The case where the pixel electrode functions as an anode and the common electrode functions as a cathode is described below as an example.

The light-emitting device 130a includes a pixel electrode 111a, a conductive layer 126a over the pixel electrode 111a, an island-shaped first layer 113a over the conductive layer 126a, a fifth layer 114 over the island-shaped first layer 113a, and a common electrode 115 over the fifth layer 114. In the light-emitting device 130a, the first layer 113a and the fifth layer 114 can be collectively referred to as an EL layer.

In addition, in this specification and the like, a device manufactured using a metal mask or an FMM (a fine metal mask or a high-definition metal mask) is sometimes referred to as a device having an MM (metal mask) structure. In this specification and the like, a device formed without using a metal mask or an FMM may be referred to as a device having an MML (metal maskless) structure.

Note that in this specification and the like, a structure in which light-emitting layers in light-emitting devices of respective colors (here, blue (B), green (G), and red (R)) are separately formed or the light-emitting layers are separately patterned is sometimes referred to as an SBS (Side By Side) structure. In this specification and the like, a light-emitting device capable of emitting white light may be referred to as a white-light-emitting device. Note that a combination of white-light-emitting devices with coloring layers (e.g., color filters) enables a full-color display device.

Structures of light-emitting devices can be classified roughly into a single structure and a tandem structure. A device having a single structure includes one light-emitting unit between a pair of electrodes, and the light-emitting unit preferably includes one or more light-emitting layers. To obtain white light emission by using two light-emitting layers, two light-emitting layers are selected such that the light-emitting layers emit light of complementary colors. For example, when emission color of a first light-emitting layer and emission color of a second light-emitting layer are complementary colors, the light-emitting device can be configured to emit white light as a whole. To obtain white light emission by using three or more light-emitting layers, the light-emitting device is configured to emit white light as a whole by combining emission colors of the three or more light-emitting layers.

A device having a tandem structure includes two or more light-emitting units between a pair of electrodes, and each light-emitting unit preferably includes one or more light-emitting layers. To obtain white light emission, the structure is made so that light from light-emitting layers of the plurality of light-emitting units can be combined to be white light. Note that a structure for obtaining white light emission is similar to a structure in the case of a single structure. In the device having a tandem structure, it is suitable that an intermediate layer such as a charge-generation layer is provided between a plurality of light-emitting units.

When the white-light-emitting device (having a single structure or a tandem structure) and a light-emitting device having an SBS structure are compared to each other, the light-emitting device having an SBS structure can have lower power consumption than the white-light-emitting device. To reduce power consumption, a light-emitting device having an SBS structure is preferably used. Meanwhile, the white-light-emitting device is preferable in terms of lower manufacturing cost or higher manufacturing yield because the manufacturing process of the white-light-emitting device is simpler than that of a light-emitting device having an SBS structure.

There is no particular limitation on the structure of the light-emitting device in this embodiment, and the light-emitting device can have a single structure or a tandem structure.

The light-emitting device 130*b* includes a pixel electrode 111*b*, a conductive layer 126*b* over the pixel electrode 111*b*, an island-shaped second layer 113*b* over the conductive layer 126*b*, the fifth layer 114 over the island-shaped second layer 113*b*, and the common electrode 115 over the fifth layer 114. In the light-emitting device 130*b*, the second layer 113*b* and the fifth layer 114 can be collectively referred to as an EL layer.

The light-emitting device 130*c* includes a pixel electrode 111*c*, a conductive layer 126*c* over the pixel electrode 111*c*, an island-shaped third layer 113*c* over the conductive layer 126*c*, the fifth layer 114 over the island-shaped third layer 113*c*, and the common electrode 115 over the fifth layer 114. In the light-emitting device 130*c*, the third layer 113*c* and the fifth layer 114 can be collectively referred to as an EL layer.

The light-emitting devices of the respective colors share the same film as the common electrode. The common electrode shared by the light-emitting devices of the respective colors is electrically connected to a conductive layer provided in a connection portion. Thus, the same potential is supplied to the common electrode included in the light-emitting devices of the respective colors.

A conductive film that transmits visible light is used for the electrode through which light is extracted, which is either the pixel electrode or the common electrode. A conductive film that reflects visible light is preferably used as the electrode through which light is not extracted.

As a material that forms the pair of electrodes (the pixel electrode and the common electrode) of the light-emitting device and the light-receiving device, a metal, an alloy, an electrically conductive compound, a mixture thereof, and the like can be used as appropriate. Specific examples include indium tin oxide (In—Sn oxide, also referred to as ITO), In—Si—Sn oxide (also referred to as ITSO), indium zinc oxide (In—Zn oxide), In—W—Zn oxide, an alloy containing aluminum (an aluminum alloy) such as an alloy of aluminum, nickel, and lanthanum (Al—Ni—La), and an alloy of silver, palladium, and copper (Ag—Pd—Cu, also referred to as APC). In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

The light-emitting devices preferably employ a microcavity structure. Therefore, one of the pair of electrodes of the light-emitting devices is preferably an electrode having properties of transmitting and reflecting visible light (a semi-transmissive and semi-reflective electrode), and the other is preferably an electrode having a property of reflecting visible light (a reflective electrode). When the light-emitting devices have a microcavity structure, light obtained from the light-emitting layers can be resonated between electrodes, whereby light emitted from the light-emitting devices can be intensified.

The transparent electrode has a light transmittance higher than or equal to 40%. For example, an electrode having a visible light (light with a wavelength greater than or equal to 400 nm and less than 750 nm) transmittance higher than or equal to 40% is preferably used in the light-emitting devices. The visible light reflectivity of the transflective electrode is higher than or equal to 10% and less than or equal to 95%, preferably higher than or equal to 30% and lower than or equal to 80%. The visible light reflectivity of the reflective electrode is higher than or equal to 40% and lower than or equal to 100%, preferably higher than or equal to 70% and lower than or equal to 100%. These electrodes preferably have a resistivity of $1 \times 10^{-2}$ $\Omega$cm or lower.

The first layer 113*a*, the second layer 113*b*, and the third layer 113*c* are each provided to have an island shape. The first layer 113*a*, the second layer 113*b*, and the third layer 113*c* each include a light-emitting layer. The first layer 113*a*, the second layer 113*b*, and the third layer 113*c* preferably include light-emitting layers that emit white light. Here, the island-shaped first layer 113*a*, the island-shaped second layer 113*b*, and the island-shaped third layer 113*c* preferably contain the same material. That is, the island-shaped first layer 113*a*, the island-shaped second layer 113*b*, and the island-shaped third layer 113*c* are preferably formed by patterning of a film deposited in the same step.

The light-emitting layer is a layer containing a light-emitting substance. The light-emitting layer can contain one or more kinds of light-emitting substances. As the light-emitting substance, a substance that exhibits an emission color of blue, violet, bluish violet, green, yellowish green, yellow, orange, red, or the like is appropriately used. As the light-emitting substance, a substance that emits near-infrared light can also be used.

Examples of the light-emitting substance include a fluorescent material, a phosphorescent material, a TADF material, and a quantum dot material.

Examples of the fluorescent material include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative.

Examples of the phosphorescent material include an organometallic complex (particularly an iridium complex) having a 4H-triazole skeleton, a 1H-triazole skeleton, an imidazole skeleton, a pyrimidine skeleton, a pyrazine skeleton, or a pyridine skeleton; an organometallic complex (particularly an iridium complex) having a phenylpyridine derivative including an electron-withdrawing group as a ligand; a platinum complex; and a rare earth metal complex.

The light-emitting layer may contain one or more kinds of organic compounds (e.g., a host material and an assist material) in addition to the light-emitting substance (a guest material). As one or more kinds of organic compounds, one or both of the hole-transport material and the electron-transport material can be used. Alternatively, as one or more kinds of organic compounds, a bipolar material or a TADF material may be used.

The light-emitting layer preferably includes, for example, a phosphorescent material and a combination of a hole-transport material and an electron-transport material that easily forms an exciplex. With such a structure, light emission can be efficiently obtained by ExTET (Exciplex-Triplet Energy Transfer), which is energy transfer from an exciplex to a light-emitting substance (a phosphorescent material). When a combination of materials is selected so as to form an exciplex that exhibits light emission whose wavelength overlaps with the wavelength of a lowest-energy-side absorption band of the light-emitting substance, energy can be transferred smoothly and light emission can be obtained efficiently. With this structure, high efficiency, low-voltage driving, and a long lifetime of the light-emitting device can be achieved at the same time.

In addition to the light-emitting layer, the first layer 113a, the second layer 113b, and the third layer 113c may further include a layer containing any of a substance with a high hole-injection property, a substance with a high hole-transport property, a hole-blocking material, a substance with a high electron-transport property, a substance with a high electron-injection property, an electron-blocking material, a substance with a bipolar property (a substance with a high electron-transport property and a high hole-transport property), and the like.

Either a low molecular compound or a high molecular compound can be used for the light-emitting device, and an inorganic compound may also be included. Each layer included in the light-emitting device can be formed by an evaporation method (including a vacuum evaporation method), a transfer method, a printing method, an inkjet method, a coating method, or the like.

For example, the first layer 113a, the second layer 113b, and the third layer 113c may each include one or more of a hole-injection layer, a hole-transport layer, a hole-blocking layer, an electron-blocking layer, an electron-transport layer, and an electron-injection layer.

In the EL layer, one or more of a hole-injection layer, a hole-transport layer, a hole-blocking layer (also referred to as a hole-inhibition layer in some cases), an electron-blocking layer (also referred to as an electron-inhibition layer in some cases), an electron-transport layer, and an electron-injection layer can be formed as a layer common to the light-emitting devices. For example, a carrier-injection layer (a hole-injection layer or an electron-injection layer) may be formed as the fifth layer 114. Note that all the layers in the EL layer may be separately formed for the respective colors. That is, the EL layer does not necessarily include a layer common to the light-emitting devices of the respective colors.

The first layer 113a, the second layer 113b, and the third layer 113c each preferably include a light-emitting layer and a carrier-transport layer over the light-emitting layer. Accordingly, the light-emitting layer is prevented from being exposed on the outermost surface in the process of manufacturing the display device 100, so that damage to the light-emitting layer can be reduced. As a result, the reliability of the light-emitting devices can be increased.

The hole-injection layer is a layer injecting holes from an anode to the hole-transport layer, and a layer containing a material with a high hole-injection property. As the material with a high hole-injection property, an aromatic amine compound and a composite material containing a hole-transport material and an acceptor material (an electron-accepting material), and the like can be given.

The hole-transport layer is a layer transporting holes, which are injected from the anode by the hole-injection layer, to the light-emitting layer. The hole-transport layer is a layer containing a hole-transport material. The hole-transport material preferably has a hole mobility of $1\times10^{-6}$ $cm^2/Vs$ or higher. Note that other substances can also be used as long as they have a property of transporting more holes than electrons. As the hole-transport material, materials having a high hole-transport property, such as a π-electron rich heteroaromatic compound (e.g., a carbazole derivative, a thiophene derivative, and a furan derivative) and an aromatic amine (a compound having an aromatic amine skeleton), are preferable.

The electron-transport layer is a layer transporting electrons, which are injected from a cathode by the electron-injection layer, to the light-emitting layer. The electron-transport layer is a layer containing an electron-transport material. As the electron-transport material, a substance having an electron mobility greater than or equal to $1\times10^{-6}$ $cm^2/Vs$ is preferable. Note that other substances can also be used as long as they have a property of transporting more electrons than holes. As the electron-transport material, it is possible to use a material having a high electron-transport property, such as a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, or a π-electron deficient heteroaromatic compound including a nitrogen-containing heteroaromatic compound.

The electron-transport layer may have a stacked-layer structure, and may include a hole-blocking layer, in contact with the light-emitting layer, which blocks holes moving from the anode side to the cathode side through the light-emitting layer.

The electron-injection layer is a layer injecting electrons from the cathode to the electron-transport layer, and a layer containing a material with a high electron-injection property. As the material with a high electron-injection property, an alkali metal, an alkaline earth metal, or a compound thereof can be used. As the material with a high electron-injection property, a composite material containing an electron-transport material and a donor material (an electron-donating material) can also be used.

As the electron-injection layer, for example, an alkali metal, an alkaline earth metal, or a compound thereof, such as lithium, cesium, ytterbium, lithium fluoride (LiF), cesium fluoride (CsF), calcium fluoride ($CaF_x$, $X_{is}$ a given number), 8-(quinolinolato)lithium (abbreviation: Liq), 2-(2-pyridyl) phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), lithium oxide ($LiO_x$), or cesium carbonate can be used. The electron-injection layer may have a stacked-layer structure of two or more layers. For example, it is possible to employ a structure where lithium fluoride is used for a first layer and ytterbium is used for a second layer as the stacked-layer structure.

Alternatively, an electron-transport material may be used for the electron-injection layer. For example, a compound having an unshared electron pair and having an electron deficient heteroaromatic ring can be used as the electron-transport material. Specifically, a compound having at least one of a pyridine ring, a diazine ring (a pyrimidine ring, a pyrazine ring, and a pyridazine ring), and a triazine ring can be used.

Note that the lowest unoccupied molecular orbital (LUMO) of the organic compound having an unshared electron pair is preferably greater than or equal to $-3.6$ eV and less than or equal to $-2.3$ eV. In general, the highest occupied molecular orbital (HOMO) level and the LUMO level of the organic compound can be estimated by cyclic voltammetry (CV), photoelectron spectroscopy, optical absorption spectroscopy, inverse photoelectron spectroscopy, or the like.

For example, 4,7-diphenyl-1,10-phenanthroline (abbreviation: BPhen), 2,9-bis(naphthalen-2-yl)-4,7-diphenyl-1,10-phenanthroline (abbreviation: NBPhen), diquinoxalino [2,3-a: 2',3'-c]phenazine (abbreviation: HATNA), 2,4,6-tris [3'-(pyridin-3-yl)biphenyl-3-yl]-1,3,5-triazine (abbreviation: TmPPPyTz), or the like can be used as the organic compound having an unshared electron pair. Note that NBPhen has a higher glass transition temperature (Tg) than BPhen and thus has high heat resistance.

In addition, in the case of manufacturing a light-emitting device having a tandem structure, an intermediate layer is provided between two light-emitting units. The intermediate layer has a function of injecting electrons into one of the two light-emitting units and injecting holes to the other when voltage is applied between the pair of electrodes.

For example, the intermediate layer can be suitably formed using a material that can be used for the electron-injection layer, such as lithium. Alternatively, as another example, the intermediate layer can be suitably formed using a material that can be used for the hole-injection layer. A layer containing a hole-transport material and an acceptor material (electron-accepting material) can be used as the intermediate layer. A layer containing an electron-transport material and a donor material can be used as the intermediate layer. Forming the intermediate layer including such a layer can suppress an increase in the driving voltage that would be caused by stacking light-emitting units.

The conductive layer 126a, the conductive layer 126b, and the conductive layer 126c each function as an optical adjustment layer. Note that the conductive layer 126a, the conductive layer 126b, and the conductive layer 126c are not necessarily provided in some cases. Side surfaces of the pixel electrode 111a, the pixel electrode 111b, the pixel electrode 111c, the conductive layer 126a, the conductive layer 126b, the conductive layer 126c, the first layer 113a, the second layer 113b, and the third layer 113c are covered with the insulating layer 125 and an insulating layer 127. Thus, the fifth layer 114 (or the common electrode 115) can be prevented from being in contact with the side surfaces of the pixel electrode 111a, the pixel electrode 111b, the pixel electrode 111c the first layer 113a, the second layer 113b, and the third layer 113c, whereby a short circuit of the light-emitting device can be prevented.

The insulating layer 125 can be an insulating layer containing an inorganic material. As the insulating layer 125, an inorganic insulating film such as an oxide insulating film, a nitride insulating film, an oxynitride insulating film, or a nitride oxide insulating film can be used, for example. The insulating layer 125 may have either a single-layer structure or a stacked-layer structure. Examples of the oxide insulating film include a silicon oxide film, an aluminum oxide film, a magnesium oxide film, an indium gallium zinc oxide film, a gallium oxide film, a germanium oxide film, an yttrium oxide film, a zirconium oxide film, a lanthanum oxide film, a neodymium oxide film, a hafnium oxide film, and a tantalum oxide film. Examples of the nitride insulating film include a silicon nitride film and an aluminum nitride film. Examples of the oxynitride insulating film include a silicon oxynitride film, an aluminum oxynitride film, and the like. Examples of the nitride oxide insulating film include a silicon nitride oxide film, an aluminum nitride oxide film, and the like. In particular, an aluminum oxide film is preferable because it has high selectivity with respect to the EL layer in etching and has a function of protecting the EL layer during formation of the insulating layer 127 described later. In particular, when an inorganic insulating film such as an aluminum oxide film, a hafnium oxide film, or a silicon oxide film that is formed by an atomic layer deposition (ALD) method is employed for the insulating layer 125, it is possible to form the insulating layer 125 that has few pinholes and an excellent function of protecting the EL layer.

Note that in this specification and the like, an oxynitride refers to a material that contains more oxygen than nitrogen in its composition, and a nitride oxide refers to a material that contains more nitrogen than oxygen in its composition. For example, in the case where silicon oxynitride is described, it refers to a material that contains more oxygen than nitrogen in its composition. In the case where silicon nitride oxide is described, it refers to a material that contains more nitrogen than oxygen in its composition.

The insulating layer 125 can be deposited by a sputtering method, a chemical vapor deposition (CVD) method, a pulsed laser deposition (PLD) method, an ALD method, or the like. The insulating layer 125 is preferably formed by an ALD method achieving good coverage.

The insulating layer 127 provided over the insulating layer 125 has a function of planarizing the depression portion in the insulating layer 125 that is formed between the adjacent light-emitting devices. In other words, the insulating layer 127 brings an effect of improving the planarity of a surface where the common electrode 115 is formed. An insulating layer containing an organic material can be suitably used as the insulating layer 127. For example, the insulating layer 127 can be formed using an acrylic resin, a polyimide resin, an epoxy resin, an imide resin, a polyamide resin, a polyimide-amide resin, a silicone resin, a siloxane resin, a benzocyclobutene-based resin, a phenol resin, precursors of these resins, or the like. The insulating layer 127 may be formed using an organic material such as polyvinyl alcohol (PVA), polyvinyl butyral, polyvinylpyrrolidone, polyethylene glycol, polyglycerin, pullulan, water-soluble cellulose, or an alcohol-soluble polyamide resin. Moreover, the insulating layer 127 can be formed using a photosensitive resin. A photoresist may be used for the photosensitive resin. As the photosensitive resin, a positive photosensitive material or a negative photosensitive material can be used.

The difference between the height of the top surface of the insulating layer 127 and the height of the top surface of one of the first layer 113a, the second layer 113b, and the third layer 113c is preferably less than or equal to 0.5 times, further preferably less than or equal to 0.3 times the thickness of the insulating layer 127, for example. As another example, the insulating layer 127 may be provided so that the height of the top surface of one of the first layer 113a, the second layer 113b, and the third layer 113c is greater than the height of the top surface of the insulating layer 127. As another example, the insulating layer 127 may be provided so that the level of the top surface of the insulating layer 127 is greater than the level of the top surface of the light-emitting layer included in the first layer 113a, the second layer 113b, or the third layer 113c.

The fifth layer 114 is formed over the first layer 113a, the second layer 113b, the third layer 113c, the insulating layer 125, and the insulating layer 127. The common electrode 115 is provided over the fifth layer 114. A protective layer 131 is provided over the light-emitting device 130a, the light-emitting device 130b, and the light-emitting device 130c. The protective layer 132 is provided over the protective layer 131. Providing the protective layers 131 and 132 can improve the reliability of the light-emitting devices.

There is no limitation on the conductivity of the protective layers 131 and 132. As the protective layers 131 and 132, at least one type of insulating films, semiconductor films, and conductive films can be used.

When the protective layers 131 and 132 include an inorganic film, it is possible to inhibit degradation of the light-emitting devices by preventing oxidation of the common electrode 115 or inhibiting entry of impurities (moisture, oxygen, and the like) into the light-emitting devices 130*a*, 130*b*, and 130*c*, for example; thus, the reliability of the display device can be increased.

As the protective layers 131 and 132, an inorganic insulating film such as an oxide insulating film, a nitride insulating film, an oxynitride insulating film, or a nitride oxide insulating film can be used, for example. Examples of the oxide insulating film include a silicon oxide film, an aluminum oxide film, a gallium oxide film, a germanium oxide film, an yttrium oxide film, a zirconium oxide film, a lanthanum oxide film, a neodymium oxide film, a hafnium oxide film, and a tantalum oxide film. Examples of the nitride insulating film include a silicon nitride film and an aluminum nitride film. Examples of the oxynitride insulating film include a silicon oxynitride film, an aluminum oxynitride film, and the like. Examples of the nitride oxide insulating film include a silicon nitride oxide film, an aluminum nitride oxide film, and the like.

Each of the protective layers 131 and 132 preferably includes a nitride insulating film or a nitride oxide insulating film, and further preferably includes a nitride insulating film.

As the protective layers 131 and 132, an inorganic film containing In—Sn oxide (also referred to as ITO), In—Zn oxide, Ga—Zn oxide, Al—Zn oxide, indium gallium zinc oxide (In—Ga—Zn oxide, also referred to as IGZO), or the like can also be used. The inorganic film preferably has high resistance, specifically, higher resistance than the common electrode 115. The inorganic film may further contain nitrogen.

When light emitted from the light-emitting device is extracted through the protective layers 131 and 132, the protective layers 131 and 132 preferably have a high visible-light-transmitting property. For example, ITO, IGZO, and aluminum oxide are preferable because they are inorganic materials having a high visible-light-transmitting property.

The protective layers 131 and 132 can have, for example, a stacked-layer structure of an aluminum oxide film and a silicon nitride film over the aluminum oxide film, or a stacked-layer structure of an aluminum oxide film and an IGZO film over the aluminum oxide film. Such a stacked-layer structure can inhibit entry of impurities (e.g., water and oxygen) into the EL layers.

Furthermore, the protective layers 131 and 132 may include an organic film. For example, the protective layer 132 may include both an organic film and an inorganic film.

The protective layer 131 and the protective layer 132 may be formed by different deposition methods. Specifically, the protective layer 131 and the protective layer 132 may be formed by an ALD method and a sputtering method, respectively.

The coloring layer 129*a*, the coloring layer 129*b*, and the coloring layer 129*c* are provided over the protective layer 131. The coloring layer 129*a* includes a region overlapping with the light-emitting device 130*a*, the coloring layer 129*b* includes a region overlapping with the light-emitting device 130*b*, and the coloring layer 129*c* includes a region overlapping with the light-emitting device 130*c*. The coloring layers 129*a*, 129*b*, and 129*c* each include a region overlapping with at least the light-emitting layer included in the corresponding light-emitting device.

The coloring layer 129*a*, the coloring layer 129*b*, and the coloring layer 129*c* have functions of transmitting light of different colors from one another. For example, the coloring layer 129*a* has a function of transmitting red light, the coloring layer 129*b* has a function of transmitting green light, and the coloring layer 129*c* has a function of transmitting blue light. Thus, the display device 100 is capable of full-color display. Note that the coloring layer 129*a*, the coloring layer 129*b*, and the coloring layer 129*c* may each have a function of transmitting light of any of cyan, magenta, and yellow.

The protective layer 132 and the substrate 152 are bonded to each other with an adhesive layer 142. A solid sealing structure, a hollow sealing structure, or the like can be employed to seal the light-emitting devices. In FIG. 17A, a hollow sealing structure is employed in which a space between the substrate 152 and the substrate 151 is filled with the adhesive layer 142. Alternatively, a hollow sealing structure in which the space is filled with an inert gas (e.g., nitrogen or argon) may be employed. The adhesive layer 142 may be provided not to overlap with the light-emitting device. The space may be filled with a resin different from that of the frame-like adhesive layer 142.

The pixel electrodes 111*a*, 111*b*, and 111*c* are each connected to a conductive layer 222*b* included in the transistor 205 through an opening provided in an insulating layer 214.

Depressed portions are formed in the pixel electrodes 111*a*, 111*b*, 111*c* to cover the openings provided in the insulating layer 214. A layer 128 is preferably embedded in the depressed portions. Then, it is preferable that the conductive layer 126*a* be formed over the pixel electrode 111*a* and the layer 128, the conductive layer 126*b* be formed over the pixel electrode 111*b* and the layer 128, and the conductive layer 126*c* be formed over the pixel electrode 111*c* and the layer 128. The conductive layers 126*a*, 126*b*, and 126*c* can also be referred to as pixel electrodes.

The layer 128 has a function of filling the depressed portions of the pixel electrodes 111*a*, 111*b*, and 111*c*. Providing the layer 128 can reduce the unevenness on a surface where the EL layer is to be formed, improving the coverage with the EL layer. With a structure in which the conductive layers 126*a*, 126*b*, and 126*c* which are electrically connected to the pixel electrodes 111*a*, 111*b*, and 111*c* are provided over the pixel electrodes 111*a*, 111*b*, and 111*c* and the layer 128, regions overlapping with the depressed portions of the pixel electrodes 111*a*, 111*b*, and 111*c* can also be used as light-emitting regions in some cases. Therefore, the aperture ratio of a pixel can be increased.

The layer 128 may be an insulating layer or a conductive layer. Any of a variety of inorganic insulating materials, organic insulating materials, and conductive materials can be used for the layer 128 as appropriate. In particular, the layer 128 is preferably formed using an insulating material.

An insulating layer containing an organic material can be suitably used for the layer 128. For the layer 128, an acrylic resin, a polyimide resin, an epoxy resin, a polyamide resin, a polyimide-amide resin, a siloxane resin, a benzocyclobutene-based resin, a phenol resin, a precursor of any of these resins, or the like can be used, for example. A photosensitive resin can also be used for the layer 128. As the photosensitive resin, a positive photosensitive material or a negative photosensitive material can be used.

When a photosensitive resin is used, the layer 128 can be formed through only light-exposure and development steps, reducing the influence of dry etching, wet etching, or the like on the surfaces of the pixel electrodes 111*a*, 111*b*, and 111*c*. When the layer 128 is formed using a negative photosensitive resin, the layer 128 can sometimes be formed using the same photomask (light-exposure mask) as the photomask used for forming the opening in the insulating layer 214.

The conductive layer 126a is provided over the pixel electrode 111a and the layer 128. The conductive layer 126a includes a first region in contact with a top surface of the pixel electrode 111a and a second region in contact with a top surface of the layer 128. It is preferable that the top surface of the pixel electrode 111a in contact with the first region and the top surface of the layer 128 in contact with the second region be level or substantially level with each other.

Similarly, the conductive layer 126b is provided over the pixel electrode 111b and the layer 128. The conductive layer 126b includes a first region in contact with a top surface of the pixel electrode 111b and a second region in contact with the top surface of the layer 128. It is preferable that the top surface of the pixel electrode 111b in contact with the first region and the top surface of the layer 128 in contact with the second region be level or substantially level with each other.

The conductive layer 126c is provided over the pixel electrode 111c and the layer 128. The conductive layer 126c includes a first region in contact with a top surface of the pixel electrode 111c and a second region in contact with the top surface of the layer 128. It is preferable that the top surface of the pixel electrode 111c in contact with the first region and the top surface of the layer 128 in contact with the second region be level or substantially level with each other.

A pixel electrode contains a material that reflects visible light, and a counter electrode contains a material that transmits visible light.

The display device 100A has a top emission structure. Light from the light-emitting device is emitted toward the substrate 152. For the substrate 152, a material having a high visible-light-transmitting property is preferably used.

The layer 101 including a transistor includes a stacked-layer structure including the substrate 151 and components thereover up to the insulating layer 214.

The transistor 201 and the transistor 205 are formed over the substrate 151. These transistors can be manufactured using the same material in the same step.

An insulating layer 211, an insulating layer 213, an insulating layer 215, and the insulating layer 214 are provided in this order over the substrate 151. Part of the insulating layer 211 functions as a gate insulating layer of each transistor. Part of the insulating layer 213 functions as a gate insulating layer of each transistor. The insulating layer 215 is provided to cover the transistors. The insulating layer 214 is provided to cover the transistors and has a function of a planarization layer. Note that the number of gate insulating layers and the number of insulating layers covering the transistors are not limited and may have either a single layer or two or more layers.

A material through which impurities such as water and hydrogen do not easily diffuse is preferably used for at least one of the insulating layers covering the transistors. This is because such an insulating layer can function as a barrier layer. Such a structure can effectively inhibit diffusion of impurities into the transistors from the outside and increase the reliability of the display device.

An inorganic insulating film is preferably used as each of the insulating layer 211, the insulating layer 213, and the insulating layer 215. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may be used. A stack including two or more of the above insulating films may also be used.

Here, an organic insulating film often has a lower barrier property than an inorganic insulating film. Therefore, the organic insulating film preferably has an opening in the vicinity of an end portion of the display device 100A. This can inhibit entry of impurities from the end portion of the display device 100A through the organic insulating film. Alternatively, the organic insulating film may be formed so that its end portion is positioned more inwardly than the end portion of the display device 100A, to prevent the organic insulating film from being exposed at the end portion of the display device 100A.

An organic insulating film is suitable for the insulating layer 214 functioning as a planarization layer. Examples of materials that can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins. Alternatively, a stacked film of an organic insulating film and an inorganic insulating film may be used as the insulating layer 214. The outermost layer of the insulating layer 214 preferably functions as an etching protective film. Accordingly, a depressed portion can be prevented from being formed in the insulating layer 214 at the time of processing the pixel electrode 111a, the conductive layer 126a, or the like. Alternatively, a depressed portion may be formed in the insulating layer 214 at the time of processing the pixel electrode 111a, the conductive layer 126a, or the like.

In a region 228 illustrated in FIG. 17A, an opening is formed in the insulating layer 214. This can inhibit entry of impurities into the display portion 162 from the outside through the insulating layer 214 even when an organic insulating film is used as the insulating layer 214. Consequently, the reliability of the display device 100A can be increased.

Each of the transistor 201 and the transistor 205 includes a conductive layer 221 functioning as a gate, the insulating layer 211 functioning as a gate insulating layer, a conductive layer 222a and the conductive layer 222b functioning as a source and a drain, a semiconductor layer 231, the insulating layer 213 functioning as a gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistors included in the display device in this embodiment. For example, a planar transistor, a staggered transistor, or an inverted staggered transistor can be used. A top-gate or bottom-gate transistor structure can be used. Alternatively, gates may be provided above and below a semiconductor layer where a channel is formed.

The structure in which the semiconductor layer where a channel is formed is provided between two gates is used for the transistor 201 and the transistor 205. The two gates may be connected to each other and supplied with the same signal to drive the transistor. Alternatively, the threshold voltage of the transistor may be controlled by supplying a potential for controlling the threshold voltage to one of the two gates and a potential for driving to the other.

There is no particular limitation on the crystallinity of a semiconductor material used in the semiconductor layer of the transistor, and any of an amorphous semiconductor and a semiconductor having crystallinity (a microcrystalline semiconductor, a polycrystalline semiconductor, a single crystal semiconductor, or a semiconductor partly including crystal regions) may be used. It is preferable to use a semiconductor having crystallinity, in which case degradation of the transistor characteristics can be inhibited.

It is preferable that a semiconductor layer of a transistor contain a metal oxide (also referred to as an oxide semiconductor). That is, a transistor using a metal oxide in its channel formation region (hereinafter, an OS transistor) is preferably used for the display device in this embodiment.

In this specification and the like, a metal oxide is an oxide of a metal in a broad sense. Metal oxides are classified into an oxide insulator, an oxide conductor (including a transparent oxide conductor), an oxide semiconductor (also simply referred to as an OS), and the like. For example, in the case where a metal oxide is used in an active layer of a transistor, the metal oxide is referred to as an oxide semiconductor in some cases. That is, an OS transistor can also be called a transistor including a metal oxide or an oxide semiconductor.

The band gap of a metal oxide used for the semiconductor layer of the transistor is preferably 2 eV or more, further preferably 2.5 eV or more. With use of a metal oxide having a wide bandgap, the off-state current of the OS transistor can be reduced.

A metal oxide preferably contains at least indium or zinc and further preferably contains indium and zinc. A metal oxide preferably contains indium, M (M is one or more kinds selected from gallium, aluminum, yttrium, tin, silicon, boron, copper, vanadium, beryllium, titanium, iron, nickel, germanium, zirconium, molybdenum, lanthanum, cerium, neodymium, hafnium, tantalum, tungsten, magnesium, and cobalt), and zinc, for example. In particular, M is preferably one or more kinds selected from gallium, aluminum, yttrium, and tin, and M is further preferably gallium. Hereinafter, a metal oxide containing indium, M, and zinc is referred to as In-M-Zn oxide in some cases.

When the metal oxide is an In-M-Zn oxide, the atomic ratio of In is preferably greater than or equal to the atomic ratio of M in the In-M-Zn oxide. Examples of the atomic ratio of the metal elements in such an In-M-Zn oxide include In:M:Zn=1:1:1 or a composition in the neighborhood thereof, In:M:Zn=1:1:1.2 or a composition in the neighborhood thereof, In:M:Zn=2:1:3 or a composition in the neighborhood thereof, In:M:Zn=3:1:2 or a composition in the neighborhood thereof, In:M:Zn=4:2:3 or a composition in the neighborhood thereof, In:M:Zn=4:2:4.1 or a composition in the neighborhood thereof, In:M:Zn=5:1:3 or a composition in the neighborhood thereof, In:M:Zn=5:1:6 or a composition in the neighborhood thereof, In:M:Zn=5:1:7 or a composition in the neighborhood thereof, In:M:Zn=5:1:8 or a composition in the neighborhood thereof, In:M:Zn=6:1:6 or a composition in the neighborhood thereof, and In:M:Zn 5=5:2:5 or a composition in the neighborhood thereof. Note that a composition in the neighborhood includes the range of ±30% of an intended atomic ratio. By increasing the proportion of the number of indium atoms in the metal oxide, the on-state current, field-effect mobility, or the like of the transistor can be improved.

For example, when the atomic ratio is described as In:M:Zn=4:2:3 or a composition in the neighborhood thereof, the case is included where the atomic ratio of M is greater than or equal to 1 and less than or equal to 3 and the atomic ratio of Zn is greater than or equal to 2 and less than or equal to 4 with the atomic ratio of In being 4. When the atomic ratio is described as In:M:Zn=5:1:6 or a composition in the neighborhood thereof, the case is included where the atomic ratio of M is greater than 0.1 and less than or equal to 2 and the atomic ratio of Zn is greater than or equal to 5 and less than or equal to 7 with the atomic ratio of In being 5. When the atomic ratio is described as In:M:Zn=1:1:1 or a composition in the neighborhood thereof, the case is included where the atomic ratio of M is greater than 0.1 and less than or equal to 2 and the atomic ratio of Zn is greater than 0.1 and less than or equal to 2 with the atomic ratio of In being 1.

The atomic ratio of In may be less than the atomic ratio of M in the In-M-Zn oxide. Examples of the atomic ratio of the metal elements in such an In-M-Zn oxide include In:M:Zn=1:3:2 or a composition in the neighborhood thereof, In:M:Zn=1:3:3 or a composition in the neighborhood thereof, In:M:Zn=1:3:4 or a composition in the neighborhood thereof. By increasing the proportion of the number of M atoms in the metal oxide, the band gap of the In-M-Zn oxide is further increased; thus, the resistance to a negative bias stress test with light irradiation can be improved. Specifically, the amount of change in the threshold voltage or the amount of change in the shift voltage (Vsh) measured in a NBTIS (Negative Bias Temperature Illumination Stress) test of the transistor can be decreased. Note that the shift voltage (Vsh) is defined as Vg at which, in a drain current (Id)-gate voltage (Vg) curve of a transistor, the tangent at a point where the slope of the curve is the steepest intersects the straight line of Id=1 pA.

Alternatively, a semiconductor layer of a transistor may contain silicon. Examples of silicon include amorphous silicon and crystalline silicon (e.g., low-temperature polysilicon or single crystal silicon).

Alternatively, a semiconductor layer of a transistor may contain a layered material that functions as a semiconductor. The layered material is a general term of a group of materials having a layered crystal structure. In the layered crystal structure, layers formed by covalent bonding or ionic bonding are stacked with bonding such as the Van der Waals force, which is weaker than covalent bonding or ionic bonding. The layered material has high electrical conductivity in a monolayer, that is, high two-dimensional electrical conductivity. When a material functioning as a semiconductor and having high two-dimensional electrical conductivity is used for a channel formation region, a transistor having a high on-state current can be provided.

Examples of the layered materials include graphene, silicene, and chalcogenide. Chalcogenide is a compound containing chalcogen (an element belonging to Group 16). Examples of chalcogenide include transition metal chalcogenide and chalcogenide of Group 13 elements. Specific examples of the transition metal chalcogenide which can be used for a semiconductor layer of a transistor include molybdenum sulfide (typically $MoS_2$), molybdenum selenide (typically $MoSe_2$), molybdenum telluride (typically $MoTe_2$), tungsten sulfide (typically $WS_2$), tungsten selenide (typically $WSe_2$), tungsten telluride (typically $WTe_2$), hafnium sulfide (typically $HfS_2$), hafnium selenide (typically $HfSe_2$), zirconium sulfide (typically $ZrS_2$), and zirconium selenide (typically $ZrSe_2$).

The transistor included in the circuit 164 and the transistor included in the display portion 162 may have the same structure or different structures. One structure or two or more kinds of structures may be employed for a plurality of transistors included in the circuit 164. Similarly, one structure or two or more kinds of structures may be employed for a plurality of transistors included in the display portion 162.

FIG. 17B and FIG. 17C illustrate other structure examples of transistors.

The transistor 209 and the transistor 210 each include the conductive layer 221 functioning as a gate, the insulating layer 211 functioning as a gate insulating layer, the semiconductor layer 231 including a channel formation region 231*i* and a pair of low-resistance regions 231*n*, the conductive layer 222*a* connected to one of the low-resistance regions 231*n*, the conductive layer 222*b* connected to the other low-resistance region 231*n*, the insulating layer 225 functioning as a gate insulating layer, the conductive layer 223 functioning as a gate, and the insulating layer 215 covering the conductive layer 223. The insulating layer 211 is positioned between the conductive layer 221 and the channel formation region 231*i*. The insulating layer 225 is positioned at least between the conductive layer 223 and the channel formation region 231*i*. Furthermore, an insulating layer 218 covering the transistor may be provided.

FIG. 17B illustrates an example of the transistor 209 in which the insulating layer 225 covers a top surface and a side surface of the semiconductor layer 231. The conductive layer 222*a* and the conductive layer 222*b* are connected to the corresponding low-resistance regions 231*n* through openings provided in the insulating layer 225 and the insulating layer 215. One of the conductive layer 222*a* and the conductive layer 222*b* functions as a source, and the other functions as a drain.

In the transistor 210 illustrated in FIG. 17C, the insulating layer 225 overlaps with the channel formation region 231*i* of the semiconductor layer 231 and does not overlap with the low-resistance regions 231*n*. The structure illustrated in FIG. 17C is obtained by processing the insulating layer 225 with the conductive layer 223 as a mask, for example. In FIG. 17C, the insulating layer 215 is provided to cover the insulating layer 225 and the conductive layer 223, and the conductive layer 222*a* and the conductive layer 222*b* are connected to the corresponding low-resistance regions 231*n* through the openings in the insulating layer 215.

A connection portion 204 is provided in a region of the substrate 151 where the substrate 152 does not overlap. In the connection portion 204, the wiring 165 is electrically connected to the FPC 172 through a conductive layer 166 and a connection layer 242. An example is illustrated in which the conductive layer 166 has a stacked-layer structure of a conductive film obtained by processing the same conductive film as the pixel electrodes 111*a*, 111*b*, and 111*c* and a conductive film obtained by processing the same conductive film as the conductive layers 126*a*, 126*b*, and 126*c*. On a top surface of the connection portion 204, the conductive layer 166 is exposed. Thus, the connection portion 204 and the FPC 172 can be electrically connected to each other through the connection layer 242.

A light-blocking layer 117 is preferably provided on the surface of the substrate 152 on the substrate 151 side. In addition, the coloring layers 129*a* and 129*b* may be provided on the surface of the substrate 152 on the substrate 151 side. In FIG. 17A, when the substrate 152 is viewed through the substrate 151, the coloring layers 129*a*, 129*b*, and 129*c* are provided to cover part of the light-blocking layer 117.

A variety of optical members can be arranged on the outer surface of the substrate 152. Examples of the optical members include a polarizing plate, a retardation plate, a light diffusion layer (e.g., a diffusion film), an anti-reflective layer, and a light-condensing film. Furthermore, an antistatic film preventing the attachment of dust, a water repellent film suppressing the attachment of stain, a hard coat film suppressing generation of a scratch caused by the use, an impact-absorbing layer, or the like may be arranged on the outer surface of the substrate 152.

The protective layer 131 and the protective layer 132 covering the light-emitting device can inhibit an impurity such as water from entering the light-emitting device, and increase the reliability of the light-emitting device.

In the region 228 in the vicinity of the end portion of the display device 100A, the insulating layer 215 and the protective layer 131 or the protective layer 132 are preferably in contact with each other through an opening in the insulating layer 214. In particular, the inorganic insulating films are preferably in contact with each other. Thus, entry of impurities from the outside into the display portion 162 through the organic insulating film can be inhibited. Consequently, the reliability of the display device 100A can be increased.

For each of the substrate 151 and the substrate 152, glass, quartz, ceramics, sapphire, a resin, a metal, an alloy, a semiconductor, or the like can be used. For the substrate on the side from which light from the light-emitting device is extracted, a material that transmits the light is used. When the substrate 151 and the substrate 152 are formed using a flexible material, the flexibility of the display device can be increased. Furthermore, a polarizing plate may be used as the substrate 151 or the substrate 152.

For each of the substrate 151 and the substrate 152, any of the following can be used, for example: polyester resins such as polyethylene terephthalate (PET) and polyethylene naphthalate (PEN), a polyacrylonitrile resin, an acrylic resin, a polyimide resin, a polymethyl methacrylate resin, a polycarbonate (PC) resin, a polyethersulfone (PES) resin, polyamide resins (e.g., nylon and aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, and cellulose nanofiber. Glass that is thin enough to have flexibility may be used for one or both of the substrate 151 and the substrate 152.

In the case where a circularly polarizing plate overlaps with the display device, a highly optically isotropic substrate is preferably used as the substrate included in the display device. A highly optically isotropic substrate has a low birefringence (in other words, a small amount of birefringence).

The absolute value of a retardation (phase difference) of a highly optically isotropic substrate is preferably less than or equal to 30 nm, further preferably less than or equal to 20 nm, still further preferably less than or equal to 10 nm.

Examples of a highly optically isotropic film include a triacetyl cellulose (TAC, also referred to as cellulose triacetate) film, a cycloolefin polymer (COP) film, a cycloolefin copolymer (COC) film, and an acrylic film.

When a film is used for the substrate and the film absorbs water, the shape of the display panel might be changed, e.g., creases are generated. Thus, for the substrate, a film with a low water absorption rate is preferably used. For example, the water absorption rate of the film is preferably 1% or lower, further preferably 0.1% or lower, still further preferably 0.01% or lower.

As the adhesive layer 142, a variety of curable adhesives, e.g., a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC (polyvinyl chloride) resin, a PVB (polyvinyl butyral) resin, and an EVA (ethylene vinyl acetate) resin. In particular, a material with low moisture permeability, such as an epoxy resin, is preferred. A two-component-mixture-type resin may be used. An adhesive sheet or the like may be used.

As the connection layer 242, an anisotropic conductive film (ACF), an anisotropic conductive paste (ACP), or the like can be used.

As materials for the gates, the source, and the drain of a transistor and conductive layers such as a variety of wirings and electrodes included in the display device, any of metals such as aluminum, titanium, chromium, nickel, copper, yttrium, zirconium, molybdenum, silver, tantalum, and tungsten, or an alloy containing any of these metals as its main component can be used. A single-layer structure or a stacked-layer structure including a film containing any of these materials can be used.

As a light-transmitting conductive material, a conductive oxide such as indium oxide, indium tin oxide, indium zinc oxide, zinc oxide, or zinc oxide containing gallium, or graphene can be used. It is also possible to use a metal material such as gold, silver, platinum, magnesium, nickel, tungsten, chromium, molybdenum, iron, cobalt, copper, palladium, or titanium; or an alloy material containing any of these metal materials. Alternatively, a nitride of the metal material (e.g., titanium nitride) or the like may be used. Note that in the case of using the metal material or the alloy material (or the nitride thereof), the thickness is preferably set small enough to transmit light. Alternatively, a stacked film of any of the above materials can be used for the conductive layers. For example, a stacked film of indium tin oxide and an alloy of silver and magnesium is preferably used because conductivity can be increased. They can also be used for conductive layers such as wirings and electrodes included in the display device, and conductive layers (e.g., a conductive layer functioning as a pixel electrode or a common electrode) included in a light-emitting device.

Examples of insulating materials that can be used for the insulating layers include resins such as an acrylic resin and an epoxy resin, and inorganic insulating materials such as silicon oxide, silicon oxynitride, silicon nitride oxide, silicon nitride, and aluminum oxide.

[Display Device 100B]

Figure 18:
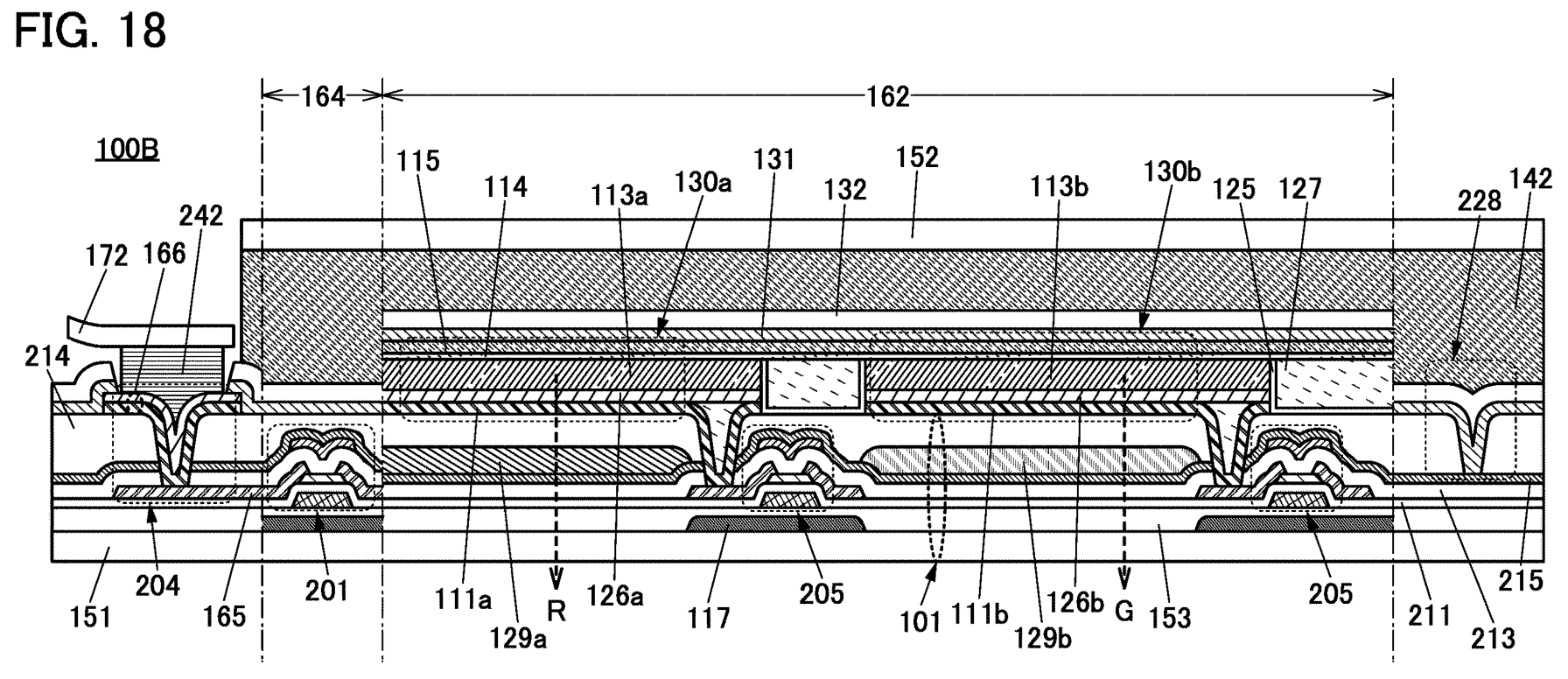

A display device 100B illustrated in FIG. 18 is different from the display device 100A mainly in having a bottom-emission structure. Note that portions similar to those in the display device 100A are not described. Note that although FIG. 18 illustrates a subpixel including the first layer 113a and a subpixel including the second layer 113b, three or more kinds of subpixels can be provided as in FIG. 17A.

Light from the light-emitting device is emitted toward the substrate 151 side. For the substrate 151, a material having a high visible-light-transmitting property is preferably used. By contrast, there is no limitation on the light-transmitting property of a material used for the substrate 152.

In the display device 100B, the pixel electrodes 111a and 111b and the conductive layers 126a and 126b contain a material that transmits visible light, and the common electrode 115 contains a material that reflects visible light. Here, the conductive layer 166 that is obtained by processing the same conductive film as the pixel electrodes 111a and 111b and the conductive layers 126a and 126b also contains a material that transmits visible light.

The light-blocking layer 117 is preferably formed between the substrate 151 and the transistor 201 and between the substrate 151 and the transistor 205. FIG. 18 illustrates an example in which the light-blocking layer 117 is provided over the substrate 151, an insulating layer 153 is provided over the light-blocking layer 117, and the transistors 201 and 205 and the like are provided over the insulating layer 153.

Moreover, in the display device 100B, the coloring layers 129a and 129b are provided between the insulating layer 215 and the insulating layer 214. End portions of the coloring layers 129a and 129b preferably overlap with the light-blocking layer 117.

FIG. 19A to FIG. 19D illustrate cross-sectional structures of a region 138 including the pixel electrode 111a, the layer 128, and the vicinity thereof in the display device 100A and the display device 100B. Note that as the description relating to FIG. 19A to FIG. 19D, the same can apply to the light-emitting device 130b and the light-emitting device 130c.

Figure 19A:
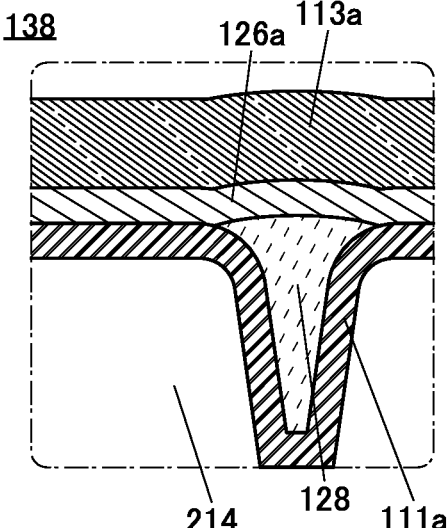
FIG. 19A to FIG. 19D are cross-sectional views illustrating examples of a display device.

FIG. 17A and FIG. 18 each illustrate an example in which the top surface of the layer 128 and the top surface of the pixel electrode 111a are substantially at the same level; however, the present invention is not limited to such an example. For example, as illustrated in FIG. 19A, the top surface of the layer 128 may be at a higher level than that of the pixel electrode 111a. Moreover, the top surface of the layer 128 has a convex shape that is gently bulged toward the center.

Figure 19B:
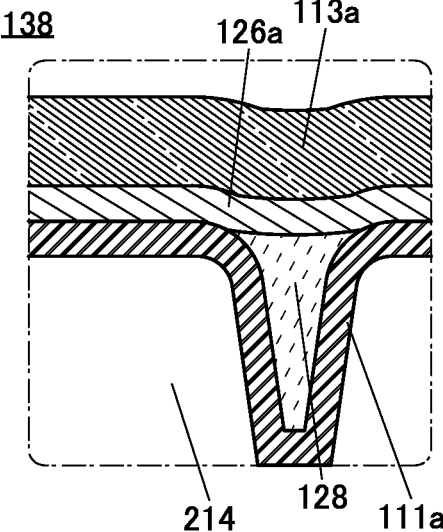

As illustrated in FIG. 19B, the top surface of the layer 128 may be at a lower level than that of the pixel electrode 111a. Moreover, the top surface of the insulating layer 128 has a concave shape that is gently recessed toward the center.

Figure 19C:
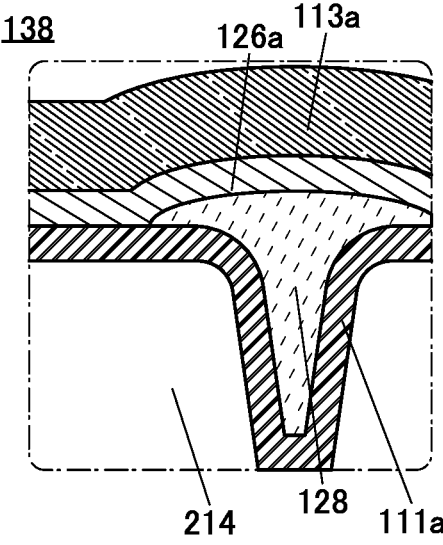

When the top surface of the layer 128 is at a higher level than that of the pixel electrode 111a as illustrated in FIG. 19C, the upper portion of the layer 128 is formed to extend beyond a recessed portion in the pixel electrode 111a in some cases. In this case, part of the layer 128 may be formed to cover part of the pixel electrode 111a which is substantially flat.

Figure 19D:
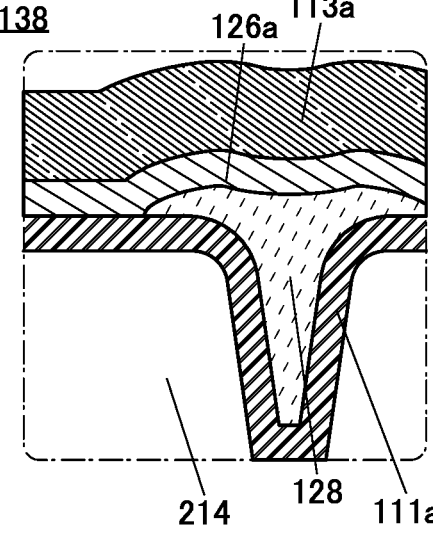

As illustrated in FIG. 19D, a part of the top surface of layer 128 has another depression portion in the structure of FIG. 19C, in some cases. The recessed portion has a shape that is gently recessed toward the middle.

FIGS. 20A to 20F illustrate cross-sectional structures of a region 139 including the insulating layer 127, and the vicinity thereof in the display device 100A and the display device 100B.

Figure 20A:
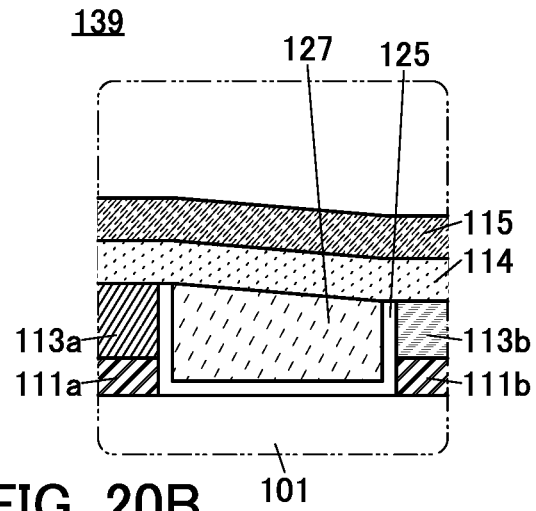
FIG. 20A to FIG. 20F are cross-sectional views illustrating an example of a method for manufacturing a display device.

FIG. 20A illustrates an example in which the first layer 113a and the second layer 113b have different thicknesses. The top surface of the insulating layer 125 is level or substantially level with the top surface of the first layer 113a on the first layer 113a side, and level or substantially level with the top surface of the second layer 113b on the second layer 113b side. The top surface of the insulating layer 127 has a gentle slope such that the side closer to the first layer 113a is higher and the side closer to the second layer 113b is lower. In this manner, the top surfaces of the insulating layers 125 and 127 are preferably level with the top surface of the adjacent EL layer. Alternatively, the top surface of the insulating layer 127 may have a flat portion and be level with the top surface of any adjacent EL layer.

Figure 20D:
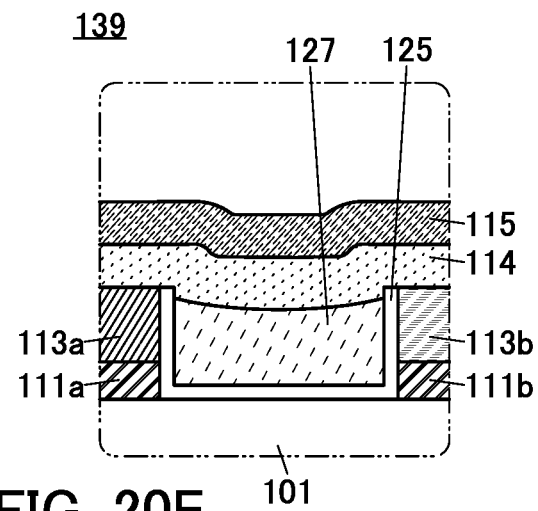
Figure 20B:
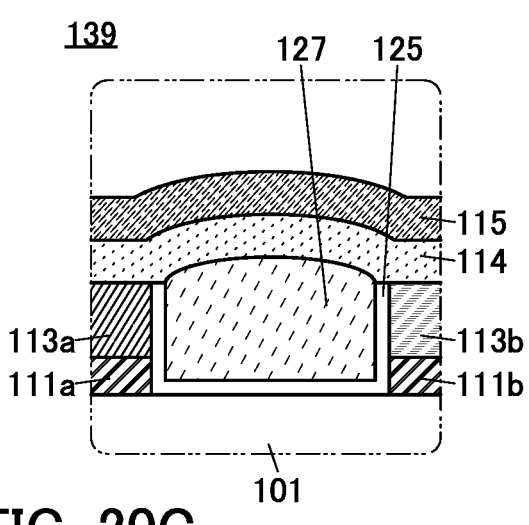

In FIG. 20B, the top surface of the insulating layer 127 includes a region whose level is higher than those of the top surface of the first layer 113a and the top surface of the second layer 113*b*. Moreover, the top surface of the insulating layer 127 has a convex shape that is gently curved outward toward the center.

Figure 20E:
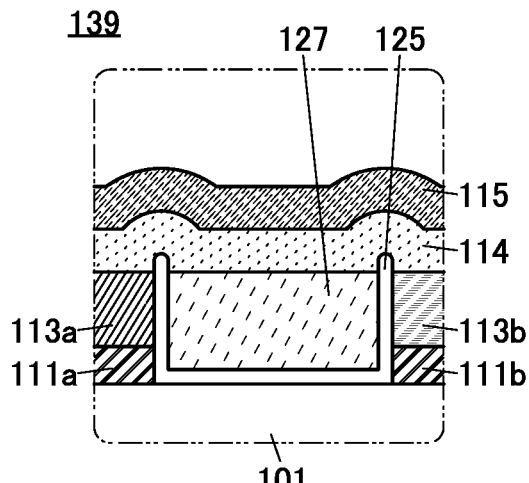
Figure 20C:
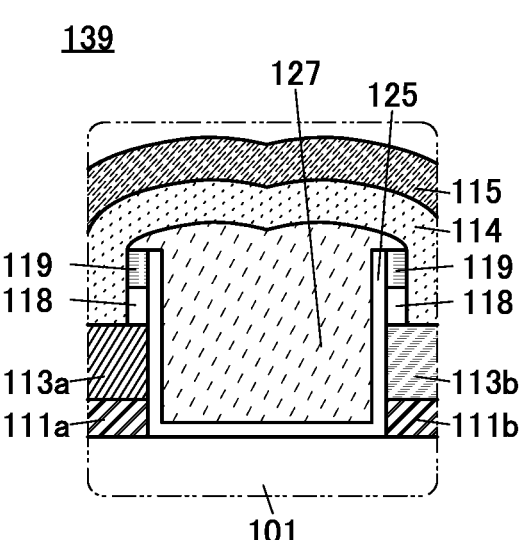

In FIG. 20C, the insulating layer 127 includes a region whose level is higher than those of the top surface of the first layer 113*a* and the top surface of the second layer 113*b*. In the region 139, the display device 100A and the display device 100B include at least one of the first sacrificial layer 118 and the second sacrificial layer 119, and includes a first region where the top surface of the insulating layer 127 is at a higher level than the top surface of the first layer 113*a* and the top surface of the second layer 113*b* and the insulating layer 127 is located closer to the outer side than the insulating layer 125. The first region is positioned over at least one of the first sacrificial layer 118 and the second sacrificial layer 119.

In FIG. 20D, the top surface of the insulating layer 127 includes a region whose level is less than those of the top surface of the first layer 113*a* and the top surface of the second layer 113*b*. Moreover, the top surface of the insulating layer 127 has a concave shape that is gently recessed toward the center.

In FIG. 20E, the top surface of the insulating layer 125 includes a region whose level is higher than that of the top surface of the first layer 113*a* and the top surface of the second layer 113*b*. That is, the insulating layer 125 protrudes from the formation surface of the fifth layer 114 and forms a projecting portion.

For example, when the insulating layer 125 is formed so that its level agree with or substantially agree with the level of the sacrificial layer, the insulating layer 125 may protrude as illustrated in FIG. 20E.

Figure 20F:
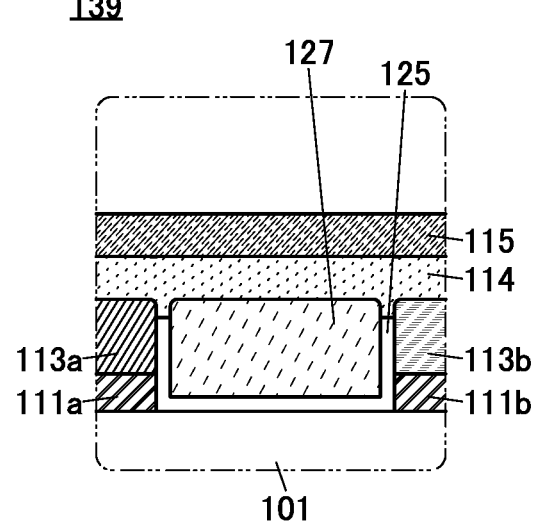

In FIG. 20F, the top surface of the insulating layer 125 includes a region whose level is less than that of the top surface of the first layer 113*a* and the top surface of the second layer 113*b*. That is, the insulating layer 125 forms a depressed portion on the formation surface of the fifth layer 114.

As described above, the insulating layer 125 and the insulating layer 127 can have a variety of shapes.

[Pixel Layout]

Next, a pixel layout is described. There is no particular limitation on the arrangement of subpixels, and a variety of methods can be employed. Examples of the arrangement of subpixels include stripe arrangement, S-stripe arrangement, matrix arrangement, delta arrangement, Bayer arrangement, and PenTile arrangement.

Examples of a top surface shape of the subpixel include polygons such as a triangle, a tetragon (including a rectangle and a square), and a pentagon; polygons with rounded corners; an ellipse; and a circle. Here, a top surface shape of the subpixel corresponds to a top surface shape of a light-emitting region of the light-emitting device.

Figures 21A, 21B, 21C, 21D, 21E, 21F, 21G:
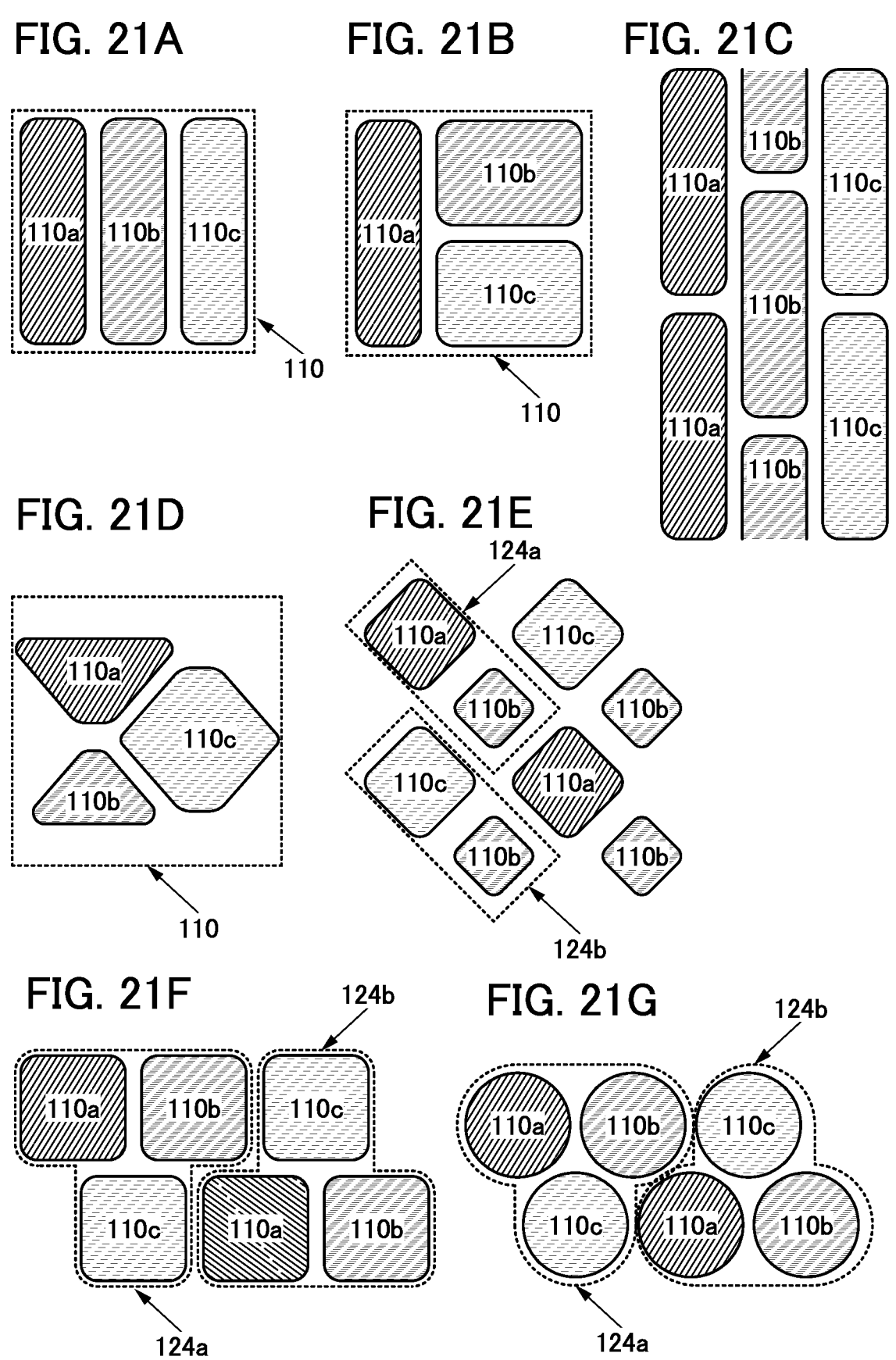
FIG. 21A to FIG. 21G are top views illustrating examples of a pixel.
Figures 22A, 22B, 22C, 22D, 22E, 22F:
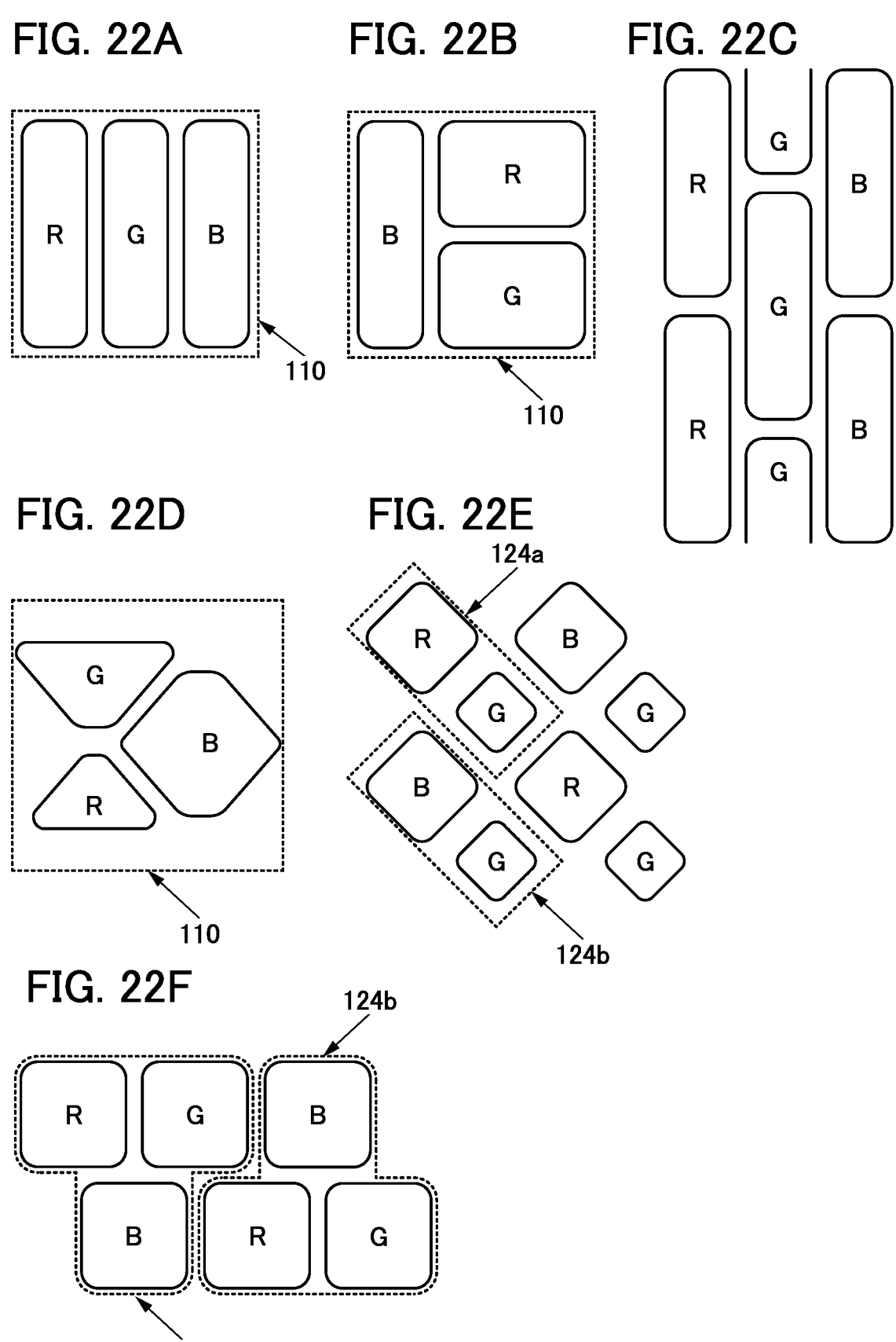
FIG. 22A to FIG. 22F are top views illustrating examples of a pixel.

A pixel 110 illustrated in FIG. 21A employs stripe arrangement. The pixel 110 illustrated in FIG. 21A consists of three subpixels 110*a*, 110*b*, and 110*c*. For example, as illustrated in FIG. 22A, the subpixel 110*a* may be a red subpixel R, the subpixel 110*b* may be a green subpixel G, and the subpixel 110*c* may be a blue subpixel B.

The pixel 110 illustrated in FIG. 21B employs S-stripe arrangement. The pixel 110 illustrated in FIG. 21B consists of three subpixels 110*a*, 110*b*, and 110*c*. For example, as illustrated in FIG. 22B, the subpixel 110*a* may be a blue subpixel B, the subpixel 110*b* may be a red subpixel R, and the subpixel 110*c* may be a green subpixel G.

FIG. 21C illustrates an example where subpixels of different colors are arranged in a zigzag manner. Specifically, the positions of the top sides of two subpixels arranged in the column direction (e.g., the subpixel 110*a* and the subpixel 110*b* or the subpixel 110*b* and the subpixel 110*c*) are not aligned in the top view. For example, as illustrated in FIG. 22C, the subpixel 110*a* may be a red subpixel R, the subpixel 110*b* may be a green subpixel G, and the subpixel 110*c* may be a blue subpixel B.

The pixel 110 illustrated in FIG. 21D includes the subpixel 110*a* whose top surface shape is a rough trapezoid with rounded corners, the subpixel 110*b* whose top surface shape is a rough triangle with rounded corners, and the subpixel 110*c* whose top surface shape is a rough tetragon or rough hexagon with rounded corners. The subpixel 110*a* has a larger light-emitting area than the subpixel 110*b*. In this manner, the shapes and sizes of the subpixels can be determined independently. For example, the size of a subpixel including a light-emitting device with higher reliability can be smaller. For example, as illustrated in FIG. 22D, the subpixel 110*a* may be a green subpixel G, the subpixel 110*b* may be a red subpixel R, and the subpixel 110*c* may be a blue subpixel B.

Pixels 124*a* and 124*b* illustrated in FIG. 21E employ PenTile arrangement. FIG. 21E illustrates an example in which the pixels 124*a* including the subpixels 110*a* and 110*b* and the pixels 124*b* including the subpixels 110*b* and 110*c* are alternately arranged. For example, as illustrated in FIG. 22E, the subpixel 110*a* may be a red subpixel R, the subpixel 110*b* may be a green subpixel G, and the subpixel 110*c* may be a blue subpixel B.

The pixels 124*a* and 124*b* illustrated in FIG. 21F and FIG. 21G employ delta arrangement. The pixel 124*a* includes two subpixels (the subpixels 110*a* and 110*b*) in the upper row (first row) and one subpixel (the subpixel 110*c*) in the lower row (second row). The pixel 124*b* includes one subpixel (the subpixel 110*c*) in the upper row (first row) and two subpixels (the subpixels 110*a* and 110*b*) in the lower row (second row). For example, as illustrated in FIG. 22F, the subpixel 110*a* may be a red subpixel R, the subpixel 110*b* may be a green subpixel G, and the subpixel 110*c* may be a blue subpixel B.

FIG. 21F illustrates an example where a top surface shape of each subpixel is a rough tetragon with rounded corners, and FIG. 21G illustrates an example where a top surface shape of each subpixel is a circle.

In a photolithography method, as a pattern to be processed becomes finer, the influence of light diffraction becomes more difficult to ignore; therefore, the fidelity in transferring a photomask pattern by light exposure is degraded, and it becomes difficult to process a resist mask into a desired shape. Thus, a pattern with rounded corners is likely to be formed even with a rectangular photomask pattern. Consequently, the top surface of a subpixel can have a polygonal shape with rounded corners, an elliptical shape, a circular shape, or the like.

Furthermore, in the method of manufacturing the display device of one embodiment of the present invention, the EL layer is processed into an island shape with use of a resist mask. A resist film formed over the EL layer needs to be cured at a temperature lower than the upper temperature limit of the EL layer. Therefore, the resist film is insufficiently cured in some cases depending on the upper temperature limit of the material of the EL layer and the curing temperature of the resist material. An insufficiently cured resist film may have a shape different from a desired shape by processing. As a result, the top surface of the EL layer may have a polygonal shape with rounded corners, an elliptical shape, a circular shape, or the like. For example, when a resist mask with a square top surface is intended to be formed, a resist mask with a circular top surface may be formed, and the top surface of the EL layer may be circular.

To obtain a desired top surface shape of the EL layer, a technique of correcting a mask pattern in advance so that a transferred pattern agrees with a design pattern (an optical proximity correction (OPC) technique) may be used. Specifically, with the OPC technique, a pattern for correction is added to a corner portion or the like of a figure on a mask pattern.

Figures 23A, 23B, 23C, 23D, 23E, 23F, 23G, 23H:
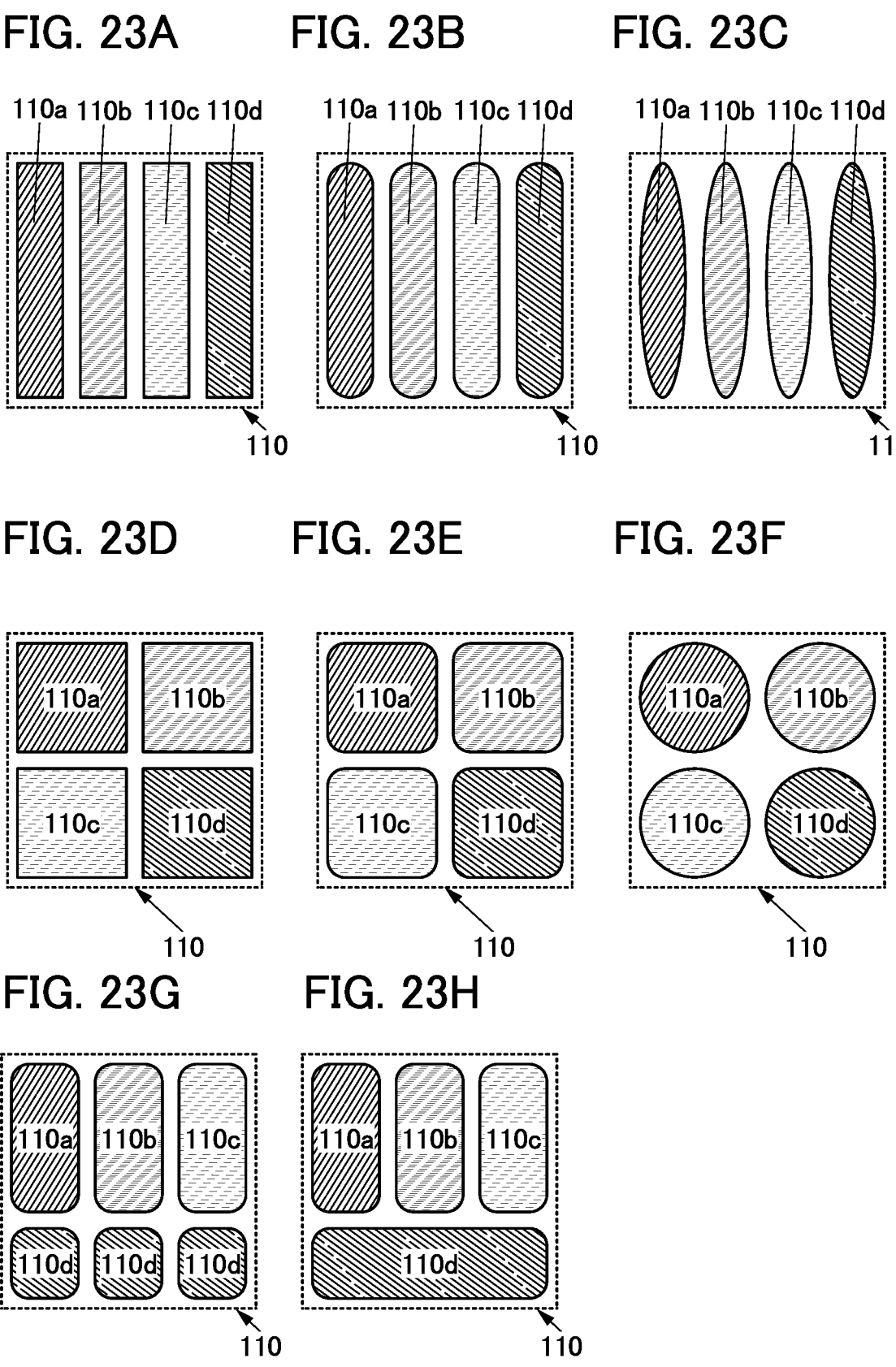
FIG. 23A to FIG. 23H are top views illustrating examples of a pixel.

The pixels 110 illustrated in FIG. 23A to 23C each employ stripe arrangement.

FIG. 23A illustrates an example where each subpixel has a rectangular top surface. FIG. 23B illustrates an example where each subpixel has a top surface shape formed by combining two half circles and a rectangle. FIG. 23C illustrates an example where each subpixel has an elliptical top surface.

The pixels 110 illustrated in FIG. 23D to 23F each employ matrix arrangement.

FIG. 23D illustrates an example where each subpixel has a square top surface. FIG. 23E illustrates an example where each subpixel has a substantially square top surface with rounded corners. FIG. 23F illustrates an example where each subpixel has a circular top surface.

Figures 24A, 24B, 24C:
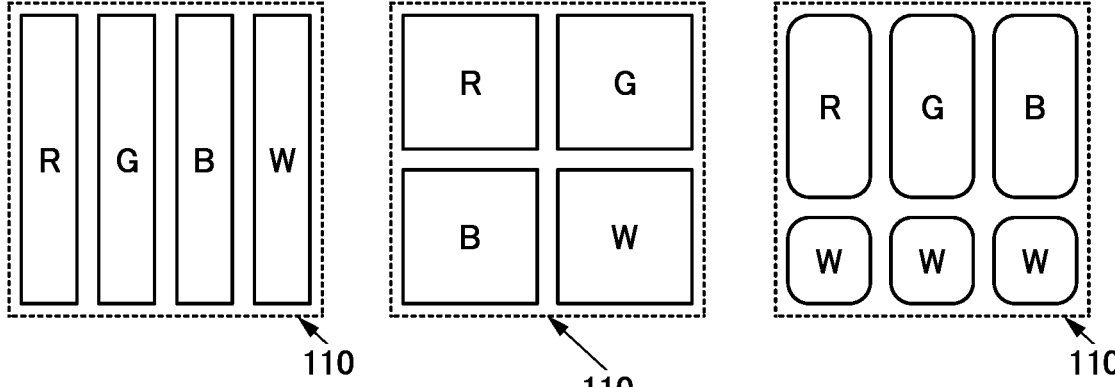
FIG. 24A to FIG. 24D are top views illustrating examples of a pixel.

The pixel 110 illustrated in FIG. 23A to FIG. 23F consists of four subpixels 110a, 110b, 110c, and 110d. The subpixels 110a, 110b, 110c, and 110d include light-emitting devices that emit light of different colors from one another. For example, the subpixels 110a, 110b, 110c, and 110d can be red, green, blue, and white subpixels, respectively. For example, the subpixels 110a, 110b, 110c, and 110d can be red, green, blue, and white subpixels, respectively, as illustrated in FIG. 24A and FIG. 24B. Alternatively, the subpixels 110a, 110b, 110c, and 110d can be red, green, blue, and infrared-light subpixels, respectively.

The subpixel 110d includes a light-emitting device that emits visible light. The light-emitting device includes a pixel electrode, an island-shaped fourth layer over the pixel electrode, the fifth layer 114 over the island-shaped fourth layer, and the common electrode 115 over the fifth layer 114. In the light-emitting device, the fourth layer and the fifth layer 114 can be collectively referred to as an EL layer. The pixel electrode is formed using a material similar to that for the pixel electrode 111a, the pixel electrode 111b, and the pixel electrode 111c. The fourth layer is formed using a material similar to that for the first layer 113a, the second layer 113b, and the third layer 113c.

FIG. 23G illustrates an example in which one pixel 110 consists of two rows and three columns. The pixel 110 includes three subpixels (the subpixel 110a, the subpixel 110b, and the subpixel 110c) in the upper row (first row) and three subpixels 110d in the lower row (second row). In other words, the pixel 110 includes the subpixel 110a and the subpixel 110d in the left column (first column), the subpixel 110b and another subpixel 110d in the center column (second column), and the subpixel 110c and another subpixel 110d in the right column (third column). Matching the positions of the subpixels in the upper row and the lower row as illustrated in FIG. 23G enables dust and the like that would be produced in the manufacturing process to be removed efficiently. Accordingly, a display device that has high display quality can be provided.

FIG. 23H illustrates an example in which one pixel 110 consists of two rows and three columns. The pixel 110 includes three subpixels (the subpixel 110a, the subpixel 110b, and the subpixel 110c) in the upper row (first row) and one subpixel (the subpixel 110d) in the lower row (second row). In other words, the pixel 110 includes the subpixel 110a in the left column (first column), the subpixel 110b in the center column (second column), the subpixel 110c in the right column (third column), and the subpixel 110d across these three columns.

Figure 24D:
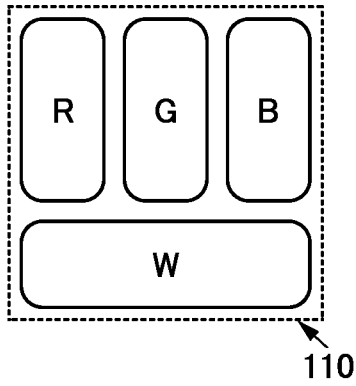

In the pixel 110 in each of FIG. 23G and FIG. 23H, for example, the subpixel 110a can be the red subpixel R, the subpixel 110b can be the green subpixel G, the subpixel 110c can be the blue subpixel B, and the subpixel 110d can be a white subpixel W, as illustrated in FIG. 24C and FIG. 24D.

The display device of one embodiment of the present invention may include a light-receiving device in the pixel.

Three of the four subpixels included in the pixel 110 in FIG. 23G may include a light-emitting device and the other one may include a light-receiving device.

For example, a pn or pin photodiode can be used as the light-receiving device. The light-receiving device functions as a photoelectric conversion device (also referred to as a photoelectric conversion element) that detects light entering the light-receiving device and generates electric charge. The amount of electric charge generated from the light-receiving device depends on the amount of light entering the light-receiving device.

It is particularly preferable to use an organic photodiode including a layer containing an organic compound, as the light-receiving device. An organic photodiode, which is easily made thin, lightweight, and large in area and has a high degree of freedom for shape and design, can be used in a variety of display devices.

In one embodiment of the present invention, organic EL devices are used as the light-emitting devices, and organic photodiodes are used as the light-receiving devices. The organic EL device and the organic photodiode can be formed over the same substrate. Thus, the organic photodiodes can be incorporated in a display device including the organic EL devices.

The light-receiving device includes at least an active layer that functions as a photoelectric conversion layer between a pair of electrodes. In this specification and the like, in some cases, one of the pair of electrodes is referred to as a pixel electrode and the other of the pair of electrodes is referred to as a common electrode.

For example, the subpixels 110a, 110b, and 110c may be subpixels for three colors of R, G, and B, and the subpixel 110d may be a subpixel including the light-receiving device. In that case, the fourth layer includes at least an active layer.

One of the pair of electrodes of the light-receiving device functions as an anode, and the other electrode functions as a cathode. The case where the pixel electrode functions as an anode and the common electrode functions as a cathode is described below as an example. When the light-receiving device is driven by application of reverse bias between the pixel electrode and the common electrode, light entering the light-receiving device can be sensed and charge can be generated and extracted as current. Alternatively, the pixel electrode may function as a cathode and the common electrode may function as an anode.

A manufacturing method similar to that of the light-emitting device can be employed for the light-receiving device. An island-shaped active layer (also referred to as a photoelectric conversion layer) included in the light-receiving device is formed by processing a film that is to be the active layer and formed on the entire surface, not by using a pattern of a metal mask; thus, the island-shaped active layer with a uniform thickness can be formed. In addition, a sacrifice layer provided over the active layer can reduce damage to the active layer in the manufacturing process of the display device, increasing the reliability of the light-receiving device.

Here, a layer shared by the light-receiving device and the light-emitting device might have different functions in the light-emitting device and the light-receiving device. In this specification, the name of a component is based on its function in the light-emitting device in some cases. For example, a hole-injection layer functions as a hole-injection layer in the light-emitting device and functions as a hole-transport layer in the light-receiving device. Similarly, an electron-injection layer functions as an electron-injection layer in the light-emitting device and functions as an electron-transport layer in the light-receiving device. A layer shared by the light-receiving device and the light-emitting device might have the same function in both the light-emitting device and the light-receiving device. The hole-transport layer functions as a hole-transport layer in both the light-emitting device and the light-receiving device, and the electron-transport layer functions as an electron-transport layer in both the light-emitting device and the light-receiving device.

The active layer included in the light-receiving device includes a semiconductor. Examples of the semiconductor include an inorganic semiconductor such as silicon and an organic semiconductor including an organic compound. This embodiment shows an example in which an organic semiconductor is used as the semiconductor contained in the active layer. The use of an organic semiconductor is preferable because the light-emitting layer and the active layer can be formed by the same method (e.g., a vacuum evaporation method) and thus the same manufacturing apparatus can be used.

Examples of an n-type semiconductor material included in the active layer are electron-accepting organic semiconductor materials such as fullerene (e.g., $C_{60}$ and $C_{70}$) and fullerene derivatives. Fullerene has a soccer ball-like shape, which is energetically stable. Both the HOMO level and the LUMO level of fullerene are deep (low). Having a deep LUMO level, fullerene has an extremely high electron-accepting property (acceptor property). When $\pi$-electron conjugation (resonance) spreads in a plane as in benzene, the electron-donating property (donor property) usually increases. Although $\pi$-electrons widely spread in fullerene having a spherical shape, its electron-accepting property is high. The high electron-accepting property efficiently causes rapid charge separation and is useful for the light-receiving element. Both $C_{60}$ and $C_{70}$ have a wide absorption band in the visible light region, and $C_{70}$ is especially preferable because of having a larger $\pi$-electron conjugation system and a wider absorption band in the long wavelength region than $C_{60}$. Other examples of fullerene derivatives include [6,6]-phenyl-$C_{71}$-butyric acid methyl ester (abbreviation: $PC_{70}BM$), [6,6]-phenyl-$C_{61}$-butyric acid methyl ester (abbreviation: $PC_{60}BM$), and 1',1'',4',4''-tetrahydro-di [1,4] methanonaphthaleno[1,2:2',3',56,60:2'',3''][5,6]fullerene-$C_{60}$ (abbreviation: ICBA).

Other examples of an n-type semiconductor material include a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative, a benzoquinoline derivative, a quinoxaline derivative, a dibenzoquinoxaline derivative, a pyridine derivative, a bipyridine derivative, a pyrimidine derivative, a naphthalene derivative, an anthracene derivative, a coumarin derivative, a rhodamine derivative, a triazine derivative, and a quinone derivative.

Examples of a p-type semiconductor material contained in the active layer include electron-donating organic semiconductor materials such as copper(II) phthalocyanine (CuPc), tetraphenyldibenzoperiflanthene (DBP), zinc phthalocyanine (ZnPc), tin phthalocyanine (SnPc), and quinacridone.

Examples of a p-type semiconductor material include a carbazole derivative, a thiophene derivative, a furan derivative, and a compound having an aromatic amine skeleton. Other examples of the p-type semiconductor material include a naphthalene derivative, an anthracene derivative, a pyrene derivative, a triphenylene derivative, a fluorene derivative, a pyrrole derivative, a benzofuran derivative, a benzothiophene derivative, an indole derivative, a dibenzofuran derivative, a dibenzothiophene derivative, an indolocarbazole derivative, a porphyrin derivative, a phthalocyanine derivative, a naphthalocyanine derivative, a quinacridone derivative, a polyphenylene vinylene derivative, a polyparaphenylene derivative, a polyfluorene derivative, a polyvinylcarbazole derivative, and a polythiophene derivative.

The HOMO level of the electron-donating organic semiconductor material is preferably shallower (higher) than the HOMO level of the electron-accepting organic semiconductor material. The LUMO level of the electron-donating organic semiconductor material is preferably shallower (higher) than the LUMO level of the electron-accepting organic semiconductor material.

Fullerene having a spherical shape is preferably used as the electron-accepting organic semiconductor material, and an organic semiconductor material having a substantially planar shape is preferably used as the electron-donating organic semiconductor material. Molecules of similar shapes tend to aggregate, and aggregated molecules of similar kinds, which have molecular orbital energy levels close to each other, can increase the carrier-transport property.

For example, the active layer is preferably formed by co-evaporation of an n-type semiconductor and a p-type semiconductor. Alternatively, the active layer may be formed by stacking an n-type semiconductor and a p-type semiconductor.

In addition to the active layer, the light-receiving device may further include a layer containing any of a substance with a high hole-transport property, a substance with a high electron-transport property, a substance with a bipolar property (a substance with a high electron-transport property and a high hole-transport property), and the like. Without limitation to the above, the light-receiving device may further include a layer containing a substance with a high hole-injection property, a hole-blocking material, a material with a high electron-injection property, an electron-blocking material, and the like.

Either a low molecular compound or a high molecular compound can be used in the light-receiving device, and an inorganic compound may also be included. Each layer included in the light-receiving device can be formed by an evaporation method (including a vacuum evaporation method), a transfer method, a printing method, an inkjet method, a coating method, or the like.

As the hole-transport material, a high molecular compound such as poly(3,4-ethylenedioxythiophene)/poly(styrenesulfonic acid) (PEDOT/PSS), or an inorganic compound such as a molybdenum oxide or copper iodide (CuI) can be used, for example. As the electron-transport material, an inorganic compound such as a zinc oxide (ZnO) can be used.

For the active layer, a high molecular compound such as poly[[4,8-bis[5-(2-ethylhexyl)-2-thienyl]benzo[1,2-b:4,5-b']dithiophene-2,6-diyl]-2,5-thiophenediyl[5,7-bis(2-ethylhexyl)-4,8-dioxo-4H,8H-benzo[1,2-c:4,5-c']dithiophene-1,3-diyl]] polymer (abbreviation: PBDB-T) or a PBDB-T derivative, which functions as a donor, can be used. For example, a method in which an acceptor material is dispersed to PBDB-T or a PBDB-T derivative can be used.

The active layer may contain a mixture of three or more kinds of materials. For example, a third material may be mixed with an n-type semiconductor material and a p-type semiconductor material in order to extend the wavelength range. The third material may be a low molecular compound or a high molecular compound.

The display device can sense the touch or approach of an object while displaying an image because the pixel included in the display device includes the light-emitting device and the light-receiving device and thus has a light-receiving function. For example, all the subpixels included in the display device can display an image; alternatively, some of the subpixels can emit light as a light source and the other subpixels can display an image.

In the display device of one embodiment of the present invention, the light-emitting devices are arranged in a matrix in a display portion, and an image can be displayed on the display portion. Furthermore, the light-receiving devices are arranged in a matrix in the display portion, and the display portion has one or both of an image capturing function and a sensing function in addition to an image displaying function. The display portion can be used as an image sensor or a touch sensor. That is, by sensing light with the display portion, an image can be captured or an approach or touch of an object (e.g., a finger, a hand, or a pen) can be sensed. Furthermore, in the display device according to one embodiment of the present invention, the light-emitting devices can be used as a light source of the sensor. Accordingly, a light-receiving portion and a light source do not need to be provided separately from the display device; hence, the number of components of an electronic device can be reduced.

In the display device of one embodiment of the present invention, when an object reflects (or scatters) light emitted from the light-emitting device included in the display portion, the light-receiving device can sense reflected light (or scattered light); thus, image capturing or touch sensing is possible even in a dark place.

In the case where the light-receiving devices are used as the image sensor, the display device can capture an image with use of the light-receiving devices. For example, the display device of this embodiment can be used as a scanner.

For example, data on biological information such as a fingerprint or a palm print can be obtained with use of the image sensor. That is, a biometric authentication sensor can be incorporated in the display device. When the display device incorporates a biometric authentication sensor, the number of components of an electronic device can be reduced as compared to the case where a biometric authentication sensor is provided separately from the display device; thus, the size and weight of the electronic device can be reduced.

In the case where the light-receiving devices are used as the touch sensor, the display device can sense an approach or touch of an object with use of the light-receiving devices.

Pixels illustrated in FIG. 25A to FIG. 25D each include the subpixel G, the subpixel B, the subpixel R, and a subpixel PS.

Figure 25A:
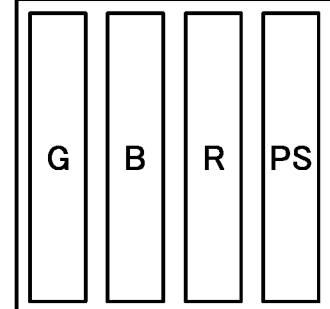
FIG. 25A to FIG. 25D are top views illustrating examples of a pixel.
Figure 25B:
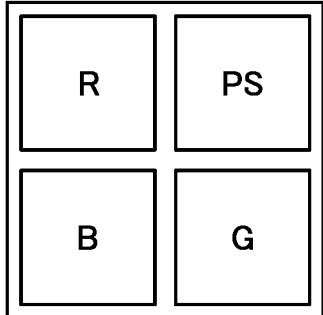

The pixel illustrated in FIG. 25A employs stripe arrangement. The pixel illustrated in FIG. 25B employs matrix arrangement.

Figure 25C:
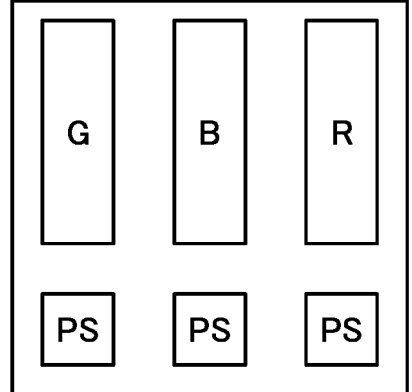
Figure 25D:
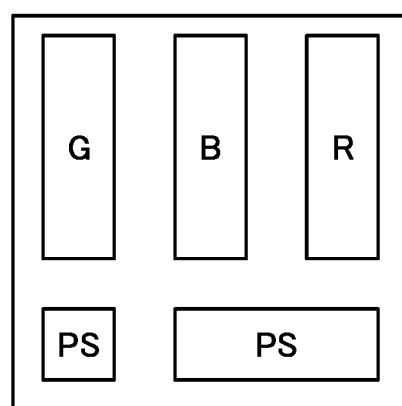

FIG. 25C and FIG. 25D illustrate an example in which one pixel is provided in two rows and three columns. Three subpixels (the subpixel G, the subpixel B, and the subpixel R) are provided in the upper row (first row). In FIG. 25C, three subpixels PS are provided in the lower row (second row). In FIG. 25D, two subpixels PS are provided in the lower row (second row). Matching the positions of the subpixels in the upper row and the lower row as illustrated in FIG. 25C enables dust and the like that would be produced in the manufacturing process to be removed efficiently. Accordingly, a display device that has high display quality can be provided. Note that the layout of the subpixels is not limited to the structures illustrated in FIG. 25A to FIG. 25D.

Each of the subpixel R, the subpixel G, and the subpixel B includes a light-emitting device that emits white light. In each of the subpixel R, the subpixel G, and the subpixel B, the corresponding coloring layer is provided to overlap with the light-emitting device.

The subpixel PS includes the light-receiving device. The wavelength of light sensed by the subpixel PS and is not particularly limited.

The light-receiving device included in the subpixel PS preferably senses visible light, and preferably senses one or more of blue light, violet light, bluish violet light, green light, yellowish green light, yellow light, orange light, red light, and the like. The light-receiving device included in the subpixel PS may sense infrared light.

Figure 25E:
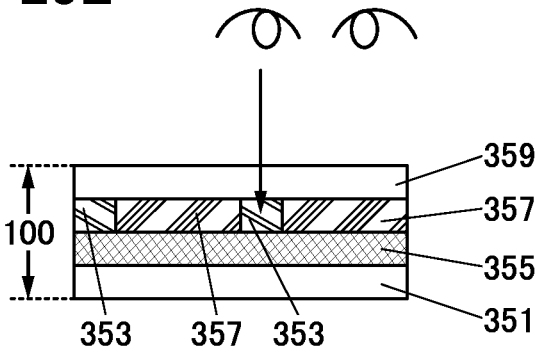
FIG. 25E is a cross-sectional view illustrating an example of a display device.

The display device 100 illustrated in FIG. 25E includes a layer 353 including a light-receiving device, a functional layer 355, and a layer 357 including a light-emitting device, between a substrate 351 and a substrate 359.

The functional layer 355 includes a circuit for driving a light-receiving device and a circuit for driving a light-emitting device. A switch, a transistor, a capacitor, a resistor, a wiring, a terminal, and the like can be provided in the functional layer 355. Note that in the case where the light-emitting device and the light-receiving device are driven by a passive-matrix method, a structure not provided with a switch and a transistor may be employed.

For example, as illustrated in FIG. 25E, light emitted from the light-emitting device in the layer 357 including light-emitting devices is reflected by a human eye or his/her periphery, whereby the light-receiving device in the layer 353 including light-receiving devices senses the reflected light. Accordingly, information of the periphery, surface, or inside of the human eye (e.g., the number of blinks, the movement of an eyeball, and the movement of an eyelid) can be detected.

This embodiment can be combined with the other embodiments as appropriate.

Embodiment 4

In this embodiment, a display device of one embodiment of the present invention will be described with reference to FIG. 26 to FIG. 31.

The display device in this embodiment can be a high-resolution display device. Accordingly, the display device in this embodiment can be used for display portions of information terminals (wearable devices) such as watch-type and bracelet-type information terminals and display portions of wearable devices capable of being worn on the head, such as a VR device like a head-mounted display and a glasses-type AR device.

[Display Module]

Figure 26A:
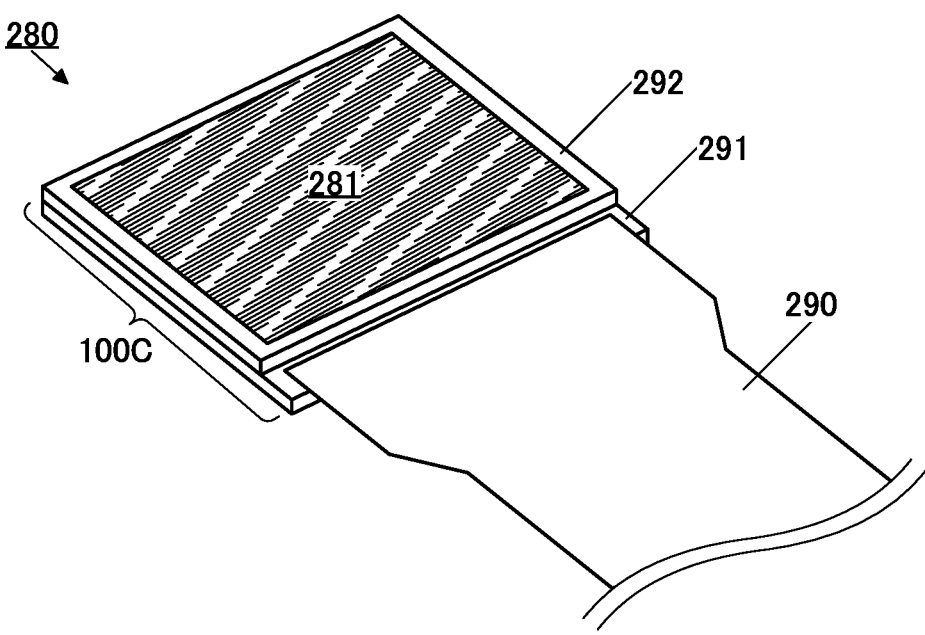
FIG. 26A and FIG. 26B are perspective views illustrating an example of a display module.

FIG. 26A is a perspective view of a display module 280. The display module 280 includes a display device 100C and an FPC 290. Note that the display device included in the display module 280 is not limited to the display device 100C and may be any of a display device 100D to a display device 100G described later.

The display module 280 includes a substrate 291 and a substrate 292. The display module 280 includes a display portion 281. The display portion 281 is a region of the display module 280 where an image is displayed, and is a region where light emitted from pixels provided in a pixel portion 284 described later can be seen.

Figure 26B:
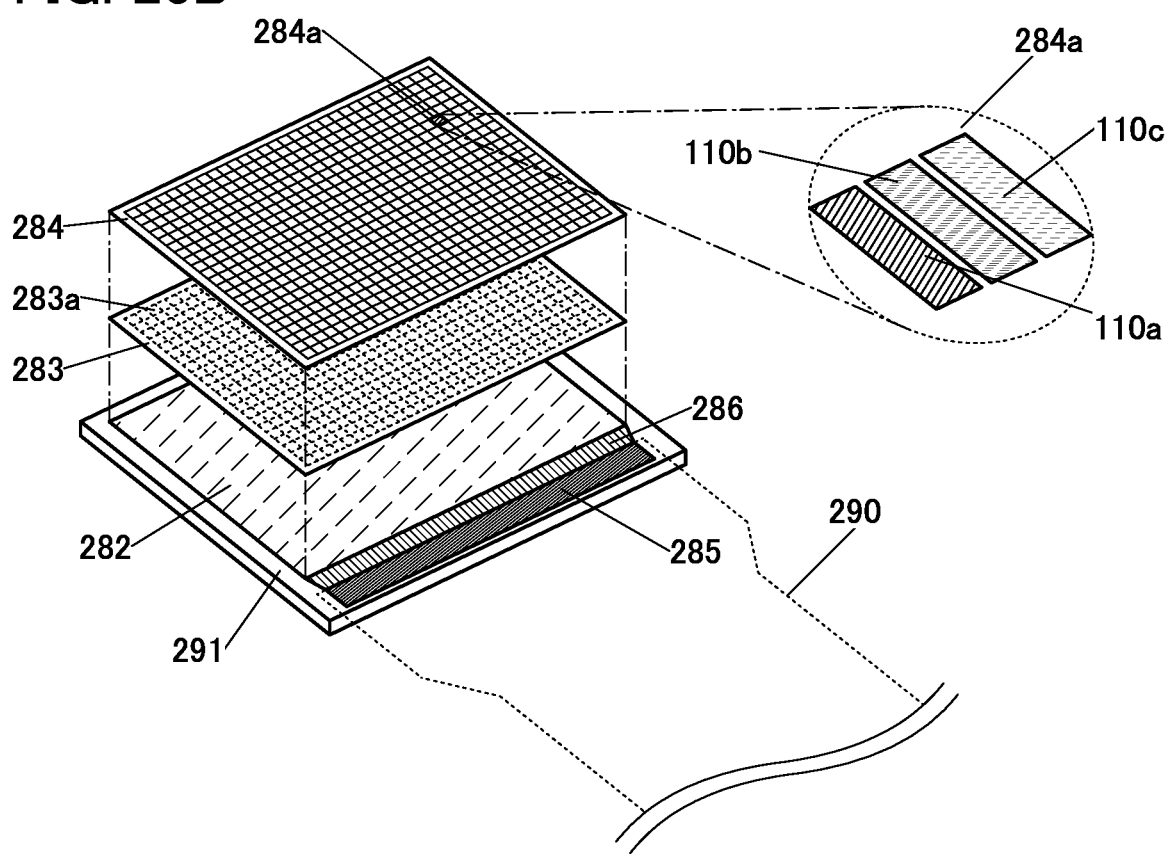

FIG. 26B is a perspective view schematically illustrating a structure on the substrate 291 side. Over the substrate 291, a circuit portion 282, a pixel circuit portion 283 over the circuit portion 282, and the pixel portion 284 over the pixel circuit portion 283 are stacked. A terminal portion 285 to be connected to the FPC 290 is provided in a portion that is over the substrate 291 and does not overlap with the pixel portion 284. The terminal portion 285 and the circuit portion 282 are electrically connected to each other through a wiring portion 286 formed of a plurality of wirings.

The pixel portion 284 includes a plurality of pixels 284a arranged periodically. An enlarged view of one pixel 284a is illustrated on the right side in FIG. 26B. The pixel 284a includes the subpixel 110a, the subpixel 110b, and the subpixel 110c. The foregoing embodiment can be referred to for the structures of the subpixel 110a, the subpixel 110b, and the subpixel 110c and their surroundings. The plurality of subpixels can employ stripe arrangement as illustrated in FIG. 26B. Alternatively, a variety of arrangement methods of light-emitting devices, such as a delta pattern or a PenTile pattern can be employed.

The pixel circuit portion 283 includes a plurality of pixel circuits 283a arranged periodically.

One pixel circuit 283a is a circuit that controls light emission of three light-emitting devices included in one pixel 284a. One pixel circuit 283a may be provided with three circuits each of which controls light emission of one light-emitting device. For example, the pixel circuit 283a can include at least one selection transistor, one current control transistor (driving transistor), and a capacitor for one light-emitting device. In this case, a gate signal is input to a gate of the selection transistor, and a source signal is input to one of a source and a drain of the selection transistor. Thus, an active-matrix display device is achieved.

The circuit portion 282 includes a circuit for driving the pixel circuits 283a in the pixel circuit portion 283. For example, one or both of a gate line driver circuit and a source line driver circuit are preferably included. In addition, at least one of an arithmetic circuit, a memory circuit, a power supply circuit, and the like may be included.

The FPC 290 functions as a wiring for supplying a video signal, a power supply potential, or the like to the circuit portion 282 from the outside. An IC may be mounted on the FPC 290.

The display module 280 can have a structure in which one or both of the pixel circuit portion 283 and the circuit portion 282 are stacked below the pixel portion 284; hence, the aperture ratio (effective display area ratio) of the display portion 281 can be significantly high. For example, the aperture ratio of the display portion 281 can be greater than or equal to 40% and less than 100%, preferably greater than or equal to 50% and less than or equal to 95%, further preferably greater than or equal to 60% and less than or equal to 95%. Furthermore, the pixels 284a can be arranged extremely densely and thus the display portion 281 can have extremely high resolution. For example, the pixels 284a are preferably arranged in the display portion 281 with a resolution greater than or equal to 2000 ppi, preferably greater than or equal to 3000 ppi, further preferably greater than or equal to 5000 ppi, still further preferably greater than or equal to 6000 ppi, and less than or equal to 20000 ppi or less than or equal to 30000 ppi.

Such a display module 280 has extremely high resolution, and thus can be suitably used for a VR device such as a head-mounted display or a glasses-type AR device. For example, even with a structure in which the display portion of the display module 280 is seen through a lens, pixels of the extremely-high-resolution display portion 281 included in the display module 280 are prevented from being perceived when the display portion is enlarged by the lens, so that display providing a high sense of immersion can be performed. Without being limited thereto, the display module 280 can be suitably used for electronic devices including a relatively small display portion. For example, the display module 280 can be suitably used in a display portion of a wearable electronic device such as a wrist watch.

[Display Device 100C]

Figure 27:
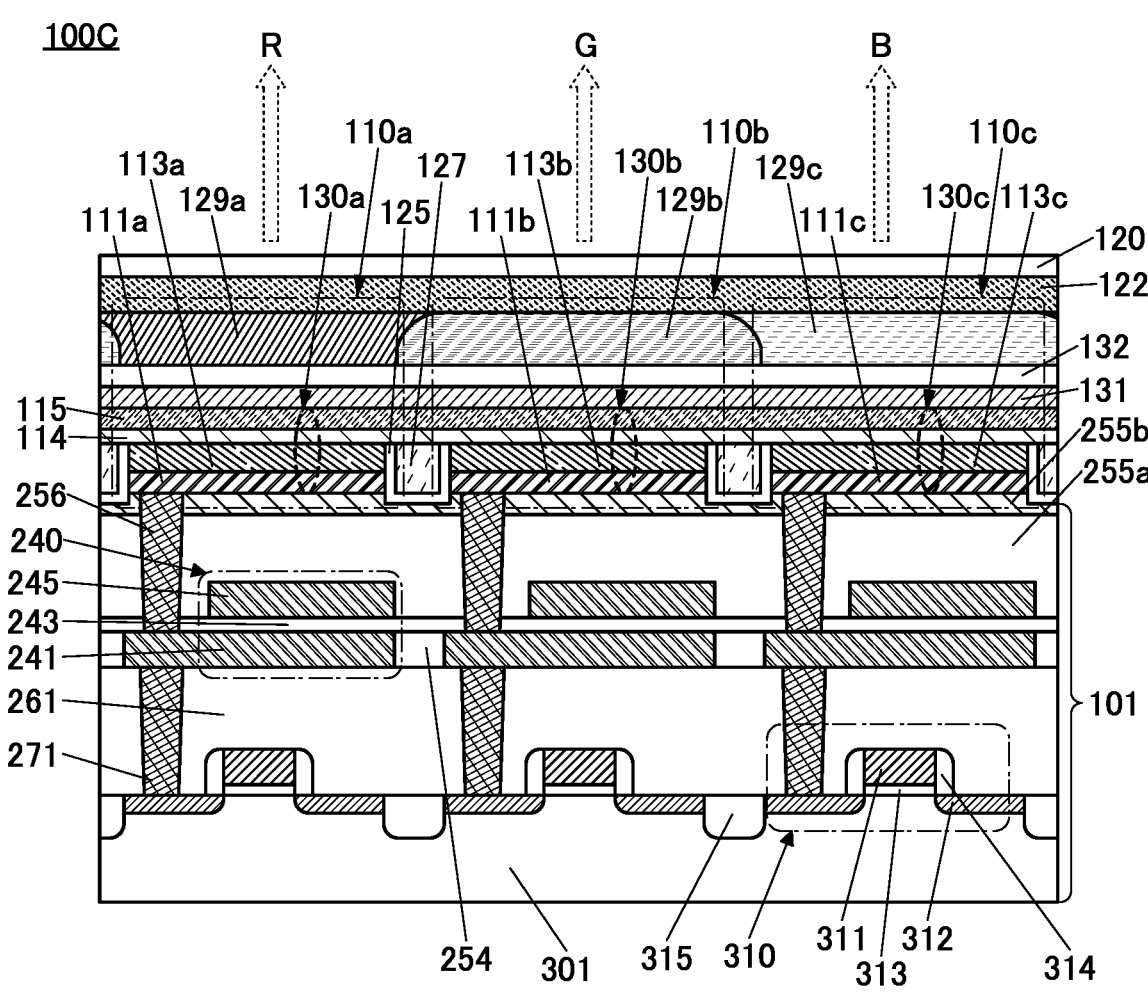
FIG. 27 is a cross-sectional view illustrating an example of a display device.

The display device 100C illustrated in FIG. 27 includes a substrate 301, the subpixels 110a, 110b, and 110c, a capacitor 240, and a transistor 310. The subpixel 110a includes the light-emitting device 130a and the coloring layer 129a. The subpixel 110b includes the light-emitting device 130b and the coloring layer 129b. The subpixel 110c includes the light-emitting device 130c and the coloring layer 129c.

The substrate 301 corresponds to the substrate 291 illustrated in FIG. 26A and FIG. 26B. The layer 101 including a transistor includes a stacked-layer structure including the substrate 301 and components thereover up to the insulating layer 255b.

The transistor 310 is a transistor including a channel formation region in the substrate 301. As the substrate 301, a semiconductor substrate such as a single crystal silicon substrate can be used, for example. The transistor 310 includes part of the substrate 301, a conductive layer 311, low-resistance regions 312, an insulating layer 313, and an insulating layer 314. The conductive layer 311 functions as a gate electrode. The insulating layer 313 is positioned between the substrate 301 and the conductive layer 311 and functions as a gate insulating layer. The low-resistance regions 312 are regions where the substrate 301 is doped with an impurity, and function as one of a source and a drain. The insulating layer 314 is provided to cover a side surface of the conductive layer 311.

An element isolation layer 315 is provided between the two adjacent transistors 310 to be embedded in the substrate 301.

An insulating layer 261 is provided to cover the transistor 310, and the capacitor 240 is provided over the insulating layer 261.

The capacitor 240 includes a conductive layer 241, a conductive layer 245, and an insulating layer 243 positioned therebetween. The conductive layer 241 functions as one electrode of the capacitor 240, the conductive layer 245 functions as the other electrode of the capacitor 240, and the insulating layer 243 functions as the dielectric of the capacitor 240.

The conductive layer 241 is provided over the insulating layer 261 and is embedded in an insulating layer 254. The conductive layer 241 is electrically connected to one of a source and a drain of the transistor 310 through a plug 271 embedded in the insulating layer 261. The insulating layer 243 is provided to cover the conductive layer 241. The conductive layer 245 is provided in a region overlapping with the conductive layer 241 with the insulating layer 243 therebetween.

An insulating layer 255a is provided to cover the capacitor 240. The insulating layer 255b is provided over the insulating layer 255a. The light-emitting devices 130a, 130b, and 130c and the like are provided over the insulating layer 255b. The light-emitting device 130a illustrated in FIG. 27 is different from the light-emitting device 130a in FIG. 17A in that the conductive layer 126a functioning as an optical adjustment layer is not provided. The light-emitting device 130b illustrated in FIG. 27 is different from the light-emitting device 130b illustrated in FIG. 17A in that the conductive layer 126b functioning as an optical adjustment layer is not provided. The light-emitting device 130c illustrated in FIG. 27 is different from the light-emitting device 130c illustrated in FIG. 17A in that the conductive layer 126c functioning as an optical adjustment layer is not provided.

Side surfaces of the pixel electrodes 111a, 111b, and 111c, the first layer 113a, the second layer 113b, and the third layer 113c are covered with the insulating layers 125 and 127. The fifth layer 114 is provided over the first layer 113a, the second layer 113b, the third layer 113c, the insulating layer 125, and the insulating layer 127. The common electrode 115 is provided over the fifth layer 114. The protective layer 131 is provided over the light-emitting devices 130a, 130b, and 130c. The protective layer 132 is provided over the protective layer 131. The coloring layers 129a, 129b, and 129c are provided over the protective layer 132. The substrate 120 is attached above the coloring layers 129a, 129b, and 129c with the resin layer 122. The substrate 120 corresponds to the substrate 292 illustrated in FIG. 26A.

As each of the insulating layers 255a and 255b, a variety of inorganic insulating films such as an oxide insulating film, a nitride insulating film, an oxynitride insulating film, and a nitride oxide insulating film can be suitably used. For the insulating layer 255a, an oxide insulating film or an oxynitride insulating film, such as a silicon oxide film, a silicon oxynitride film, or an aluminum oxide film, is preferably used. For the insulating layer 255b, a nitride insulating film or a nitride oxide insulating film, such as a silicon nitride film or a silicon nitride oxide film, is preferably used. More specifically, it is preferable that a silicon oxide film be used for the insulating layer 255a and that a silicon nitride film be used for the insulating layer 255b. The insulating layer 255b preferably has a function of an etching protective film. Alternatively, a nitride insulating film or a nitride oxide insulating film may be used for the insulating layer 255a, and an oxide insulating film or an oxynitride insulating film may be used for the insulating layer 255b. Although this embodiment shows an example in which a depression portion is provided in the insulating layer 255b, a depression portion is not necessarily provided in the insulating layer 255b.

The pixel electrode of each of the light-emitting devices is electrically connected to one of the source and the drain of the transistor 310 through a plug 256 embedded in the insulating layers 255a and 255b, the conductive layer 241 embedded in the insulating layer 254, and the plug 271 embedded in the insulating layer 261. A top surface of the insulating layer 255b and a top surface of the plug 256 are level with or substantially level with each other. A variety of conductive materials can be used for the plugs.

[Display Device 100D]

Figure 28:
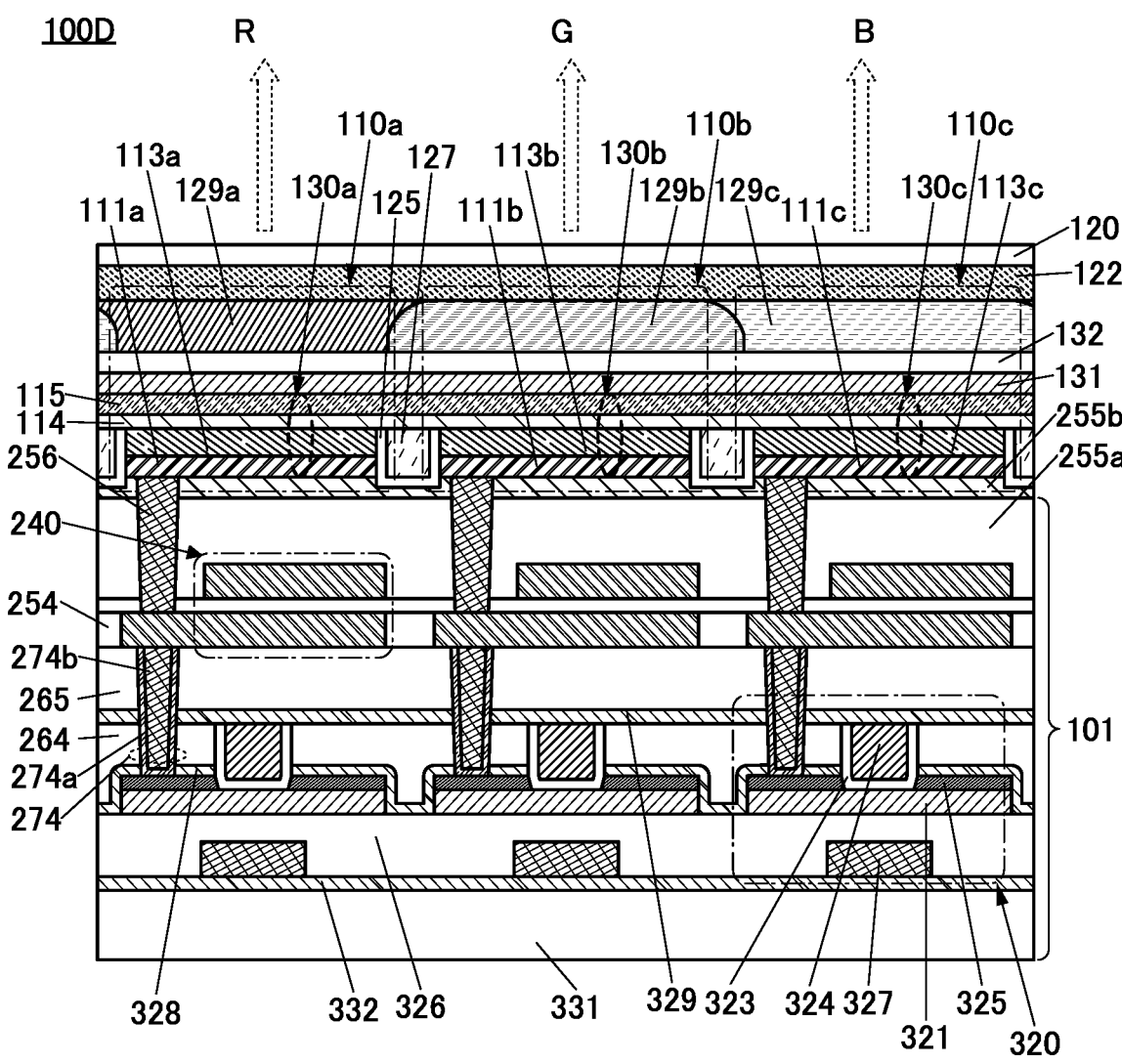
FIG. 28 is a cross-sectional view illustrating an example of a display device.

The display device 100D illustrated in FIG. 28 differs from the display device 100C mainly in a structure of a transistor. Note that portions similar to those in the display device 100C are not described in some cases.

A transistor 320 is a transistor (an OS transistor) in which a metal oxide (also referred to as an oxide semiconductor) is employed in a semiconductor layer where a channel is formed.

The transistor 320 includes a semiconductor layer 321, an insulating layer 323, a conductive layer 324, a pair of conductive layers 325, an insulating layer 326, and a conductive layer 327.

The substrate 331 corresponds to the substrate 291 in FIG. 26A and FIG. 26B. The layer 101 including a transistor includes a stacked-layer structure including the substrate 331 and components thereover up to the insulating layer 255b. As the substrate 331, an insulating substrate or a semiconductor substrate can be used.

An insulating layer 332 is provided over the substrate 331. The insulating layer 332 functions as a barrier layer that prevents diffusion of impurities such as water or hydrogen from the substrate 331 into the transistor 320 and release of oxygen from the semiconductor layer 321 to the insulating layer 332 side. As the insulating layer 332, for example, a film through which hydrogen or oxygen is less likely to diffuse than in a silicon oxide film, such as an aluminum oxide film, a hafnium oxide film, or a silicon nitride film, can be used.

The conductive layer 327 is provided over the insulating layer 332, and the insulating layer 326 is provided to cover the conductive layer 327. The conductive layer 327 functions as a first gate electrode of the transistor 320, and part of the insulating layer 326 functions as a first gate insulating layer. An oxide insulating film such as a silicon oxide film is preferably used as at least part of the insulating layer 326 that is in contact with the semiconductor layer 321. The top surface of the insulating layer 326 is preferably planarized.

It is preferable that the conductive layer 327 be a single conductive layer or two or more conductive layers stacked. In the case where the conductive layer 327 is two or more conductive layers stacked, of the two conductive layers, the conductive layer in contact with a bottom and side surface of an opening provided in the insulating layer 326 is preferably formed using a conductive material having a function of inhibiting diffusion of oxygen or an impurity such as water or hydrogen. Examples of such a conductive material include titanium, titanium nitride, tantalum, tantalum nitride, ruthenium, and ruthenium oxide. The above structure can inhibit diffusion of an impurity such as water or hydrogen into the semiconductor layer 321.

It is preferable that the insulating layer 326 be a single inorganic insulating film or two or more inorganic insulating films stacked. In the case where the insulating layer 326 is two or more inorganic insulating films stacked, one of the inorganic insulating films included in the insulating layer 326 preferably functions as a barrier layer preventing diffusion of an impurity such as water or hydrogen from the substrate 331 side into the transistor 320. As the inorganic insulating film, an insulating film similar to the insulating layer 328 can be used.

The semiconductor layer 321 is provided over the insulating layer 326. The semiconductor layer 321 preferably includes a metal oxide (also referred to as an oxide semiconductor) film having semiconductor characteristics. The semiconductor layer 321 may have a single-layer structure or a stacked-layer structure of a metal oxide that can be used as a semiconductor layer of the transistor described in Embodiment 3, for example. A material that can be suitably used for the semiconductor layer 321 will be described in detail later.

The pair of conductive layers 325 are provided over and in contact with the semiconductor layer 321 and function as a source electrode and a drain electrode.

An insulating layer 328 is provided to cover the top and side surfaces of the pair of conductive layers 325, a side surface of the semiconductor layer 321, and the like, and an insulating layer 264 is provided over the insulating layer 328. The insulating layer 328 functions as a barrier layer that prevents diffusion of impurities such as water or hydrogen from the insulating layer 264 and the like into the semiconductor layer 321 and release of oxygen from the semiconductor layer 321. As the insulating layer 328, an insulating film similar to the insulating layer 332 can be used.

An opening reaching the semiconductor layer 321 is provided in the insulating layer 328 and the insulating layer 264. The insulating layer 323 that is in contact with the side surfaces of the insulating layer 264, the insulating layer 328, and the conductive layer 325 and the top surface of the semiconductor layer 321, and the conductive layer 324 are embedded in the opening. The conductive layer 324 functions as a second gate electrode, and the insulating layer 323 functions as a second gate insulating layer.

As the insulating layer 323, for example, an inorganic insulating film such as a silicon oxide film or a silicon oxynitride film can be used. Note that the insulating layer 323 is not necessarily a single inorganic insulating film but may be two or more inorganic insulating films stacked. For example, an aluminum oxide film, a hafnium oxide film, a silicon nitride film, or the like may be provided in the form of a single layer or stacked layers on the side in contact with the conductive layer 324. Thus, oxidation of the conductive layer 324 can be inhibited. Furthermore, for example, an aluminum oxide film or a hafnium oxide film may be provided on the side in contact with the insulating layer 264, the insulating layer 328, and the conductive layer 325. In this case, it is possible to inhibit release of oxygen from the semiconductor layer 321, excessive supply of oxygen to the semiconductor layer 321, oxidation of the conductive layer 325, and the like.

The top surface of the conductive layer 324, the top surface of the insulating layer 323, and the top surface of the insulating layer 264 are planarized so that they are level or substantially level with each other, and the insulating layer 329 and the insulating layer 265 are provided to cover these layers.

The conductive layer 327 and the conductive layer 324 preferably overlap with each other with an insulator therebetween on the outer side of the side surface of the semiconductor layer 321 in the channel width direction. With this structure, the channel formation region of the semiconductor layer 321 can be electrically surrounded by the electric field of the conductive layer 327 functioning as the first gate electrode and the electric field of the conductive layer 324 functioning as the second gate electrode. In this specification, a transistor structure in which the channel formation region is electrically surrounded by the electric fields of the first gate electrode and the second gate electrode is referred to as a surrounded channel (S-channel) structure.

In this specification and the like, a transistor having the S-channel structure refers to a transistor having a structure in which a channel formation region is electrically surrounded by the electric fields of a pair of gate electrodes. The S-channel structure disclosed in this specification and the like is different from a Fin-type structure and a planar structure. With the S-channel structure, resistance to a short-channel effect can be enhanced, that is, a transistor in which a short-channel effect is less likely to occur can be provided.

When the transistor 320 becomes normally-off and has the above-described S-channel structure, the channel formation region can be electrically surrounded. Accordingly, the transistor 320 can be regarded as having a GAA (Gate All Around) structure or an LGAA (Lateral Gate All Around) structure. When the transistor 320 has the S-channel structure, the GAA structure, or the LGAA structure, the channel formation region that is formed at the interface between the semiconductor layer 321 and the gate insulating film or in the vicinity of the interface can be formed in the entire bulk of the semiconductor layer 321. Accordingly, the density of current flowing in the transistor can be improved, and it can be expected to improve the on-state current of the transistor or increase the field-effect mobility of the transistor.

The insulating layer 264 and the insulating layer 265 each function as an interlayer insulating layer. The insulating layer 329 functions as a barrier layer that prevents diffusion of impurities such as water or hydrogen from the insulating layer 265 and the like into the transistor 320. As the insulating layer 329, an insulating film similar to the insulating layer 328 and the insulating layer 332 can be used.

A plug 274 electrically connected to one of the pair of conductive layers 325 is provided to be embedded in the insulating layer 265, the insulating layer 329, and the insulating layer 264. Here, the plug 274 preferably includes a conductive layer 274a that covers the side surfaces of openings formed in the insulating layer 265, the insulating layer 329, the insulating layer 264, and the insulating layer 328 and part of the top surface of the conductive layer 325, and a conductive layer 274b in contact with the top surface of the conductive layer 274a. In this case, a conductive material through which hydrogen and oxygen are less likely to diffuse is preferably used for the conductive layer 274a. This structure inhibits an impurity such as water or hydrogen from entering the semiconductor layer 321 from the insulating layer 264 and the like through the plug 274. Furthermore, the structure inhibits oxygen contained in the insulating layer 264 from being absorbed by the plug 274.

An insulating layer may be provided in contact with the side surface of the plug 274. That is, a structure may be employed in which the insulating layer is provided in contact with the inner wall of the opening in the insulating layer 265, the insulating layer 329, and the insulating layer 264 and the plug 274 is provided in contact with the side surface of the insulating layer and part of the top surface of the conductive layer 325.

The structure from the insulating layer 254 to the substrate 120 in the display device 100D is similar to that in the display device 100C.

[Display Device 100E]

Figure 29:
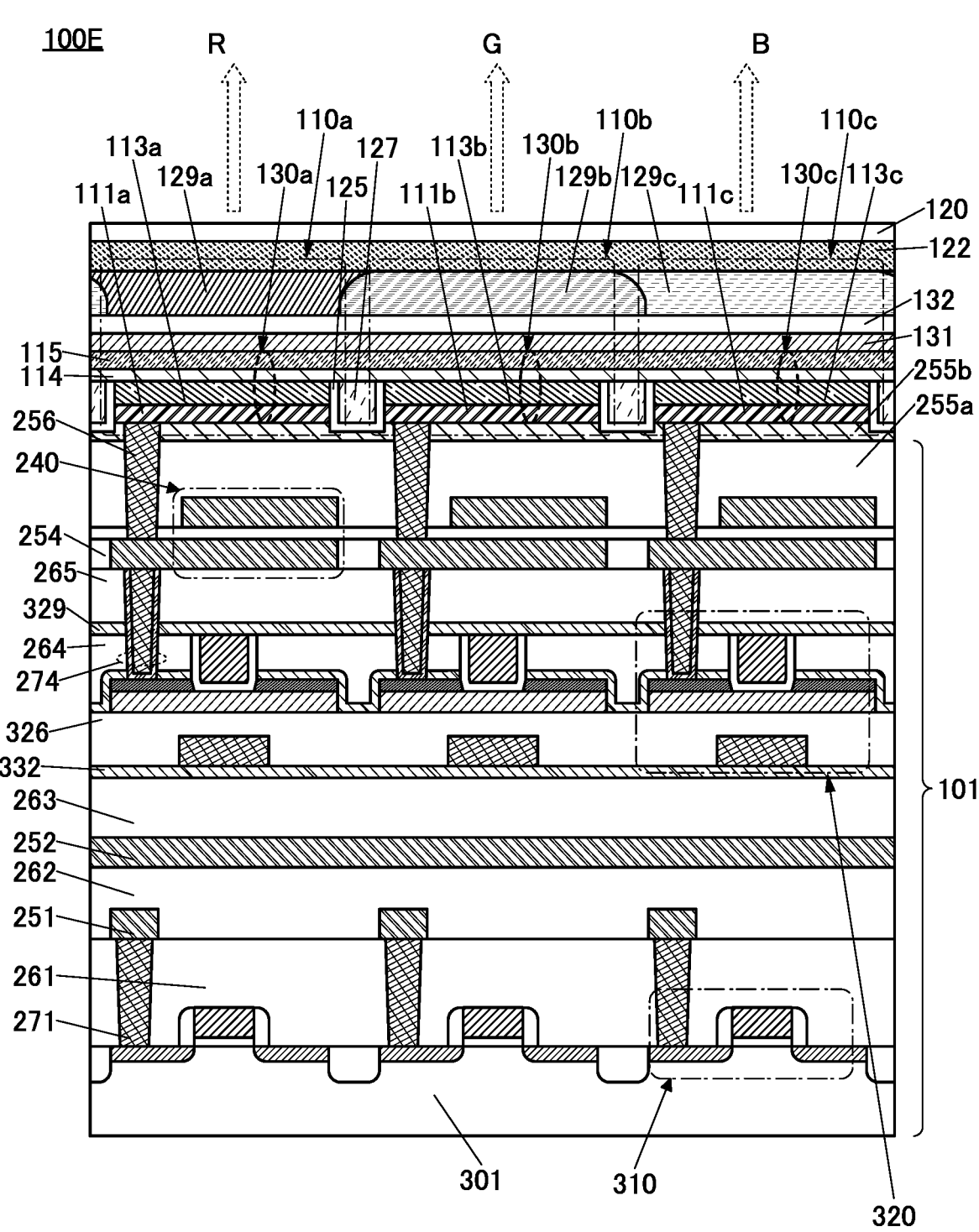
FIG. 29 is a cross-sectional view illustrating an example of a display device.

The display device 100E illustrated in FIG. 29 has a structure in which the transistor 310 having a channel formed in the substrate 301 and the transistor 320 including a metal oxide in a semiconductor layer where a channel is formed are stacked. Note that portions similar to those in the display devices 100C and 100D are not described in some cases.

The insulating layer 261 is provided to cover the transistor 310, and a conductive layer 251 is provided over the insulating layer 261. An insulating layer 262 is provided to cover the conductive layer 251, and a conductive layer 252 is provided over the insulating layer 262. The conductive layer 251 and the conductive layer 252 each function as a wiring. An insulating layer 263 and the insulating layer 332 are provided to cover the conductive layer 252, and the transistor 320 is provided over the insulating layer 332. The insulating layer 265 is provided to cover the transistor 320, and the capacitor 240 is provided over the insulating layer 265. The capacitor 240 and the transistor 320 are electrically connected to each other through the plug 274.

The transistor 320 can be used as a transistor included in the pixel circuit. The transistor 310 can be used as a transistor included in the pixel circuit or a transistor included in a driver circuit (a gate line driver circuit or a source line driver circuit) for driving the pixel circuit. The transistor 310 and the transistor 320 can also be used as transistors included in a variety of circuits such as an arithmetic circuit and a memory circuit.

With such a structure, not only the pixel circuit but also the driver circuit and the like can be formed directly under the light-emitting devices; thus, the display device can be downsized as compared with the case where the driver circuit is provided around a display region.

[Display Device 100F]

Figure 30:
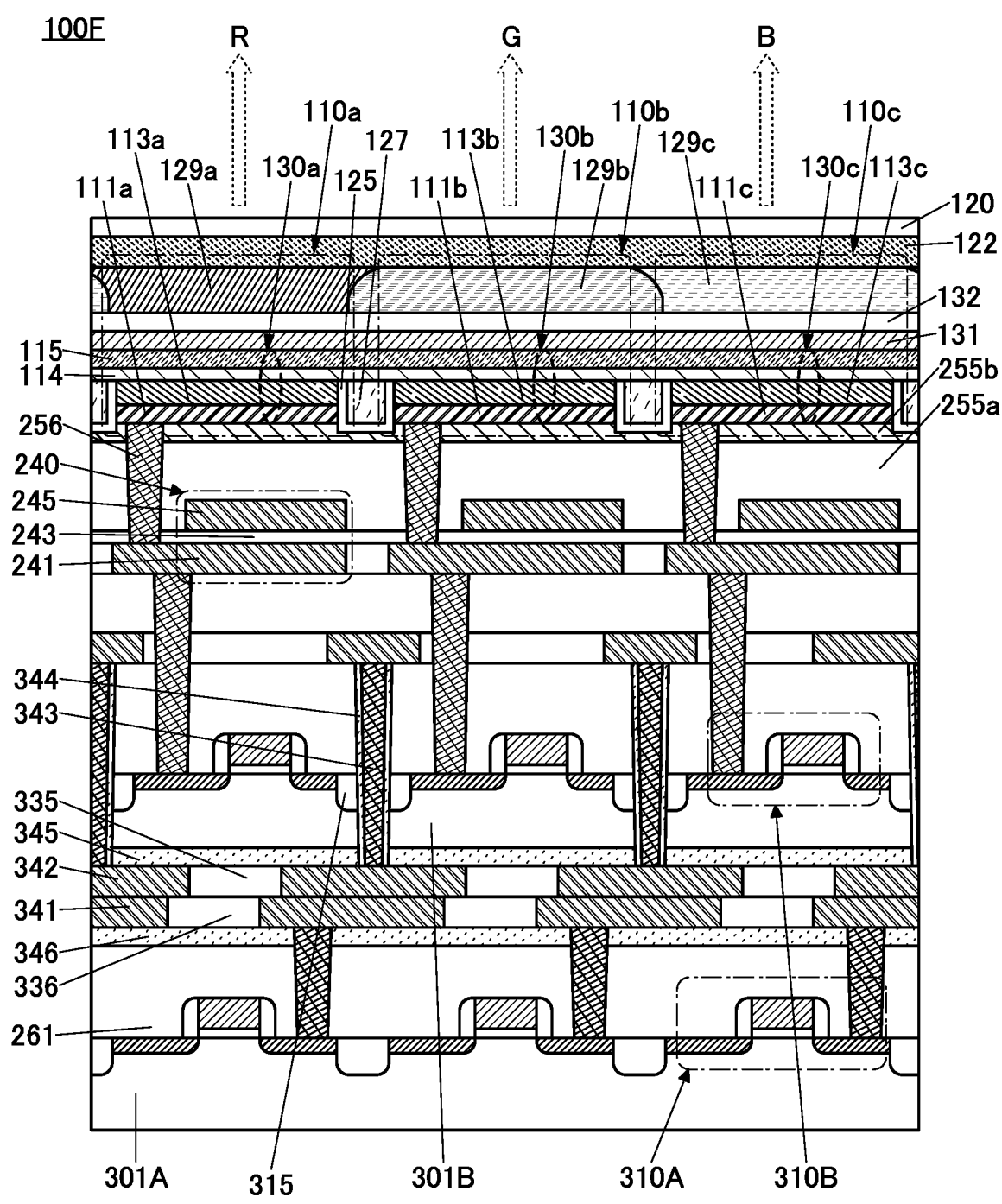
FIG. 30 is a cross-sectional view illustrating an example of a display device.

The display device 100F illustrated in FIG. 30 has a structure in which a transistor 310A and a transistor 310B each having a channel formed in a semiconductor substrate are stacked.

In the display device 100F, a structure is employed in which a substrate 301B provided with the transistor 310B, the capacitor 240, and the light-emitting devices is attached to a substrate 301A provided with the transistor 310A.

Here, an insulating layer 345 is preferably provided on the bottom surface of the substrate 301B. An insulating layer 346 is preferably provided over the insulating layer 261 over the substrate 301A. The insulating layers 345 and 346 function as protective layers and can inhibit diffusion of impurities into the substrate 301B and the substrate 301A. For the insulating layers 345 and 346, an inorganic insulating film that can be used for the protective layers 131 and 132 or an insulating layer 332 can be used.

The substrate 301B is provided with a plug 343 that penetrates the substrate 301B and the insulating layer 345. An insulating layer 344 is preferably provided to cover the side surface of the plug 343. The insulating layer 344 functions as a protective layer and can inhibit diffusion of impurities into the substrate 301B. As the insulating layer 344, an inorganic insulating film that can be used as the protective layers 131 and 132 or the insulating layer 332 can be used.

A conductive layer 342 is provided under the insulating layer 345 on the rear surface of the substrate 301B (the surface opposite to the substrate 120). The conductive layer 342 is preferably provided to be embedded in the insulating layer 335. The bottom surfaces of the conductive layer 342 and the insulating layer 335 are preferably planarized. Here, the conductive layer 342 is electrically connected to the plug 343.

In contrast, over the substrate 301A, a conductive layer 341 is provided over the insulating layer 346. The conductive layer 341 is preferably provided to be embedded in the insulating layer 336. The top surfaces of the conductive layer 341 and the insulating layer 336 are preferably planarized.

The conductive layer 341 and the conductive layer 342 are bonded to each other, whereby the substrate 301A and the substrate 301B are electrically connected to each other.

Here, improving the flatness of a plane formed by the conductive layer 342 and the insulating layer 335 and a plane formed by the conductive layer 341 and the insulating layer 336 allows the conductive layers 341 and 342 to be bonded to each other favorably.

The conductive layer 341 and the conductive layer 342 are preferably formed using the same conductive material. For example, a metal film containing an element selected from Al, Cr, Cu, Ta, Ti, Mo, and W, a metal nitride film containing the above element as a component (a titanium nitride film, a molybdenum nitride film, or a tungsten nitride film), or the like can be used. Copper is particularly preferably used for the conductive layer 341 and the conductive layer 342. Thus, it is possible to employ Cu-to-Cu (copper-to-copper) direct bonding technique (a technique for achieving electrical continuity by connecting Cu (copper) pads).

[Display Device 100G]

Figure 31:
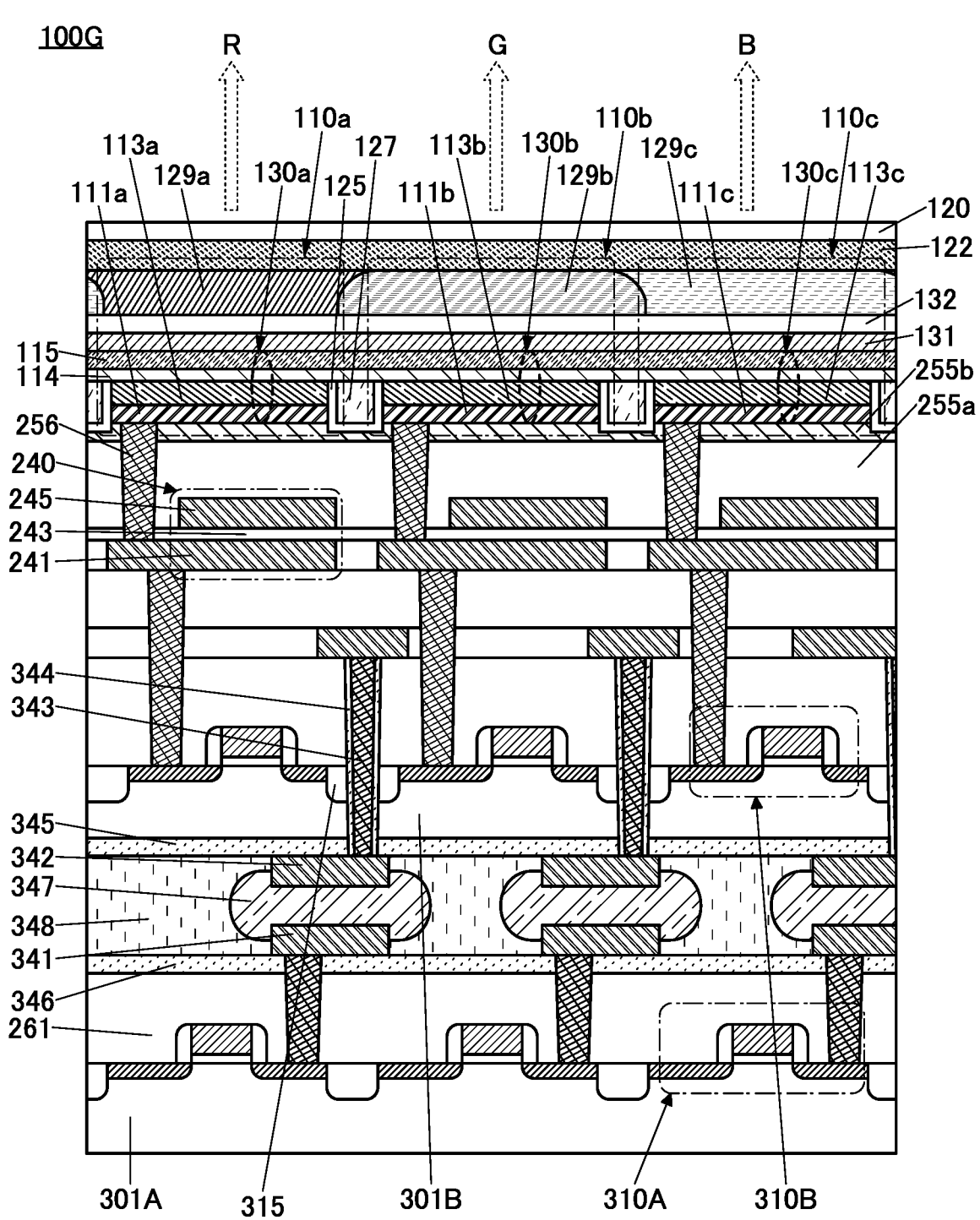
FIG. 31 is a cross-sectional view illustrating an example of a display device.

Although FIG. 30 illustrates an example in which Cu-to-Cu direct bonding is used to bond the conductive layer 341 and the conductive layer 342, the present invention is not limited thereto. As illustrated in FIG. 31, the conductive layer 341 and the conductive layer 342 may be bonded to each other through a bump 347 in the display device 100G.

As illustrated in FIG. 31, providing the bump 347 between the conductive layer 341 and the conductive layer 342 enables the conductive layers 341 and 342 to be electrically connected to each other. The bump 347 can be formed using a conductive material containing gold (Au), nickel (Ni), indium (In), tin (Sn), or the like. For example, solder may be used for the bump 347. An adhesive layer 348 may be provided between the insulating layer 345 and the insulating layer 346. In the case where the bump 347 is provided, the insulating layer 335 and the insulating layer 336 may be omitted.

This embodiment can be combined with the other embodiments as appropriate.

Embodiment 5

In this embodiment, a metal oxide (also referred to as an oxide semiconductor) that can be used in the OS transistor described in the above embodiment will be described.

The metal oxide used in the OS transistor preferably contains at least indium or zinc, and further preferably contains indium and zinc. A metal oxide preferably contains indium, M (M is one or more kinds selected from gallium, aluminum, yttrium, tin, silicon, boron, copper, vanadium, beryllium, titanium, iron, nickel, germanium, zirconium, molybdenum, lanthanum, cerium, neodymium, hafnium, tantalum, tungsten, magnesium, and cobalt), and zinc, for example. In particular, M is preferably one or more kinds selected from gallium, aluminum, yttrium, and tin, and M is further preferably gallium.

The metal oxide can be formed by a sputtering method, a CVD method such as a metal organic chemical vapor deposition (MOCVD) method, an ALD method, or the like.

Hereinafter, an oxide containing indium (In), gallium (Ga), and zinc (Zn) is described as an example of the metal oxide. Note that an oxide containing indium (In), gallium (Ga), and zinc (Zn) may be referred to as an In—Ga—Zn oxide.

<Classification of Crystal Structure>

Amorphous (including a completely amorphous structure), CAAC (c-axis-aligned crystalline), nc (nanocrystalline), CAC (cloud-aligned composite), single crystal, and polycrystalline (poly crystal) structures can be given as examples of a crystal structure of an oxide semiconductor.

A crystal structure of a film or a substrate can be evaluated with an X-ray diffraction (XRD) spectrum. For example, evaluation is possible using an XRD spectrum obtained by GIXD (Grazing-Incidence XRD) measurement. Note that a GIXD method is also referred to as a thin film method or a Seemann-Bohlin method. The XRD spectrum obtained by GIXD measurement may be hereinafter simply referred to as an XRD spectrum.

For example, the XRD spectrum of a quartz glass substrate shows a peak with a substantially bilaterally symmetrical shape. On the other hand, the peak of the XRD spectrum of the In—Ga—Zn oxide film having a crystal structure has a bilaterally asymmetrical shape. The bilaterally asymmetrical peak of the XRD spectrum clearly shows the existence of a crystal in the film or the substrate. In other words, the crystal structure of the film or the substrate cannot be regarded as "amorphous" unless it has a bilaterally symmetrical peak in the XRD spectrum.

A crystal structure of a film or a substrate can also be evaluated with a diffraction pattern obtained by a nanobeam electron diffraction (NBED) method (such a pattern is also referred to as a nanobeam electron diffraction pattern). For example, a halo pattern is observed in the diffraction pattern of the quartz glass substrate, which indicates that the quartz glass substrate is in an amorphous state. Furthermore, not a halo pattern but a spot-like pattern is observed in the diffraction pattern of the In—Ga—Zn oxide film deposited at room temperature. Thus, it is suggested that the In—Ga—Zn oxide film deposited at room temperature is in an intermediate state, which is neither a single crystal nor polycrystal nor an amorphous state, and it cannot be concluded that In—Ga—Zn oxide film is in an amorphous state.

<<Oxide Semiconductor Structure>>

Oxide semiconductors might be classified in a manner different from the above-described one when classified in terms of the structure. Oxide semiconductors are classified into a single crystal oxide semiconductor and a non-single-crystal oxide semiconductor, for example. Examples of the non-single-crystal oxide semiconductor include the CAAC-OS and the nc-OS. Other examples of the non-single-crystal oxide semiconductor include a polycrystalline oxide semiconductor, an amorphous-like oxide semiconductor (a-like OS), and an amorphous oxide semiconductor.

Here, the CAAC-OS, the nc-OS, and the a-like OS are described in detail.

[CAAC-OS]

The CAAC-OS is an oxide semiconductor that has a plurality of crystal regions each of which has c-axis alignment in a particular direction. Note that the particular direction refers to the film thickness direction of a CAAC-OS film, the normal direction of the surface where the CAAC-OS film is formed, or the normal direction of the surface of the CAAC-OS film. The crystal region refers to a region having a periodic atomic arrangement. Note that when an atomic arrangement is regarded as a lattice arrangement, the crystal region also refers to a region with a uniform lattice arrangement. The CAAC-OS has a region where a plurality of crystal regions are connected in the a-b plane direction, and the region has distortion in some cases. Note that distortion refers to a portion where the orientation of a lattice arrangement changes between a region with a uniform lattice arrangement and another region with a uniform lattice arrangement in a region where a plurality of crystal regions are connected. That is, the CAAC-OS is an oxide semiconductor having c-axis alignment and having no clear alignment in the a-b plane direction.

Note that each of the plurality of crystal regions is formed of one or more fine crystals (crystals each of which has a maximum diameter of less than 10 nm). In the case where the crystal region is formed of one fine crystal, the maximum diameter of the crystal region is less than 10 nm. In the case where the crystal region is formed of a large number of fine crystals, the maximum diameter of the crystal region may be approximately several tens of nanometers.

In the case of an In—Ga—Zn oxide, the CAAC-OS tends to have a layered crystal structure (also referred to as a layered structure) in which a layer containing indium (In) and oxygen (hereinafter, an In layer) and a layer containing gallium (Ga), zinc (Zn), and oxygen (hereinafter, a (Ga,Zn) layer) are stacked. Indium and gallium can be replaced with each other. Therefore, indium may be contained in the (Ga,Zn) layer. In addition, gallium may be contained in the In layer. Note that zinc may be contained in the In layer. Such a layered structure is observed as a lattice image in a high-resolution TEM (Transmission Electron Microscope) image, for example.

When the CAAC-OS film is subjected to structural analysis by Out-of-plane XRD measurement with an XRD apparatus using $\theta/2\theta$ scanning, for example, a peak indicating c-axis alignment is detected at $2\theta$ of 31° or around 31°. Note that the position of the peak indicating c-axis alignment (the value of $2\theta$) may change depending on the kind, composition, or the like of the metal element contained in CAAC-OS.

For example, a plurality of bright spots are observed in the electron diffraction pattern of the CAAC-OS film. Note that one spot and another spot are observed point-symmetrically with a spot of the incident electron beam passing through a sample (also referred to as a direct spot) as the symmetric center.

When the crystal region is observed from the particular direction, a lattice arrangement in the crystal region is basically a hexagonal lattice arrangement; however, a unit lattice is not always a regular hexagon and is a non-regular hexagon in some cases. A pentagonal lattice arrangement, a heptagonal lattice arrangement, and the like are included in the distortion in some cases. Note that a clear grain boundary cannot be observed even in the vicinity of the distortion in the CAAC-OS. That is, formation of a grain boundary is inhibited by the distortion of a lattice arrangement. This is probably because the CAAC-OS can tolerate distortion owing to a low density of arrangement of oxygen atoms in the a-b plane direction, an interatomic bond distance changed by substitution of a metal atom, and the like.

A crystal structure in which a clear grain boundary is observed is what is called polycrystal. It is highly probable that the grain boundary becomes a recombination center and traps carriers and thus decreases the on-state current and field-effect mobility of a transistor, for example. Thus, the CAAC-OS in which no clear grain boundary is observed is one of crystalline oxides having a crystal structure suitable for a semiconductor layer of a transistor. Note that Zn is preferably contained to form the CAAC-OS. For example, an In—Zn oxide and an In—Ga—Zn oxide are suitable because they can inhibit generation of a grain boundary as compared with an In oxide.

The CAAC-OS is an oxide semiconductor with high crystallinity in which no clear grain boundary is observed. Thus, in the CAAC-OS, a reduction in electron mobility due to the grain boundary is unlikely to occur. Moreover, since the crystallinity of an oxide semiconductor might be decreased by entry of impurities, formation of defects, or the like, the CAAC-OS can be regarded as an oxide semiconductor that has small amounts of impurities and defects (e.g., oxygen vacancies). Hence, an oxide semiconductor including the CAAC-OS is physically stable. Therefore, the oxide semiconductor including the CAAC-OS is resistant to heat and has high reliability. In addition, the CAAC-OS is stable with respect to high temperatures in the manufacturing step (what is called thermal budget). Accordingly, the use of the CAAC-OS for the OS transistor can extend the degree of freedom of the manufacturing step.

[nc-OS]

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. In other words, the nc-OS includes a fine crystal. Note that the size of the fine crystal is, for example, greater than or equal to 1 nm and less than or equal to 10 nm, particularly greater than or equal to 1 nm and less than or equal to 3 nm; thus, the fine crystal is also referred to as a nanocrystal. Furthermore, there is no regularity of crystal orientation between different nanocrystals in the nc-OS. Hence, the orientation in the whole film is not observed. Accordingly, in some cases, the nc-OS cannot be distinguished from an a-like OS or an amorphous oxide semiconductor, depending on the analysis method. For example, when an nc-OS film is subjected to structural analysis by Out-of-plane XRD measurement with an XRD apparatus using $\theta/2\theta$ scanning, a peak indicating crystallinity is not detected. Furthermore, a diffraction pattern like a halo pattern is observed when the nc-OS film is subjected to electron diffraction (also referred to as selected-area electron diffraction) using an electron beam with a probe diameter larger than the diameter of a nanocrystal (e.g., larger than or equal to 50 nm). Meanwhile, in some cases, a plurality of spots in a ring-like region with a direct spot as the center are observed in the obtained electron diffraction pattern when the nc-OS film is subjected to electron diffraction (also referred to as nanobeam electron diffraction) using an electron beam with a probe diameter nearly equal to or smaller than the diameter of a nanocrystal (e.g., larger than or equal to 1 nm and smaller than or equal to 30 nm).

[a-like OS]

The a-like OS is an oxide semiconductor having a structure between those of the nc-OS and the amorphous oxide semiconductor. The a-like OS has a void or a low-density region. That is, the a-like OS has lower crystallinity than the nc-OS and the CAAC-OS. Moreover, the a-like OS has higher hydrogen concentration in the film than the nc-OS and the CAAC-OS.

<<Composition of Oxide Semiconductor>>

Next, the above-described CAC-OS will be described in detail. Note that the CAC-OS relates to the material composition.

[CAC-OS]

The CAC-OS refers to one composition of a material in which elements constituting a metal oxide are unevenly distributed with a size greater than or equal to 0.5 nm and less than or equal to 10 nm, preferably greater than or equal to 1 nm and less than or equal to 3 nm, or a similar size, for example. Note that a state in which one or more metal elements are unevenly distributed and regions including the metal element(s) are mixed with a size greater than or equal to 0.5 nm and less than or equal to 10 nm, preferably greater than or equal to 1 nm and less than or equal to 3 nm, or a similar size in a metal oxide is hereinafter referred to as a mosaic pattern or a patch-like pattern.

In addition, the CAC-OS has a composition in which materials are separated into a first region and a second region to form a mosaic pattern, and the first regions are distributed in the film (this composition is hereinafter also referred to as a cloud-like composition). That is, the CAC-OS is a composite metal oxide having a composition in which the first regions and the second regions are mixed.

Here, the atomic ratios of In, Ga, and Zn to the metal elements contained in the CAC-OS in an In—Ga—Zn oxide are denoted by [In], [Ga], and [Zn], respectively. For example, the first region in the CAC-OS in the In—Ga—Zn oxide is a region having [In] higher than [In] in the composition of the CAC-OS film. Moreover, the second region is a region having [Ga] higher than [Ga] in the composition of the CAC-OS film. Alternatively, for example, the first region is a region having [In] higher than [In] in the second region and [Ga] lower than [Ga] in the second region. Moreover, the second region is a region having [Ga] higher than [Ga] in the first region and [In] lower than [In] in the first region.

Specifically, the first region is a region containing an indium oxide, an indium zinc oxide, or the like as its main component. The second region is a region containing a gallium oxide, a gallium zinc oxide, or the like as its main component. That is, the first region can be rephrased as a region containing In as its main component. The second region can be rephrased as a region containing Ga as its main component.

Note that a clear boundary between the first region and the second region cannot be observed in some cases.

In addition, in a material composition of a CAC-OS in an In—Ga—Zn oxide that contains In, Ga, Zn, and O, there are regions containing Ga as a main component in part of the CAC-OS and regions containing In as a main component in another part of the CAC-OS. These regions each form a mosaic pattern and are randomly present. Thus, it is suggested that the CAC-OS has a structure in which metal elements are unevenly distributed.

The CAC-OS can be formed by a sputtering method under a condition where a substrate is not heated, for example. Furthermore, in the case where the CAC-OS is formed by a sputtering method, any one or more selected from an inert gas (typically, argon), an oxygen gas, and a nitrogen gas is used as a deposition gas. The proportion of the flow rate of an oxygen gas in the total flow rate of the deposition gas during deposition is preferably as low as possible. For example, the proportion of the flow rate of an oxygen gas in the total flow rate of the deposition gas is higher than or equal to 0% and lower than 30%, preferably higher than or equal to 0% and lower than or equal to 10%.

For example, energy dispersive X-ray spectroscopy (EDX) is used to obtain EDX mapping, and according to the EDX mapping, the CAC-OS in the In—Ga—Zn oxide has a structure in which the region containing In as its main component (the first region) and the region containing Ga as its main component (the second region) are unevenly distributed and mixed.

Here, the first region has a higher conductivity than the second region. In other words, when carriers flow through the first region, the conductivity of a metal oxide is exhibited. Accordingly, when the first regions are distributed in a metal oxide like a cloud, high field-effect mobility ($\mu$) can be achieved.

On the other hand, the second region has a higher insulating property than the first region. In other words, when the second regions are distributed in a metal oxide, leakage current can be inhibited.

Thus, in the case where the CAC-OS is used for a transistor, a switching function (On/Off switching function) can be given to the CAC-OS owing to the complementary action of the conductivity derived from the first region and the insulating property derived from the second region. That is, the CAC-OS has a conducting function in part of the material and has an insulating function in another part of the material; as a whole, the CAC-OS has a function of a semiconductor. Separation of the conducting function and the insulating function can maximize each function. Accordingly, when the CAC-OS is used for a transistor, high on-state current (Ion), high field-effect mobility (u), and excellent switching operation can be achieved.

A transistor using the CAC-OS has high reliability. Thus, the CAC-OS is most suitable for a variety of semiconductor devices such as display devices.

An oxide semiconductor has various structures with different properties. Two or more kinds among an amorphous oxide semiconductor, a polycrystalline oxide semiconductor, an a-like OS, a CAC-OS, an nc-OS, and a CAAC-OS may be included in an oxide semiconductor of one embodiment of the present invention.

<Transistor Including Oxide Semiconductor>

Next, the case where the above oxide semiconductor is used for a transistor will be described.

When the above oxide semiconductor is used for a transistor, a transistor with high field-effect mobility can be achieved. In addition, a transistor having high reliability can be achieved.

An oxide semiconductor with a low carrier concentration is preferably used for the transistor. For example, the carrier concentration of an oxide semiconductor is lower than or equal to $1\times10^{17}$ cm$^{-3}$, preferably lower than or equal to $1\times10^{15}$ cm$^{-3}$, further preferably lower than or equal to $1\times10^{13}$ cm$^{-3}$, still further preferably lower than or equal to $1\times10^{11}$ cm$^{-3}$, yet further preferably lower than $1\times10^{10}$ cm$^{-3}$, and higher than or equal to $1\times10^{-9}$ cm$^{-3}$. In order to reduce the carrier concentration of an oxide semiconductor film, the impurity concentration in the oxide semiconductor film is reduced so that the density of defect states can be reduced. In this specification and the like, a state with a low impurity concentration and a low density of defect states is referred to as a highly purified intrinsic or substantially highly purified intrinsic state. Note that an oxide semiconductor having a low carrier concentration may be referred to as a highly purified intrinsic or substantially highly purified intrinsic oxide semiconductor.

A highly purified intrinsic or substantially highly purified intrinsic oxide semiconductor film has a low density of defect states and accordingly has a low density of trap states in some cases.

Charge trapped by the trap states in the oxide semiconductor takes a long time to disappear and might behave like fixed charge. Thus, a transistor whose channel formation region is formed in an oxide semiconductor with a high density of trap states has unstable electrical characteristics in some cases.

Accordingly, in order to obtain stable electrical characteristics of a transistor, reducing the impurity concentration in an oxide semiconductor is effective. In order to reduce the impurity concentration in the oxide semiconductor, it is preferable that the impurity concentration in an adjacent film be also reduced. Examples of impurities include hydrogen, nitrogen, an alkali metal, an alkaline earth metal, iron, nickel, and silicon. Note that impurities in an oxide semiconductor refer to, for example, elements other than the main components of an oxide semiconductor. For example, an element with a concentration lower than 0.1 atomic % can be regarded as an impurity.

<Impurity>

Here, the influence of each impurity in the oxide semiconductor will be described.

When silicon or carbon, which is one of Group 14 elements, is contained in the oxide semiconductor, defect states are formed in the oxide semiconductor. Thus, the concentration of silicon or carbon (the concentration obtained by secondary ion mass spectrometry (SIMS)) in the semiconductor layer is set to $2\times10^{18}$ atoms/cm$^3$ or lower, preferably $2\times10^{17}$ atoms/cm$^3$ or lower.

When the oxide semiconductor contains an alkali metal or an alkaline earth metal, defect states are formed and carriers are generated in some cases. Accordingly, a transistor using an oxide semiconductor that contains an alkali metal or an alkaline earth metal tends to have normally-on characteristics. Thus, the concentration of an alkali metal or an alkaline earth metal in the oxide semiconductor, which is obtained by SIMS, is lower than or equal to $1\times10^{18}$ atoms/cm$^3$, preferably lower than or equal to $2\times10^{16}$ atoms/cm$^3$.

When the oxide semiconductor contains nitrogen, the oxide semiconductor easily becomes n-type by generation of electrons serving as carriers and an increase in carrier concentration. As a result, a transistor using an oxide semiconductor containing nitrogen as a semiconductor is likely to have normally-on characteristics. When nitrogen is contained in the oxide semiconductor, a trap state is sometimes formed. This might make the electrical characteristics of the transistor unstable. Therefore, the concentration of nitrogen in the oxide semiconductor, which is obtained by SIMS, is lower than $5\times10^{19}$ atoms/cm$^3$, preferably lower than or equal to $5\times10^{18}$ atoms/cm$^3$, further preferably lower than or equal to $1\times10^{18}$ atoms/cm$^3$, still further preferably lower than or equal to $5\times10^{17}$ atoms/cm$^3$.

Hydrogen contained in the oxide semiconductor reacts with oxygen bonded to a metal atom to be water, and thus forms an oxygen vacancy in some cases. Entry of hydrogen into the oxygen vacancy generates an electron serving as a carrier in some cases. Furthermore, bonding of part of hydrogen to oxygen bonded to a metal atom causes generation of an electron serving as a carrier in some cases. Thus, a transistor using an oxide semiconductor containing hydrogen is likely to have normally-on characteristics. Accordingly, hydrogen in the oxide semiconductor is preferably reduced as much as possible. Specifically, the hydrogen concentration in the oxide semiconductor, which is obtained by SIMS, is set lower than $1\times10$ 20 atoms/cm$^3$, preferably lower than $1\times10^{19}$ atoms/cm$^3$, further preferably lower than $5\times10^{18}$ atoms/cm$^3$, still further preferably lower than $1\times10^{18}$ atoms/cm$^3$.

When an oxide semiconductor with sufficiently reduced impurities is used for the channel formation region of the transistor, stable electrical characteristics can be given.

At least part of this embodiment can be implemented in combination with the other embodiments described in this specification as appropriate.

Embodiment 6

In this embodiment, electronic devices and display systems of one embodiment of the present invention will be described with reference to FIG. 32 to FIG. 36.

Examples of the electronic device of one embodiment of the present invention include electronic devices including a camera, a processing portion, and an output portion.

Examples of the electronic device of one embodiment of the present invention include a portable data terminal, a portable information terminals such as a smartphone and a tablet terminal, information terminals (wearable devices) such as watch-type and bracelet-type information terminals, in addition to electronic device with a relatively large screen, such as a television device, a desktop or laptop information terminal.

Examples of an electronic device of one embodiment of the present invention will be described. FIG. 32A to FIG. 32E illustrate electronic devices each of which includes an electronic component 4700 including the processing portion described in the above embodiment.

Figure 32A:
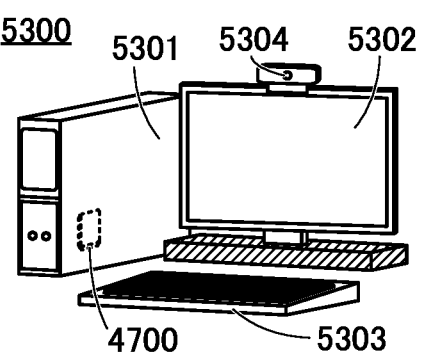
FIG. 32A to FIG. 32E are diagrams each illustrating an example of an electronic device.

FIG. 32A illustrates a desktop information terminal 5300. The desktop information terminal 5300 includes a main body 5301 of the information terminal, a display portion 5302, and a keyboard 5303. A camera 5304 is fixed to a housing provided with the display portion 5302.

With use of the camera 5304, the display portion 5302, and the electronic component 4700, the desktop information terminal 5300 can estimate a situation of a user of the desktop information terminal 5300 and display information on the estimated user's situation on the display portion 5302. Alternatively, information on a situation of a user of an electronic device connected to the desktop information terminal 5300 through a network can be displayed on the display portion 5302.

The desktop information terminal 5300 illustrated in FIG. 32A has a structure where the camera 5304 is attached externally; however, the structure is not limited thereto. The camera 5304 may be incorporated in the housing provided with the display portion 5302.

Figure 32B:
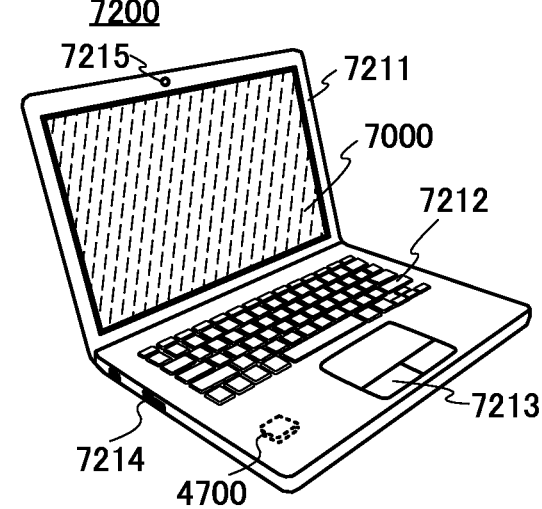

FIG. 32B illustrates an example of a notebook information terminal. A notebook information terminal 7200 includes a housing 7211, a keyboard 7212, a pointing device 7213, an external connection port 7214, a camera 7215, and the like. In the housing 7211, the display portion 7000 is incorporated.

With use of the camera 7215, the display portion 7000, and the electronic component 4700, the notebook information terminal 7200 can estimate a situation of a user of the notebook information terminal 7200 and display information on the estimated user's situation on the display portion 7000. Alternatively, information on a situation of a user of an electronic device connected to the notebook information terminal 7200 through a network can be displayed on the display portion 7000.

Figure 32C:
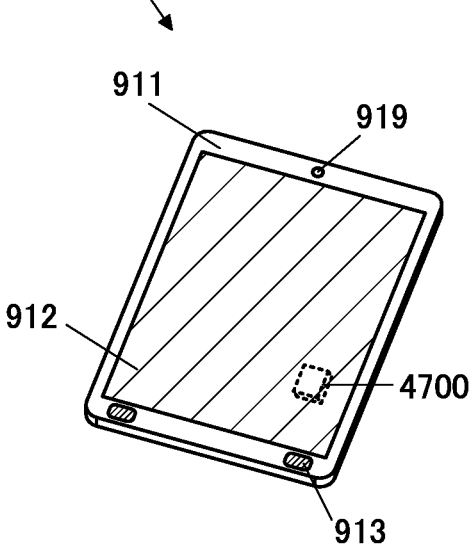

FIG. 32C illustrates an example of a portable data terminal. A portable data terminal 900 includes a housing 911, a display portion 912, a speaker 913, a camera 919, and the like.

With use of the camera 919, the display portion 912, and the electronic component 4700, the portable data terminal 900 can estimate a situation of a user of the portable data terminal 900, and display information on the estimated user's situation on the display portion 912. Alternatively, information on a situation of a user of an electronic device connected to the portable data terminal 900 through a network can be displayed on the display portion 912.

Figure 32D:
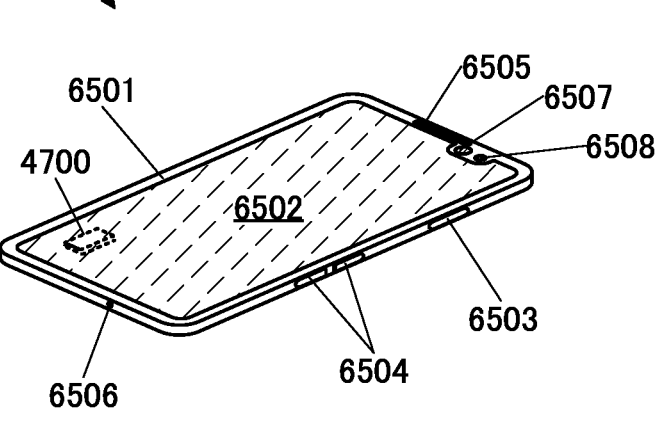

FIG. 32D illustrates an example of a portable information terminal. A portable information terminal 6500 can be used as a smartphone.

The portable information terminal 6500 includes a housing 6501, a display portion 6502, a power button 6503, buttons 6504, a speaker 6505, a microphone 6506, a camera 6507, a light source 6508, and the like. The display portion 6502 has a touch panel function.

With use of the camera 6507, the display portion 6502, and the electronic component 4700, the portable information terminal 6500 can estimate a situation of a user of the portable information terminal 6500, and display information on the estimated user's situation on the display portion 6502. Alternatively, information on a situation of a user of an electronic device connected to the portable information terminal 6500 through a network can be displayed on the display portion 6502.

Figure 32E:
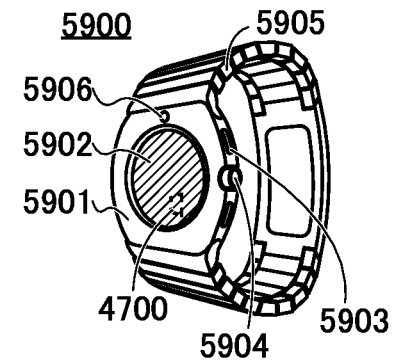

FIG. 32E illustrates an information terminal 5900 as an example of a wearable terminal. The information terminal 5900 includes a housing 5901, a display portion 5902, an operation switch 5903, an operation switch 5904, a band 5905, a camera 5906, and the like With use of the camera 5906, the display portion 5902, and the electronic component 4700, the information terminal 5900 can estimate a situation of a user of the information terminal 5900, and display information on the estimated user's situation on the display portion 5902. Alternatively, information on a situation of a user of an electronic device connected to the information terminal 5900 through a network can be displayed on the display portion 5902.

Note that headphones including a sensor portion may be connected to the electronic devices such as the desktop information terminal 5300 as illustrated in FIG. 32A, the notebook information terminal 7200 as illustrated in FIG. 32B, the portable data terminal 900 as illustrated in FIG. 32C, and the portable information terminal 6500 as illustrated in FIG. 32D. With use of the sensor portion, the situation of the user of the electronic device can be estimated.

An electronic device of one embodiment of the present invention is acceptable as long as it includes a camera, a processing portion, and a display portion; thus, examples of one embodiment of the present invention include an electronic device for virtual reality or augmented reality and an electronic device for substitutional reality (SR) or mixed reality (MR). Examples of the electronic device of one embodiment of the present invention include information terminals (wearable devices) that can be worn on the head such as a head-mounted display, a glasses-type terminal, and a goggle-type terminal.

Figure 33A:
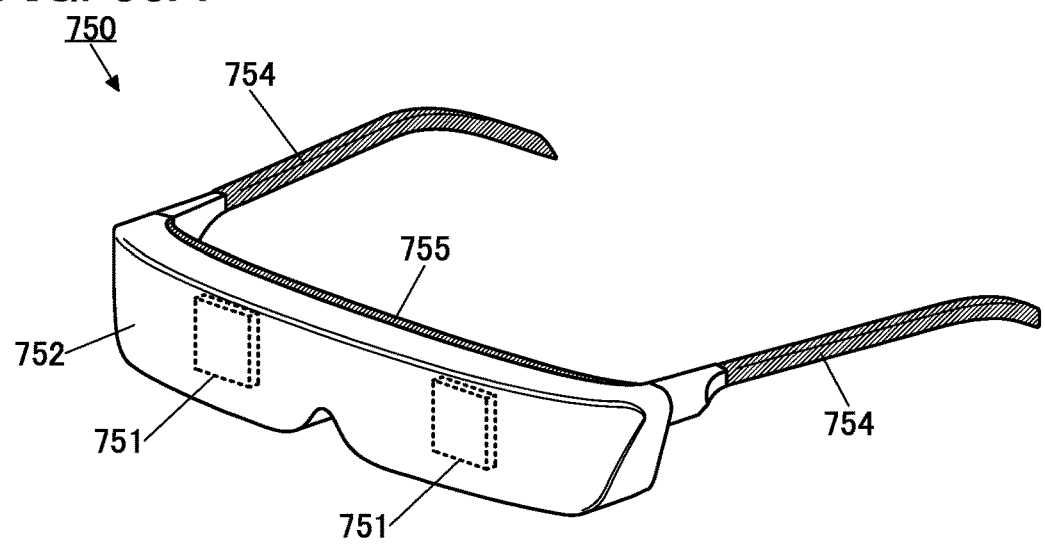
FIG. 33A to FIG. 33C are diagrams illustrating examples of electronic devices.
Figure 33B:
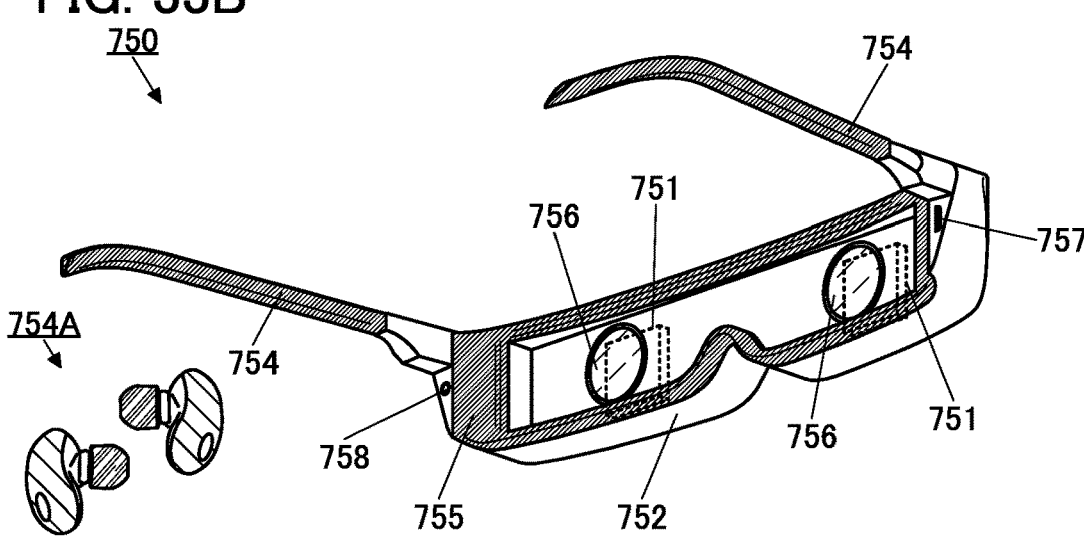
Figure 33C:
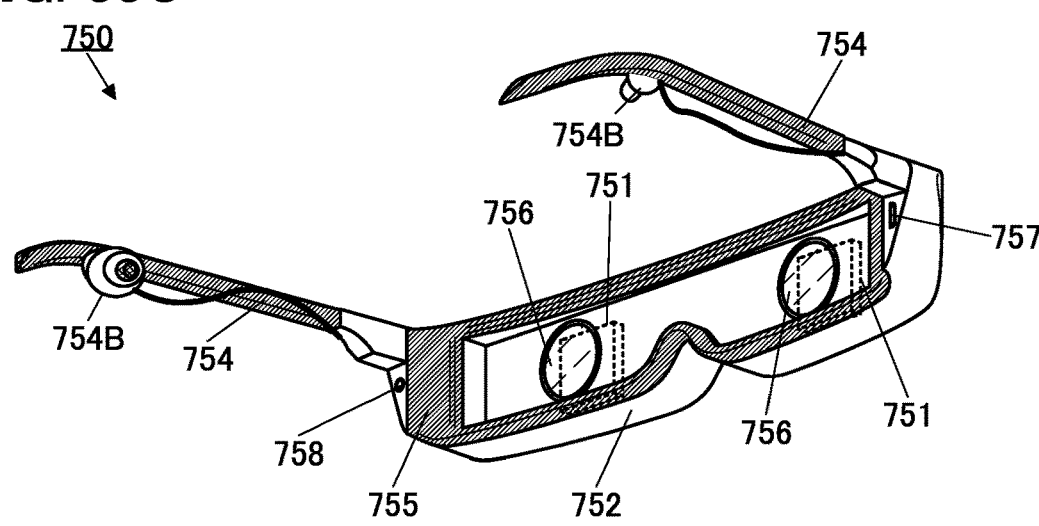

FIG. 33A to FIG. 33C are perspective views of an electronic device 750. FIG. 33A is a perspective view illustrating the front surface, the top surface, and the left side surface of the electronic device 750, and FIG. 33B and FIG. 33C are each a perspective view illustrating the back surface, the bottom surface, and the right side surface of the electronic device 750.

The electronic device 750 includes a pair of display devices 751, a housing 752, a pair of mounting portions 754, a cushion 755, a pair of lenses 756, and the like. The pair of display devices 751 is positioned to be seen through the lenses 756 inside the housing 752.

The pair of display devices 751 correspond to the display portion 52 illustrated in FIG. 5B. The pair of lenses 756 correspond to the optical system 67 in FIG. 5B. Although not illustrated, the electronic device 750 in FIG. 33A to FIG. 33C includes a camera and an electronic component including the processing portion described in the above embodiment. The camera can capture an image of the user's eye and his/her periphery. Although not illustrated, the electronic device 750 illustrated in FIG. 33A to FIG. 33C is provided with the motion detection portion 68, the audio 63, the control portion 64, the communication portion 65, and the battery 66, which are described in Embodiment 1, in the housing 752.

The electronic device 750 is an electronic device for VR. A user wearing the electronic device 750 can see an image displayed on the display device 751 through the lens 756. Furthermore, the pair of display devices 751 may display different images, whereby three-dimensional display using parallax can be performed.

An input terminal 757 and an output terminal 758 are provided on the back side of the housing 752. To the input terminal 757, a cable for supplying a video signal from a video output device or the like, power for charging a battery provided in the housing 752, or the like can be connected. The output terminal 758 can function as, for example, an audio output terminal to which earphones, headphones, or the like can be connected.

The housing 752 preferably includes a mechanism by which the left and right positions of the lens 756 and the display device 751 can be adjusted to the optimal positions in accordance with the position of the user's eye. In addition, the housing 752 preferably includes a mechanism for adjusting focus by changing the distance between the lens 756 and the display device 751.

With use of the camera, the display device 751, and the above electronic component, the electronic device 750 can estimate a situation of a user of the electronic device 750 and can display information on the estimated user's situation on the display device 751. Alternatively, information on a situation of a user of an electronic device connected to the electronic device 750 through a network can be displayed on the display device 751.

The cushion 755 is a portion in contact with the user's face (forehead, cheek, or the like). The cushion 755 is in close contact with the user's face, so that light leakage can be prevented, which increases the sense of immersion. A soft material is preferably used for the cushion 755 so that the cushion 755 is in close contact with the face of the user wearing the electronic device 750. For example, a material such as rubber, silicone rubber, urethane, or sponge can be used. Furthermore, when a sponge or the like whose surface is covered with cloth, leather (natural leather or synthetic leather), or the like is used, a gap is unlikely to be generated between the user's face and the cushion 755, whereby light leakage can be suitably prevented. Furthermore, using such a material is preferable because it has a soft texture and a user does not feel cold when wearing the device in a cold season, for example. The member in contact with user's skin, such as the cushion 755 or the mounting portion 754, is preferably detachable because cleaning or replacement can be easily performed.

The electronic device in this embodiment may further include earphones 754A. The earphones 754A include a communication portion (not illustrated) and have a wireless communication function. The earphones 754A can output audio data with the wireless communication function. The earphones 754A may include a vibration mechanism to function as bone-conduction earphones.

Like earphones 754B illustrated in FIG. 33C, the earphones 754A can be connected to the mounting portion 754 directly or by wiring. The earphones 754B and the mounting portion 754 may each have a magnet. This is preferable because the earphones 754B can be fixed to the mounting portion 754 with magnetic force and thus can be easily housed.

The earphones 754A may include a sensor portion. With use of the sensor portion, the situation of the user of the electronic device can be estimated.

FIGS. 34A to 34C are external views of an electronic device 8300. The electronic device 8300 includes a housing

8301, a display portion 8302, a band-shaped fixing unit 8304, and a pair of lenses 8305. Although not illustrated, the electronic device 8300 in FIG. 34A to FIG. 34C includes a camera and an electronic component including the processing portion described in the above embodiment. The camera can capture an image of the user's eye and his/her periphery.

A user can see display on the display portion 8302 through the lenses 8305. The display portion 8302 is preferably curved so that the user can feel high realistic sensation. Another image displayed on another region of the display portion 8302 is viewed through the lenses 8305, so that three-dimensional display using parallax or the like can be performed. Note that the structure is not limited to the structure in which one display portion 8302 is provided; two display portions 8302 may be provided and one display portion may be provided per eye of the user.

With use of the camera, the display portion 8302, and the above electronic component, the electronic device 8300 can estimate a situation of a user of the electronic device 8300 and can display information on the estimated user's situation on the display portion 8302. Alternatively, information on a user of an electronic device connected to the electronic device 8300 through a network can be displayed on the display portion 8302.

FIG. 34D is an external view of an electronic device 8400. The electronic device 8400 includes a pair of housings 8401, a mounting portion 8402, and a cushion 8403. A display portion 8404 and a lens 8405 are provided in each of the pair of housings 8401. When the pair of display portions 8404 display different images, three-dimensional display using parallax can be performed. Although not illustrated, the electronic device 8400 in FIG. 34D includes a camera and an electronic component including the processing portion described in the above embodiment. The camera can capture an image of the user's eye and his/her periphery.

A user can see display on the display portion 8404 through the lens 8405. The lens 8405 has a focus adjustment mechanism and can adjust the position according to the user's eyesight. The display portion 8404 is preferably a square or a horizontal rectangle. This can improve a realistic sensation.

With use of the camera, the display portion 8404, and the above electronic component, the electronic device 8400 can estimate a situation of a user of the electronic device 8400 and can display information on the estimated user's situation on the display portion 8404. Alternatively, information on a situation of a user of an electronic device connected to the electronic device 8400 through a network can be displayed on the display portion 8404.

The mounting portion 8402 preferably has flexibility and elasticity so as to be adjusted to fit the size of the user's face and not to slide down. In addition, part of the mounting portion 8402 preferably has a vibration mechanism functioning as a bone conduction earphone. Thus, audio devices such as an earphone and a speaker are not necessarily provided separately, and the user can enjoy videos and sounds only when wearing the electronic device 8400. Note that the housing 8401 may have a function of outputting sound data by wireless communication.

The description of the cushion 755 illustrated in FIG. 33A to FIG. 33C can be referred to for the mounting portion 8402 and the cushion 8403.

FIG. 34E is an external view of an electronic device 8200. The electronic device 8200 includes a mounting portion 8201, a lens 8202, a main body 8203, a display portion 8204, a cable 8205, and the like. A battery 8206 is incorporated in the mounting portion 8201. Although not illustrated, the electronic device 8200 in FIG. 34E includes a camera and an electronic component including the processing portion described in the above embodiment. The camera can capture an image of the user's eye and his/her periphery.

The cable 8205 supplies power from the battery 8206 to the main body 8203. The main body 8203 includes a wireless receiver or the like to receive video information and display it on the display portion 8204. The main body 8203 includes a camera, and information on the movement of the eyeballs or the eyelids of the user can be used as an input means.

The mounting portion 8201 may include a plurality of electrodes capable of sensing a current flowing accompanying with the movement of the user's eyeball at a position in contact with the user to recognize the user's sight line. The mounting portion 8201 may also have a function of monitoring the user's pulse with use of current flowing through the electrodes. The mounting portion 8201 may include a variety of sensors such as a temperature sensor, a pressure sensor, and an acceleration sensor to have a function of displaying the user's biological information on the display portion 8204, a function of changing a video displayed on the display portion 8204 in accordance with the movement of the user's head, and the like.

With use of the camera, the display portion 8204, and the above electronic component, the electronic device 8200 can estimate a situation of a user of the electronic device 8200 and can display information on the estimated user's situation on the display portion 8204. Alternatively, information on a situation of a user of an electronic device connected to the electronic device 8200 through a network can be displayed on the display portion 8204.

Figure 35A:
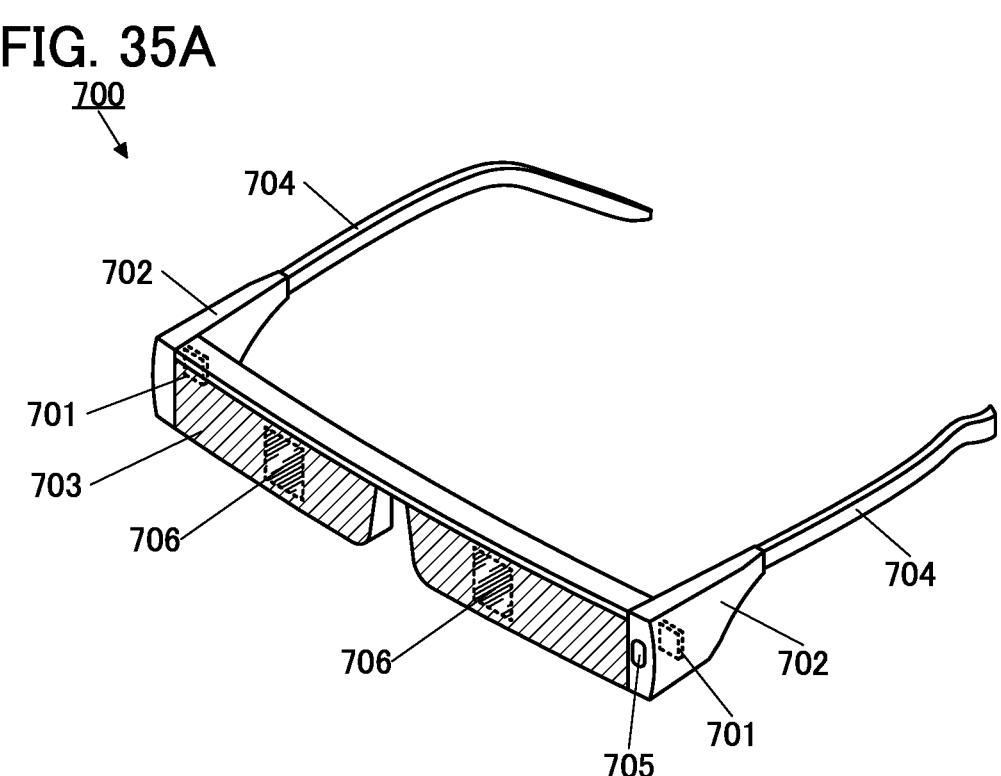
FIG. 35A and FIG. 35B are diagrams illustrating examples of electronic devices.

FIG. 35A is a perspective view of an electronic device 700. The electronic device 700 includes a pair of display devices 701, a pair of housings 702, a pair of optical members 703, a pair of mounting portions 704, and the like. Although not illustrated, the electronic device 700 in FIG. 35A includes a camera and an electronic component including the processing portion described in the above embodiment. The camera can capture an image of the user's eye and his/her periphery.

The electronic device 700 can project an image displayed on the display device 701 onto a display region 706 of the optical member 703. Since the optical members 703 have a light-transmitting property, a user can see images displayed on the display regions 706, which are superimposed on transmission images seen through the optical members 703. Thus, the electronic device 700 is an electronic device capable of AR display.

One housing 702 is provided with a camera 705 capable of taking an image of what lies in front thereof. Although not illustrated, one of the housings 702 is provided with a wireless receiver or a connector to which a cable can be connected, whereby a video signal or the like can be supplied to the housing 702. Furthermore, when the housing 702 is provided with an acceleration sensor such as a gyroscope sensor, the orientation of the user's head can be detected and an image corresponding to the orientation can be displayed on the display region 706. Moreover, the housing 702 is preferably provided with a battery, and charging can be performed with or without a wire.

Next, a method for projecting an image on the display region 706 of the electronic device 700 is described with reference to FIG. 35B. The display device 701, a lens 711, and a reflective plate 712 are provided in the housing 702. In addition, a reflective surface 713 functioning as a half mirror is provided in a portion corresponding to the display region 706 of the optical member 703.

Light 715 emitted from the display device 701 passes through the lens 711 and is reflected by the reflective plate 712 toward the optical member 703. In the optical member 703, the light 715 is fully reflected repeatedly by end surfaces of the optical member 703 and reaches the reflective surface 713, whereby an image is projected on the reflective surface 713. Accordingly, the user can see both the light 715 reflected by the reflective surface 713 and transmitted light 716 that passes through the optical member 703 (including the reflective surface 713).

Figure 35B:
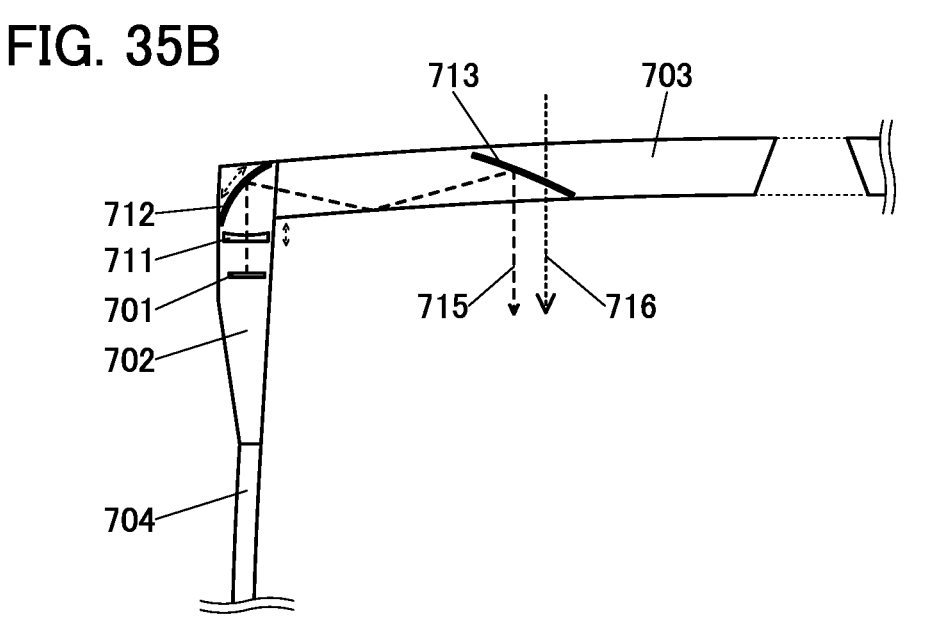

FIG. 35B illustrates an example in which the reflective plate 712 and the reflective surface 713 each have a curved surface. This structure can increase optical design flexibility and reduce the thickness of the optical member 703, compared to the case where the reflective plate 712 and the reflective surface 713 are flat. Note that the reflective plate 712 and the reflective surface 713 may be flat.

The reflective plate 712 can use a component having a mirror surface and preferably has high reflectance. As the reflective surface 713, a half mirror utilizing reflection of a metal film may be used, but the use of a total-reflection prism or the like can increase the transmittance of the transmitted light 716.

Here, the housing 702 preferably includes a mechanism for adjusting the distance or angle between the lens 711 and the display device 701. This enables focus adjustment and zooming in/out of images, for example. One or both of the lens 711 and the display device 701 are configured to be movable in the optical-axis direction, for example.

The housing 702 preferably includes a mechanism capable of adjusting the angle of the reflective plate 712. The position of the display region 706 where images are displayed can be changed by changing the angle of the reflective plate 712. Thus, the display region 706 can be placed at the optimum position in accordance with the position of the user's eye.

With use of the camera, the display device 701, and the above electronic component, the electronic device 700 can estimate a situation of a user of the electronic device 700 and can display information on the estimated user's situation on the display device 701. Alternatively, information on a situation of a user of an electronic device connected to the electronic device 700 through a network can be displayed on the display device 701.

An electronic device of one embodiment of the present invention is acceptable as long as it includes a camera, a processing portion, and a display portion; thus, one embodiment of the present invention may be ab electronic device with a display function as well as the above-described electronic device. Examples of such an electronic device include a portable game machine, a digital camera, a digital video camera, a digital photo frame, a mobile phone, a portable game machine, and an audio reproducing device, in addition to electronic devices with a relatively large screen, such as a television device, a monitor device, digital signage, a pachinko machine, and a game machine.

Specifically, an electronic device such as a portable game machine or a smartphone can be sometimes used as, for example, a VR device when a housing to which the electronic device is attached is worn on the head with the use of a band-like fixing portion, a mounting portion, or the like. Therefore, a display portion of the electronic device may include the display device of one embodiment of the present invention.

The electronic device in this embodiment may include an antenna. With the antenna receiving a signal, a video, information, and the like can be displayed on a display portion. When the electronic device includes an antenna and a secondary battery, the antenna may be used for contactless power transmission.

The electronic device in this embodiment may include a sensor (a sensor having a function of sensing, detecting, or measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device in this embodiment can have a variety of functions. For example, the electronic device can have a function of displaying a variety of information (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

The display system of one embodiment of the present invention may include two or more electronic device described above. In this case, some of the two or more electronic devices use a camera and an electronic component including the processing portion described in the above embodiment, whereby a situation of a user of the electronic device can be estimated, and information on the estimated user's situation can be displayed on a display portion in the electronic device or a display device. The other of the two or more electronic devices can display information on a situation of a user of an electronic device different from the above electronic device connected through a network, on a display portion in the electronic device or a display device.

Alternatively, the display system of one embodiment of the present invention may include two or more electronic devices described above and one or more computers described below.

[Computer]

Figures 36A, 36B, 36C:
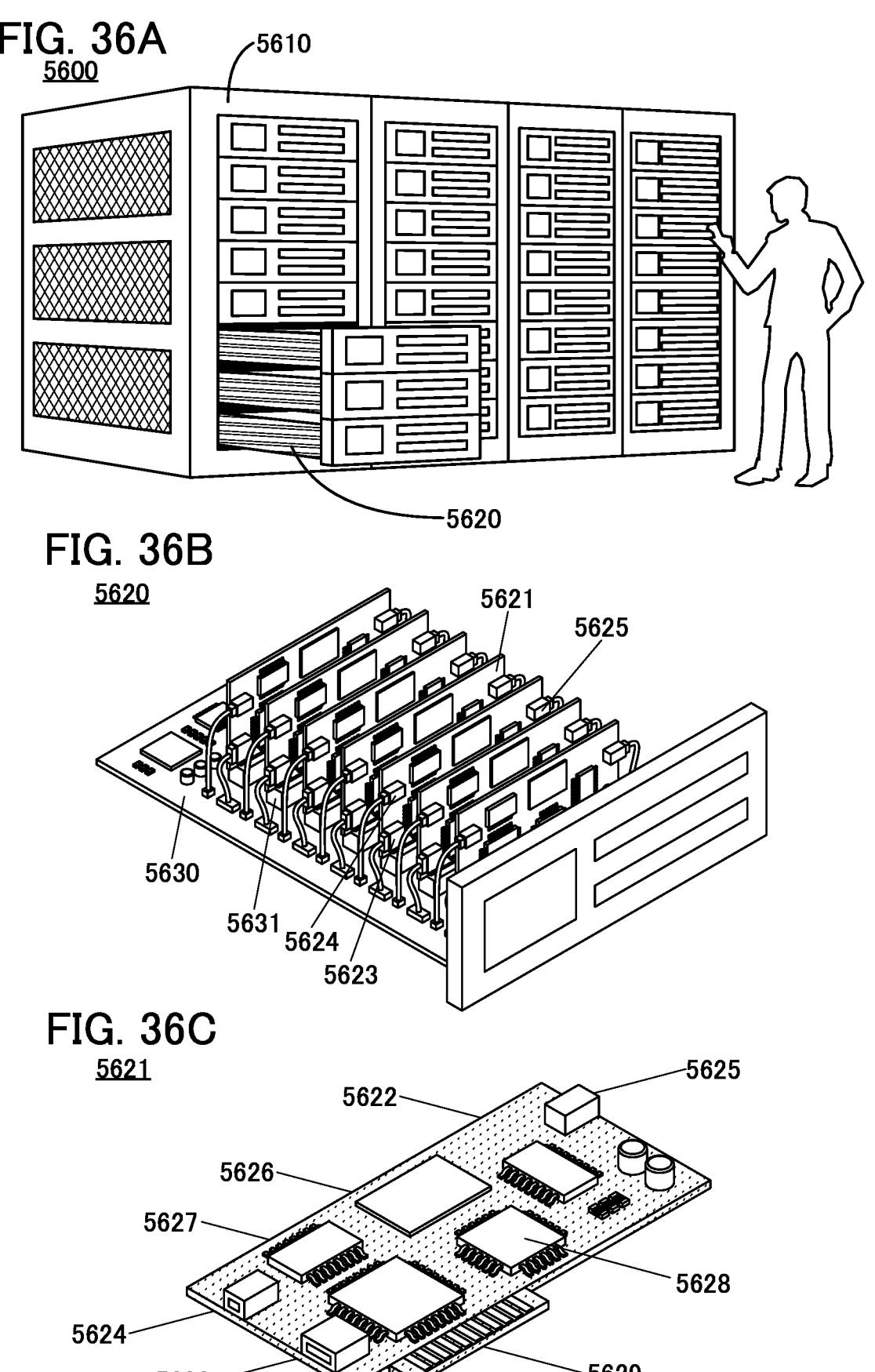
FIG. 36A to FIG. 36C are diagrams illustrating examples of an electronic device.

A computer 5600 illustrated in FIG. 36A is an example of a large computer. In the computer 5600, a plurality of rack mount computers 5620 are stored in a rack 5610.

The computer 5620 can have a structure in a perspective view illustrated in FIG. 36B, for example. In FIG. 36B, the computer 5620 includes a motherboard 5630, and the motherboard 5630 includes a plurality of slots 5631 and a plurality of connection terminals. A PC card 5621 is inserted in the slot 5631. In addition, the PC card 5621 includes a connection terminal 5623, a connection terminal 5624, and a connection terminal 5625, each of which is connected to the motherboard 5630.

The PC card 5621 illustrated in FIG. 36C is an example of a processing board provided with a CPU, a GPU, a semiconductor device, or the like. The PC card 5621 includes a board 5622. The board 5622 includes a connection terminal 5623, a connection terminal 5624, a connection terminal 5625, a semiconductor device 5626, a semiconductor device 5627, a semiconductor device 5628, and a connection terminal 5629. Note that FIG. 36C also illustrates semiconductor devices other than the semiconductor device 5626, the semiconductor device 5627, and the semiconductor device 5628; the following description of the semiconductor device 5626, the semiconductor device 5627, and the semiconductor device 5628 is referred to for these semiconductor devices.

The connection terminal 5629 has a shape with which the connection terminal 5629 can be inserted in the slot 5631 of the motherboard 5630, and the connection terminal 5629 functions as an interface for connecting the PC card 5621 and the motherboard 5630. An example of the standard for the connection terminal 5629 is PCIe.

The connection terminal 5623, the connection terminal 5624, and the connection terminal 5625 can serve as, for example, an interface for performing power supply, or signal input to the PC card 5621. As another example, the connection terminal 5623, the connection terminal 5624, and the connection terminal 5625 can serve as an interface for outputting a signal calculated by the PC card 5621. Examples of the standard for each of the connection terminal 5623, the connection terminal 5624, and the connection terminal 5625 include USB (Universal Serial Bus), SATA (Serial ATA), and SCSI (Small Computer System Interface). In the case where video signals are output from the connection terminal 5623, the connection terminal 5624, and the connection terminal 5625, an example of the standard therefor is HDMI (registered trademark).

The semiconductor device 5626 includes a terminal (not illustrated) for inputting and outputting signals, and when the terminal is inserted in a socket (not illustrated) of the board 5622, the semiconductor device 5626 and the board 5622 can be electrically connected to each other.

The semiconductor device 5627 includes a plurality of terminals, and when the terminals are reflow-soldered, for example, to wirings of the board 5622, the semiconductor device 5627 and the board 5622 can be electrically connected to each other. Examples of the semiconductor device 5627 include an FPGA (Field Programmable Gate Array), a GPU, a CPU, and the like.

The semiconductor device 5628 includes a plurality of terminals, and when the terminals are reflow-soldered, for example, to wirings of the board 5622, the semiconductor device 5628 and the board 5622 can be electrically connected to each other. An example of the semiconductor device 5628 is a semiconductor device.

As the semiconductor device 5627 and/or the semiconductor device 5628, for example, an electronic component including the processing portion described in the above embodiment can be used. With use of the semiconductor device 5627 and/or the semiconductor device 5628, situations of users of a plurality of electronic devices included in the display system are each estimated, whereby power consumption of each of the plurality of electronic devices in the display system can be reduced. Furthermore, delay of the operation speed of each of the plurality of electronic devices in the display system can be inhibited.

The computer 5600 can also function as a parallel computer. When the computer 5600 is used as a parallel computer, large-scale computation necessary for artificial intelligence learning and inference can be performed, for example.

At least part of the structure examples, the drawings corresponding thereto, and the like described in this embodiment as examples can be combined with the other structure examples, the other drawings, and the like as appropriate.

At least part of this embodiment can be implemented in combination with the other embodiments described in this specification as appropriate.

REFERENCE NUMERALS

ACTF: circuit, AFP: circuit, ALP: array portion, ANN: neural network, BW: bus wiring, CA: cell array, C1:

capacitor, C1r: capacitor, C5: capacitor, CSm: capacitor, F1: transistor, F1m: transistor, F2: transistor, F2m: transistor, F3: transistor, F4: transistor, HC: holding portion, ILD: circuit, IM: cell, IMref: cell, ITRZ: converter circuit, MAC1: arithmetic circuit, MC: circuit, MCr: circuit, MP: circuit, M1: transistor, M1r: transistor, M2: transistor, M3: transistor, M3r: transistor, NN: node, NNref: node, n1: node, OL: wiring, OLB: wiring, PS: subpixel, SWL1: wiring, SWL2: wiring, SWS1: circuit, SWS2: circuit, TW: circuit, VE: wiring, VEr: wiring, WCL: wiring, WCS: circuit, WL: wiring, WLD: circuit, WSD: circuit, WSL: wiring, WX1L: wiring, XCL: wiring, XCS: circuit, XLD: circuit, 10: electronic device, 11: student, 12: camera, 20: electronic device, 21: teacher, 22: camera, 30: network, 50: electronic device, 51: camera, 52: display portion, 52L: display portion, 52R: display portion, 53: processing portion, 53a: processing portion, 53b: processing portion, 53c: processing portion, 53d: processing portion, 54: processing portion, 54a: processing portion, 54b: processing portion, 55: sensor portion, 62: frame memory, 63: audio, 64: control portion, 65: communication portion, 66: battery, 67: optical system, 67L: optical system, 67R: optical system, 68: detection portion, 70: display system, 71: electronic device, 72: electronic device, 73: network, 74: server, 75: camera, 76: processing portion, 77: processing portion, 78: processing portion, 91: input data, 92: neural network, 93: output data, 94: neural network, 95: intermediate data, 96: input data, 97: neural network, 100: display device, 100A: display device, 100B: display device, 100C: display device, 100D: display device, 100E: display device, 100F: display device, 100G: display device, 101: layer, 110: pixel, 110a: subpixel, 110b: subpixel, 110c: subpixel, 110d: subpixel, 111a: pixel electrode, 111b: pixel electrode, 111c: pixel electrode, 113a: layer, 113b: layer, 113c: layer, 114: layer, 115: common electrode, 117: light-blocking layer, 118: sacrificial layer, 119: sacrificial layer, 120: substrate, 122: resin layer, 124a: pixel, 124b: pixel, 125: insulating layer, 126a: conductive layer, 126b: conductive layer, 126c: conductive layer, 127: insulating layer, 128: layer, 129a: coloring layer, 129b: coloring layer, 129c: coloring layer, 130a: light-emitting device, 130b: light-emitting device, 130c: light-emitting device, 131: protective layer, 132: protective layer, 138: region, 139: region, 142: adhesive layer, 151: substrate, 152: substrate, 153: insulating layer, 162: display portion, 164: circuit, 165: wiring, 166: conductive layer, 172: FPC, 173: IC, 201: transistor, 204: connection portion, 205: transistor, 209: transistor, 210: transistor, 211: insulating layer, 213: insulating layer, 214: insulating layer, 215: insulating layer, 218: insulating layer, 221: conductive layer, 222a: conductive layer, 222b: conductive layer, 223: conductive layer, 225: insulating layer, 228: region, 231: semiconductor layer, 231i: channel formation region, 231n: low-resistance region, 240: capacitor, 241: conductive layer, 242: connection layer, 243: insulating layer, 245: conductive layer, 251: conductive layer, 252: conductive layer, 254: insulating layer, 255a: insulating layer, 255b: insulating layer, 256: plug, 261: insulating layer, 262: insulating layer, 263: insulating layer, 264: insulating layer, 265: insulating layer, 271: plug, 274: plug, 274a: conductive layer, 274b: conductive layer, 280: display module, 281: display portion, 282: circuit portion, 283: pixel circuit portion, 283a: pixel circuit, 284: pixel portion, 284a:

pixel, 285: terminal portion, 286: wiring portion, 290: FPC, 291: substrate, 292: substrate, 301: substrate, 301A: substrate, 301B: substrate, 310: transistor, 310A: transistor, 310B: transistor, 311: conductive layer, 312: low-resistance region, 313: insulating layer, 314: insulating layer, 315: element isolation layer, 320: transistor, 321: semiconductor layer, 323: insulating layer, 324: conductive layer, 325: conductive layer, 326: insulating layer, 327: conductive layer, 328: insulating layer, 329: insulating layer, 331: substrate, 332: insulating layer, 335: insulating layer, 336: insulating layer, 341: conductive layer, 342: conductive layer, 343: plug, 344: insulating layer, 345: insulating layer, 346: insulating layer, 347: bump, 348: adhesive layer, 350: arithmetic circuit, 351: substrate, 353: layer, 355: functional layer, 357: layer, 359: substrate, 700: electronic device, 701: display device, 702: housing, 703: optical member, 704: mounting portion, 705: camera, 706: display region, 711: lens, 712: reflective plate, 713: reflective surface, 715: light, 716: transmitted light, 750: electronic device, 751: display device, 752: housing, 754: mounting portion, 754A: earphone, 754B: earphone, 755: cushion, 756: lens, 757: input terminal, 758: output terminal, 900: portable data terminal, 911: housing, 912: display portion, 913: speaker, 919: camera, 960: eyebrow, 961: eyelash, 962: pupil, 963: cornea, 965: sclera, 966: upper eyelid, 967: lower eyelid, 1000_1: display portion, 1000_3: display portion, 1010_1: image, 1010_2: image, 1010_3: image, 1010_4: image, 1010_5: image, 1010_8: image, 1020_1: user, 1020_2: user, 1020_3: user, 1020_4: user, 1020_5: user, 1020_8: user, 1030_3: image, 1030_4: image, 1030_5: image, 1031: image, 4700: electronic component, 5300: desktop information terminal, 5301: main body, 5302: display portion, 5303: keyboard, 5304: camera, 5600: computer, 5610: rack, 5620: computer, 5621: PC card, 5622: board, 5623: connection terminal, 5624: connection terminal, 5625: connection terminal, 5626: semiconductor device, 5627: semiconductor device, 5628: semiconductor device, 5629: connection terminal, 5630: motherboard, 5631: slot, 5900: information terminal, 5901: housing, 5902: display portion, 5903: operation switch, 5904: operation switch, 5905: band, 5906: camera, 6500: portable information terminal, 6501: housing, 6502: display portion, 6503: power button, 6504: button, 6505: speaker, 6506: microphone, 6507: camera, 6508: light source, 7000: display portion, 7200: notebook information terminal, 7211: housing, 7212: keyboard, 7213: pointing device, 7214: external connection port, 7215: camera, 8200: electronic device, 8201: mounting portion, 8202: lens, 8203: main body, 8204: display portion, 8205: cable, 8206: battery, 8300: electronic device, 8301: housing, 8302: display portion, 8304: fixing unit, 8305: lens, 8400: electronic device, 8401: housing, 8402: mounting portion, 8403: cushion, 8404: display portion, 8405: lens

The invention claimed is:

1. An electronic device comprising:
a communication portion;
an arithmetic circuit; and
a display portion comprising a pixel and a pixel circuit electrically connected to the pixel,
wherein the communication portion is configured to receive a plurality of images from a plurality of sensors, wherein each of the plurality of images includes an eye and a periphery of the eye of each of a plurality of users, wherein the arithmetic circuit is configured:

to detect, from the plurality of images received via the communication portion, a change over time in information including at least one of a frequency of eye blinks, a time taken for one blink, a distance between an upper eyelid and a lower eyelid, a sight direction, and an area of a pupil;

to determine, from the plurality of images received via the communication portion, whether each of the plurality of users is a user with high-level fatigue and to determine whether each of the plurality of users is a user who is looking away on the basis of a change over time in information including a sight direction; and to generate status information to recognize a user with high-level fatigue and a user who is looking away on the basis of the determined result among the plurality of users, wherein the arithmetic circuit is configured to distinguish the user with high-level fatigue from the user who is looking away as different situations, and wherein the display portion is configured to display the status information.

2. The electronic device according to claim 1, wherein the determination of whether each of the plurality of users has high-level fatigue is performed by estimating a level of the user's eye fatigue, wherein the level of user's eye fatigue is estimated using a learned model, and wherein the learned model is generated through supervised learning performed on a neural network.

3. The electronic device according to claim 2, wherein the arithmetic circuit is configured to perform a product-sum operation, and wherein the arithmetic circuit is configured to estimate the level of the user's eye fatigue on the basis of the change over time in information.

4. The electronic device according to claim 3, wherein the arithmetic circuit comprises a transistor comprising a metal oxide in a channel formation region.

5. An electronic device comprising:

an arithmetic circuit;

a display portion comprising a pixel and a pixel circuit electrically connected to the pixel; and a plurality of headphones configured to be put on a plurality of users, wherein each of the plurality of headphones comprise a sensor portion comprising a plurality of sensors, wherein the sensor portion is configured to obtain a change over time in information including at least one of a pulse, a blood pressure and a body temperature of a user putting on the headphones, wherein the arithmetic circuit is configured:

to estimate a user's stress situation on the basis of the change over time in information for the determination of whether each of the plurality of users is a user with high-level stress;

to determine whether each of the plurality of users is a user with high-level stress on the basis of the estimated user's stress situation;

to determine whether each of the plurality of users is a user who is looking away on the basis of a change over time in information including a sight direction of the user; and to generate string information in accordance with the determination of whether each user is a user with high-level stress and the determination of whether each user is a user who is looking away, wherein the arithmetic circuit is configured to distinguish the user with high-level fatigue from the user who is looking away as different situations, and wherein the display portion is configured to display the string information.

6. The electronic device according to claim 5, wherein the user's stress situation is estimated using a learned model, and wherein the learned model is generated through supervised learning performed on a neural network.

7. The electronic device according to claim 5, wherein the arithmetic circuit is configured to perform a product-sum operation, and wherein the arithmetic circuit is configured to estimate the user's stress situation on the basis of the change over time in information.

8. The electronic device according to claim 7, wherein the arithmetic circuit comprises a transistor comprising a metal oxide in a channel formation region.

9. A display system comprising a first electronic device and a second electronic device, wherein the first electronic device comprises a camera and an arithmetic circuit, wherein the second electronic device comprises a display portion, wherein the display portion comprises a pixel and a pixel circuit electrically connected to the pixel, wherein the camera is configured to obtain eye information of a user of the first electronic device by capturing an image including an eye of the user of the first electronic device, wherein the arithmetic circuit is configured to determine whether the user of the first electronic device is a user with high-level fatigue and to determine whether the user of the first electronic device is a user who is looking away, so that the first electronic device generates status information of the user of the first electronic device, wherein the determination of whether the user of the first electronic device is a user with high-level fatigue is estimated from the eye information on the basis of a change over time in information including at least one of a frequency of eye blinks, a time taken for one blink, a distance between an upper eyelid and a lower eyelid, and an area of a pupil of the user of the first electronic device, wherein the determination of whether the user of the first electronic device is a user with taking eyes off is estimated from the eye information on the basis of a change over time in information including a sight direction of the user of the first electronic device, wherein the arithmetic circuit is configured to distinguish the user with high-level fatigue from the user who is looking away as different situations, and wherein the display portion is configured to display the status information accepted from the first electronic device.

10. The display system according to claim 9, wherein a level of the user's eye fatigue is estimated using a learned model, wherein the determination of whether the user of the first electronic device is a user with high-level fatigue is estimated on the basis of the level of the user's eye fatigue, and wherein the learned model is generated through supervised learning performed on a neural network.

11. The display system according to claim 9, wherein the arithmetic circuit is configured to perform a product-sum operation, and wherein the arithmetic circuit estimates the level of the user's eye fatigue on the basis of the change over time in information.

12. The display system according to claim 9, wherein the camera is configured to capture an image of an eye and a periphery of the eye of the user of the first electronic device repeatedly in order to obtain the eye information of the user of the first electronic device, and wherein the arithmetic circuit is configured:

to detect, from the image, a change over time in information including said at least one of the frequency of eye blinks, the time taken for one blink, the distance between the upper eyelid and the lower eyelid, the sight direction, and the area of the pupil;

to estimate a level of user's eye fatigue on the basis of the change over time in information; and to generate string information corresponding to the status information in accordance with the estimated level of the user's eye fatigue.

13. The display system according to claim 9, wherein the first electronic device further comprises headphones, wherein the headphones comprise a sensor portion, wherein the sensor portion is configured to obtain a change over time in information including at least one of a pulse, a blood pressure and a body temperature of a user putting on the headphones, wherein the arithmetic circuit is configured to estimate a user's stress situation on the basis of the change over time in information obtained by the camera and the change over time in information obtained by the sensor portion, and wherein the arithmetic circuit is configured to generate string information in accordance with the user's stress situation.

14. The display system according to claim 13, wherein the user's stress situation is estimated using a learned model, and wherein the learned model is generated through supervised learning performed on a neural network.

15. The display system according to claim 13, wherein the arithmetic circuit is configured to perform a product-sum operation, and wherein the arithmetic circuit is configured to estimate the user's stress situation on the basis of the change over time in information.

* * * * *